(12) United States Patent
Saal et al.

(10) Patent No.: US 11,400,140 B2
(45) Date of Patent: Aug. 2, 2022

(54) METHODS FOR TREATING CRANIOSYNOSTOSIS IN A PATIENT

(71) Applicant: Alexion Pharmaceuticals, Inc., Boston, MA (US)

(72) Inventors: Howard M. Saal, Cincinnati, OH (US); Timothy W. Vogel, Cincinnati, OH (US)

(73) Assignee: Alexion Pharmaceuticals, Inc., Boston, MA (US)

(*) Notice: Subject to any disclaimer, the term of this patent is extended or adjusted under 35 U.S.C. 154(b) by 143 days.

(21) Appl. No.: 15/771,264

(22) PCT Filed: Oct. 30, 2015

(86) PCT No.: PCT/US2015/058498
§ 371 (c)(1),
(2) Date: Apr. 26, 2018

(87) PCT Pub. No.: WO2017/074466
PCT Pub. Date: May 4, 2017

(65) Prior Publication Data
US 2018/0326017 A1 Nov. 15, 2018

(51) Int. Cl.
*A61K 38/46* (2006.01)
*A61B 5/00* (2006.01)

(52) U.S. Cl.
CPC .... *A61K 38/465* (2013.01); *C12Y 301/03001* (2013.01); *A61B 5/4504* (2013.01); *A61B 2503/04* (2013.01)

(58) Field of Classification Search
None
See application file for complete search history.

(56) References Cited

U.S. PATENT DOCUMENTS

| | | | |
|---|---|---|---|
| 5,336,759 | A | 8/1994 | Matsuo et al. |
| 5,338,830 | A | 8/1994 | Matsuo et al. |
| 5,340,920 | A | 8/1994 | Matsuo et al. |
| 5,352,770 | A | 10/1994 | Matsuo |
| 5,428,130 | A | 6/1995 | Capon et al. |
| 5,434,133 | A | 7/1995 | Tanaka et al. |
| 5,583,108 | A | 12/1996 | Wei et al. |
| 5,665,704 | A | 9/1997 | Lowe et al. |
| 5,714,147 | A | 2/1998 | Capon et al. |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

Kosnik-Infinger et al., Neurosurg. Focus 38(5): E10 (2015).*

(Continued)

*Primary Examiner* — Erin M. Bowers
(74) *Attorney, Agent, or Firm* — Clark & Elbing LLP

(57) ABSTRACT

The disclosure features methods for treating craniosynostosis in a patient (e.g., a patient having hypophosphatasia (HPP) and exhibiting or likely to have increased intracranial pressure (ICP)) by administering a soluble alkaline phosphatase (sALP) to the patient, e.g., in combination with a cranial surgery, e.g., a cranial vault remodeling procedure.

29 Claims, 15 Drawing Sheets

Specification includes a Sequence Listing.

(56) References Cited

U.S. PATENT DOCUMENTS

| | | |
|---|---|---|
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,908,932 B2 | 3/2018 | Malanson et al. |
| 9,988,620 B2 | 6/2018 | Crine et al. |
| 10,000,532 B2 | 6/2018 | Crine et al. |
| 10,052,366 B2 | 8/2018 | Crine et al. |
| 10,449,236 B2 | 10/2019 | Marozsan et al. |
| 10,603,361 B2 | 3/2020 | Odrljin |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1* | 11/2010 | Crine ............... A61P 1/02 424/134.1 |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |

(56) References Cited

U.S. PATENT DOCUMENTS

| | | |
|---|---|---|
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2016/0097100 A1 | 4/2016 | Trent et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0771875 B1 | 5/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759001 | 3/2007 |
| EP | 1759710 A1 | 3/2007 |
| EP | 1985697 A1 | 10/2008 |
| EP | 2158319 | 3/2010 |
| EP | 2158319 B1 | 12/2011 |
| JP | H0870875 A | 3/1996 |
| JP | 2000-327583 A | 11/2000 |
| JP | 2002-541776 A | 12/2002 |
| JP | 2007-511209 A | 5/2007 |
| JP | 2007-537725 A | 12/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| JP | 2015-502336 A | 1/2015 |
| WO | WO-92/20371 A1 | 11/1992 |
| WO | WO-95/05456 | 8/1994 |
| WO | WO-94/20534 A1 | 9/1994 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/087802 A2 | 9/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/105156 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2015/112015 A1 | 7/2015 |
| WO | WO-2015/112017 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2016/153191 A1 | 9/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |

(56) References Cited

FOREIGN PATENT DOCUMENTS

| WO | WO-2017/173413 A1 | 10/2017 |
| --- | --- | --- |
| WO | WO-2017/214130 A1 | 12/2017 |
| WO | WO-2018/004517 A1 | 1/2018 |
| WO | WO-2018/035420 A1 | 2/2018 |
| WO | WO-2018/164995 A1 | 9/2018 |

OTHER PUBLICATIONS

Collmann et al., Childs Nerv. Syst. 25: 217-223 (2009).*
"View of NCT02235493 on Nov. 19, 2015," ClinicalTrials.gov archive, Nov. 19, 2015 (4 pages).
Achord et al., "Human beta-glucuronidase: in vivo clearance and in vitro uptake by a glycoprotein recognition system on reticuloendothelial cells," Cell 15(1):269-278 (1978).
Addison et al., "Pyrophosphate inhibits mineralization of osteoblast cultures by binding to mineral, up-regulating osteopontin, and inhibiting alkaline phosphate activity," J Biol Chem. 282(21 ):15872-15883 (2007).
Advisory Action for U.S. Appl. No. 11/484,870, dated Dec. 20, 2007 (4 pages).
Ahn et al., "Idiopathic calcium pyrophosphate dihydrate (CPPD) crystal deposition disease in a young male patient: a case report," J Korean Med Sci. 18(6):917-20 (2003).
Alexion Pharma International, "Strensiq Product Monograph," <http://alexionpharma.ca/documents/Strensiq-PM-asfotase-alfa-14Aug2015.aspx>, Prepared Aug. 14, 2015 (32 pages).
Alexion Third Quarter 2017 Earnings Call, "http://files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).
Alexion, "Highlights of Prescribing Information" for Strensiq®, 2018 (8 pages).
Ali et al., "Isolation and characterization of calcifying matrix vesicles from epiphyseal cartilage," Proc Natl Acad Sci USA. 67(3):1513-1520 (1970).
Altarescu et al., "The efficacy of enzyme replacement therapy in patients with chronic neuronopathic Gaucher's disease," J Pediatr. 138(4):539-547 (2001).
Anderson et al., "Impaired calcification around matrix vesicles of growth plate and bone in alkaline phosphatase-deficient mice," *Am J Pathol*. 164:841-847 (2004).
Anderson et al., "Matrix vesicles in osteomalacic hypophosphatasia bone contain apatite-like mineral crystals," Am J Pathol. 151(6):1555-61 (1997).
Anderson et al., "Pyrophosphate stimulation of calcium uptake into cultured embryonic bones. Fine structure of matrix vesicles and their role in calcification," Dev Biol. 34:211-227 (1973).
Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Anderson et al., "The role of matrix vesicles in growth plate development and biomineralization," Front Biosci. 10:822-837 (2005).
Appeal Brief as Filed in U.S. Appl. No. 12/638,527, dated Oct. 9, 2015 (101 pages).
Attwood, "The Babel of Bioinformatics," Genomics. 290(5491): 471-3 (2000).
Barranger et al., "Lessons learned from the development of enzyme therapy for Gaucher disease," J Inherit Metab Dis. 24(Supp 2):89-96 (2001).
Barton et al., "Replacement therapy for inherited enzyme deficiency—macrophage-targeted glucocerebrosidase for Gaucher's disease," N Engl J Med. 324(21):1464-70 (1991) (abstract only).
Beertsen et al., "Root development in mice lacking functional tissue non-specific alkaline phosphatase gene: Inhibition of acellular cementum formation," J Dent Res. 78(6):1221-1229 (1999) (10 pages).

Belachew et al., "Infantile hypophosphatasia secondary to a novel compound heterozygous mutation presenting with pyridoxine-responsive seizures," JIMD Rep. 11:17-24 (2013).
Belkhouribchia et al., "Case Report: Osteomalacia with low alkaline phosphatase: a not so rare condition with important consequences," BMJ Case Rep. doi: 10.1136/bcr-2015-212827 (2016) (4 pages).
Bennett et al., "Extracellular domain-IgG fusion proteins for three human natriuretic peptide receptors," J Biol Chem. 266(34):23060-23067 (1991).
Berkseth et al., "Clinical spectrum of hypophosphatasia diagnosed in adults," Bone. 54(1):21-7 (2013).
Bernard, "Ultrastructural localization of alkaline phosphatase in initial intramembranous osteogenesis," Clin Orthop Relat Res. 135:218-225 (1978).
Bernardi, "Chromatography of proteins on hydroxyapatite," Methods Enzymol. 27:471-9 (1973).
Bhattacharyya et al., "Hypophosphatasia and the risk of atypical femur fractures: a case-control study," BMC Muscoloskelet Disord. 17:332 (2016) (4 pages).
Bianchi, "Hypophosphatasia: an overview of the disease and its treatment," Osteoporos Int. 26(12):2743-57; DOI 10.1007/s00198-015-3272-1 (2015) (15 pages).
Bishop et al., "Transformative therapy in hypophosphatasia," Arch Dis Child. 101(6):514-5 (2016).
Bishop, "Asfotase alfa for hypophosphatasia," Horizon Scanning Centre. National Institute for Health Research, http://www.hsric.nihr.ac.uk/topics/asfotase-alfa-for-hypophosphatasia/download, retrieved Oct. 20, 2013 (9 pages).
Bishop, "Clinical management of hypophosphatasia," Clin Cases Miner Bone Metab. 12(2):170-3 (2015).
Bloch-Zupan, "Hypophosphatasia: diagnosis and clinical signs—a dental surgeon perspective," Int J Paediatr Dent. 26(6):426-438 (2016).
Bobryshev et al., "Role of bone-type tissue-nonspecific alkaline phosphatase and PHOSPO1 in vascular calcification," Curr Pharm Des. 20(37):5821-8 (2014).
Bobé et al., "Fas-mediated liver damage in MRL hemopoietic chimeras undergoing lpr-mediated graft-versus-host disease," J Immunol. 159:4197-4204(1997).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Bonilla, "Pharmacokinetics of immunoglobulin administered via intravenous or subcutaneous routes," Immunol Allergy Clin N Am. 28:803-819 (2008).
Boskey et al., "Matrix vesicles promote mineralization in a gelatin gel," Calcif Tissue Int 60(3):309-15 (1997).
Boskey, "Amorphous calcium phosphate: The contention of bone," J Dent Res. 76:1433-1436 (1997).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Braunstein, "Multiple fractures, pain, and severe disability in a patient with adult-onset hypophosphatasia," Bone Rep. 4:1-4 (2015).
Brenner et al., "Diverse biological actions of atrial natriuretic peptide," Physiol Rev. 70(3):665-699 (1990).
Briot et al., "Adult hypophosphatasia," Curr Opin Rheumatol. 28(4):448-51 (2016).
Buchet et al., "Multisystemic functions of alkaline phosphatases," Methods Mol Biol. 1053:27-51 (2013).
Byers et al., "Effect of enzyme replacement therapy on bone formation in a feline model of mucopolysaccharidosis type VI," Bone. 21(5):425-431 (1997).
Cahill et al., "Infantile hypophosphatasia: transplantation therapy trial using bone fragments and cultured osteoblasts,"J. Clin Endocrinol Metab. 92(8): 2923-30 (2007).
Cameron et al., "Minireview: Natriuretic peptides during development of the fetal heart and circulation," Endocrinology. 144(6):2191-2194 (2003).
Campbell et al., "Insulin-like growth factor (IGF)-binding protein-5-(201-218) region regulates hydroxyapatite and IGF-I binding," Am J Physiol. 273:E1005-1013 (1997).

(56) References Cited

OTHER PUBLICATIONS

Chen et al., "Gly369Cys mutation in mouse FGFR3 causes achondroplasia by affecting both chondrogenesis and osteogenesis," J Clin Invest. 104(11):1517-1525 (1999).
Choe et al., "Substrate profiling of cysteine proteases using a combinatorial peptide library identifies functionally unique specificities," J Biol Chem. 281(18):12824-12832 (2006).
Chusho et al., "Dwarfism and early death in mice lacking C-type natriuretic peptide," Proc Natl Acad Sci USA. 98(7):4016-4021 (2001).
Ciancaglini et al., "Contribution of matrix vesicles and alkaline phosphatase to ectopic bone formation," Braz. J Med Biol Res. 39(5):603-10 (2006).
Cleland et al., "Emerging protein delivery methods," Curr Opin Biotechnol. 12:212-219 (2001).
Clemens et al., "Pharmacokinetics and biological actions of subcutaneously administered human brain natriuretic peptide," J Pharmacol Exp Ther. 287(1):67-71 (1998).
Communication from Examining Division for European Application No. EP 05 73 9065.0, dated Jun. 11, 2010 (5 pages).
Communication from Examining Division for European Application No. EP 05 73 9065.0, dated Jun. 18, 2009 (6 pages).
Communication from Examining Division for European Application No. EP 08 757 088.3, dated Apr. 20, 2011 (4 pages).
Crawley et al., "Enzyme replacement therapy in a feline model of Maroteaux-Lamy Syndrome," J Clin Invest. 97(8):1864-73 (1996).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
Data Sheet for pFUSE-SEAP-hFC "Plasmid designed for the expression of a SEAP-Fc Fusion protein," Invivogen, San Diego, CA (4 pages) (1989).
De la Croix Ndong et al., "Asfotase-alpha improves bone growth, mineralization and strength in mouse models of neurofibromatosis type-1," Nat Med. 20(8):904-10 (2014) (10 pages).
De Plater et al., "The natriuretic peptide (OVCNP-39) from platypus (Ornithorhynchus anatinus) venom relaxes the isolated rat uterus and promotes oedema and mast cell histamine release," Toxicon. 36(3):847-857 (1998).
Declaration of Dr. Philippe Crine for EP 08757088.3, executed Jan. 14, 2011 (6 pages).
Deeb et al., "Could alerting physicians for low alkaline phosphatase levels be helpful in early diagnosis of hypophosphatasia?," J Clin Res Pediatr Endocrinol. 10(1):19-24 (2018).
Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
Durussel et al., "Bone mineralization-dependent craniosynostosis and craniofacial shape abnormalities in the mouse model of infantile hypophosphatasia," Dev Dyn. 245(2):175-82 (2016).
EBI Blast for Accession No. ATD17216. Entered Oct. 16, 2008 (1 page).
Eng et al., "Safety and efficacy of recombinant human alpha-galactosidase A—replacement therapy in Fabry's disease," N Engl J Med. 345(1):9-16 (2001).
Engel et al., "Characterization of the hormone binding site of natriuretic peptide receptor-C," FEBS Lett. 360:169-172(1995).
Epps, "Application No. 125513Orig1s000 Medical Review(s)," Center for Drug Evaluation and Research, <http://www.accessdata.fda.gov/drugsatfda_docs/nda/2015/125513Orig1s000MedR.pdf>, Oct. 20, 2015 (254 pages).
European Collection of Authenticated Cell Cultures (ECACC) Accession No. 85110503. Retrieved May 2, 2018 (3 pages).
European Search Report for European Application No. EP08757088, dated Jun. 21, 2010 (6 pages).
European Search Report for European Patent Application No. 12842640.0, dated Mar. 13, 2015 (7 pages).
Examiner's Answer to Appeal Brief for U.S. Appl. No. 12/638,527, dated Feb. 23, 2016 (9 pages).
Extended European Search Report for European Application No. 11774253.6, dated Oct. 14, 2013 (8 pages).
Extended European Search Report for European Application No. EP 11 00 0196.3, dated Jun. 22, 2011 (6 pages).
Extended European Search Report for European Application No. EP 11 00 4496.3, dated Aug. 26, 2011 (7 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Fodor et al., "Differencial diagnosis of the low alkaline phosphatase activities," Orv Hetil. 158(26): 1003-1007 (2017) (Article in Hungarian) (English Abstract included).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Furuya et al., "Structural requirements of C-type natriuretic peptide for elevation of cyclic GMP in cultured vascular smooth muscle cells," Biochem Biophys Res Commun. 183(3):964-969 (1992).
Garg, Investigation of the role of FcRn in the absorption, distribution, and elimination of monoclonal antibodies. Dissertation: State University of New York at Buffalo, 2007 (Abstract only) (2 pages).
Gasque et al., "Improvement of the skeletal and dental hypophosphatasia phenotype in Alpl -/- mice by administration of soluble (non-targeted) chimeric alkaline phosphatase," Available in PMC Mar. 1, 2016, published in final edited form as: Bone. 72:137-147 (2015) (25 pages).
Gilbert et al., "Chimeric peptides of statherin and osteopontin that bind hydroxyapatite and mediate cell adhesion," J Biol Chem. 275(21):16213-8 (2000).
Glass et al., "The infant skull: a vault of information," Radiographics. 24(2):507-22 (2004).
Graham et al., "Characteristics of a human cell line transformed by DNA from human adenovirus type 5," J Gen Virol. 36(1):59-74 (1977).
Greenberg et al., "A homoallelic Gly[317] to Asp mutation in *ALPL* causes the perinatal (lethal) form of hypophosphatasia in Canadian mennonites," Genomics. 17:215-217 (1993).
Guo et al., "Protein tolerance to random amino acid change," Proc Natl Acad Sci USA. 101(25):9205-9210(2004).
Güzel et al., "Pyridoxine-responsive seizures in infantile hypophosphatasia and a novel homozygous mutation in ALPL gene," J Clin Res Pediatr Endocrinol. 8(3):360-4 (2016).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol. 270:C1311-C1318 (1996).
Hailing Linder et al., "Glycosylation differences contribute to distinct catalytic properties among bone alkaline phosphotase isoforms," available in PMC Nov. 1, 2010, published in final edited form as: Bone. 45(5):987-993 (2009) (17 pages).
Hardy et al., "Dissection of a carboxy-terminal region of the yeast regulatory protein RAP1 with effects on both transcriptional activation and silencing," Mol Cell Biol. 12(3):1209-1217 (1992).

(56) References Cited

OTHER PUBLICATIONS

Harmey et al., "Concerted regulation of inorganic pyrophosphate and osteopontin by Akp2, Enpp1, and Ank" Am J Pathol. 164(4):1199-1209 (2004).
Harmey et al., "Elevated skeletal osteopontin levels contribute to the hypophosphatasia phenotype in Akp2$^{-/-}$ mice," J Bone Miner Res. 21(9):1377-1386 (2006).
Harris, "The human alkaline phosphatases: what we know and what we don't know," Clin Chim Acta. 186:133-50 (1989).
Hawrylak et al., "The solubilization of tetrameric alkaline phosphatase from human liver and its conversion into various forms by phosphatidylinositol phospholipase C or proteolysis," J Biol Chem. 263(28):1 4368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Henthorn et al., "Missense mutations of the tissue-nonspecific alkaline phosphatase gene in hypophosphatasia," Clin Chem. 38(12):2501-5 (1992).
Herasse et al., "Molecular study of three cases of odontohypophosphatasia resulting from heterozygosity for mutations in the tissue non-specific alkaline phosphatase gene," J Med Genet. 40(8):605-9 (2003).
Hessle et al., "Tissue-nonspecific alkaline phosphatase and plasma cell membrane glucoprotein-1 are central antagonistic regulators of bone mineralization," Proc Natl Acad Sci USA. 99(14): 9445-9449 (2002).
Highlights of Prescribing Information for Strensiq™, Alexion Pharmaceuticals, Inc., available <http://www.alexion.com/Documents/strensiq_pi-10-2015.aspx>, 2015 (19 pages).
Hofmann et al., "Asfotase alfa: enzyme replacement for the treatment of bone disease in hypophosphatasia," Drugs Today (Barc). 52(5):271-85 (2016).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Austria, Salzburg. Bone Abstracts. 4: OC18 (2015) (3 pages).
Hofmann et al., "Recombinant enzyme replacement therapy in hypophosphatasia," Subcell Biochem. 76:323-41 (2015).
Horton et al., "Achondroplasia," Lancet. 370:162-172, 2007.
Hosain et al., "Targeted delivery of antineoplastic agent to bone: biodistribution studies of technetium-99m-labeled gem-bisphosphonate conjugate of methotrexate," J Nucl Med. 37(1):105-7(1996).
Hult et al., "Engineered enzymes for improved organic synthesis," Curr Opin Biotechnol. 14:395-400 (2003).
Hunter et al., "Modulation of crystal formation by bone phosphoproteins: structural specificity of the osteopontin-mediated inhibition of hydroxyapatite formation," Biochem J. 300:723-728 (1994).
Husain et al., "Fc site-specific labeling of immunoglobulins with calf intestinal alkaline phosphatase," Bioconjug Chem. 5(5):482-90 (1994).
Ikezawa, "Glycosylphosphatidylinositol (GPI)-anchored proteins," Biol Pharm Bull. 25(4):409-417 (2002).
Inoue et al., "Four functionally distinct C-type natriuretic peptides found in fish reveal evolutionary history of the natriuretic peptide system," Proc Natl Acad Sci USA. 100(17):10079-10084 (2003).
International Preliminary Report on Patentability for International Patent Application No. PCT/CA2011/050258, dated Nov. 15, 2012 (9 pages).
International Preliminary Report on Patentability for International Patent Application No. PCT/US2012/039004, dated Apr. 22, 2014 (8 pages).
International Preliminary Report on Patentability for International Patent Application No. PCT/US2012/060869, dated Apr. 22, 2014 (7 pages).
International Preliminary Report on Patentability for International Patent Application No. PCT/US2016/015366, dated Aug. 10, 2017 (10 pages).
International Search Report and Written Opinion for International Patent Application No. PCT/CA2005/000615, dated Aug. 18, 2005 (14 pages).
International Search Report and Written Opinion for International Patent Application No. PCT/CA2008/000923, dated Sep. 12, 2008 (11 pages).
International Search Report and Written Opinion for International Patent Application No. PCT/CA2011/050258, dated Jul. 29, 2011 (14 pages).
International Search Report and Written Opinion for International Patent Application No. PCT/CA2011/050807, dated Apr. 13, 2012 (18 pages).
International Search Report and Written Opinion for International Patent Application No. PCT/US2012/039004, dated Nov. 2, 2012 (22 pages).
International Search Report and Written Opinion for International Patent Application No. PCT/US2016/025721, dated Aug. 17, 2016 (18 pages).
International Search Report and Written Opinion for International Patent Application No. PCT/US2016/054013, dated Dec. 13, 2016 (19 pages).
International Search Report and Written Opinion for International Patent Application No. PCT/US2015/058498, dated Jan. 22, 2016 (12 pages).
International Search Report and Written Opinion for International Patent Application No. PCT/US2016/039595, dated Feb. 21, 2017 (16 pages).
International Search Report and Written Opinion for International Patent Application No. PCT/US2016/047166, dated Nov. 7, 2016 (15 pages).
International Search Report and Written Opinion for International Patent Application No. PCT/US2017/025590, dated Jun. 29, 2017 (18 pages).
International Search Report and Written Opinion for International Patent Application No. PCT/US2017/047527, dated Nov. 6, 2017 (10 pages).
International Search Report for International Patent Application No. PCT/US2012/060869, dated Mar. 25, 2013 (5 pages).
Invitation to Pay Additional Fees for International Patent Application No. PCT/CA2011/050807, dated Feb. 13, 2012 (2 pages).
Invitation to Pay Additional Fees for International Patent Application No. PCT/US2012/039004, dated Aug. 29, 2012 (2 pages).
Invitation to Pay Additional Fees for International Patent Application No. PCT/US2016/015366, dated Jun. 1, 2016 (7 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ishida et al., "Tissue-nonspecific alkaline phosphatase with an Asp(289)→Val mutation fails to reach the cell surface and undergoes proteasome-mediated degradation," J Biochem. 134(1 ):63-70 (2003).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Kakkis et al., "Enzyme-replacement therapy in mucopolysaccharidosis I," N Engl J Med. 344(3):182-8 (2001).
Kalra et al., "The role of C-type natriuretic peptide in cardiovascular medicine," Eur Heart J. 22:997-1007 (2001).
Kasugai et al., "Selective drug delivery system to bone: small peptide $(Asp)_6$ conjugation," J Bone Miner Res. 15(5):936-943 (2000).
Kaufmann et al., "Influence of low temperature on productivity, proteome and protein phosphorylation of CHO cells," Biotechnol Bioeng. 63(5):573-82 (1999).

(56) References Cited

OTHER PUBLICATIONS

Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, April 1-4, Boston, MA. Abstract OR26-3 (2016) (2 pages).
Kishnani et al., "Monitoring guidance for patients with hypophosphatasia treated with asfotase alfa," Mol Genet Metab. 122(1-2):4-17 (2017).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Kochendoerfer, "Protein & peptide drug delivery—third international conference: Minimally invasive delivery methods," IDrugs. 6(11):1043-1045 (2003).
Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Kostenuik et al., "Infrequent delivery of a long-acting PTH-Fc fusion protein has potent anabolic effects on cortical and cancellous bone," J Bone Miner Res. 22(10):1534-1547 (2007).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Le Du et al., "Crystal structure of alkaline phosphatase from human placenta at 1.8 A resolution. Implication for a substrate specificity," J Biol Chem. 276(12):9158-65 (2001) (9 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Leone et al., "Allosteric modulation of pyrophosphatase activity of rat osseous plate alkaline phosphatase by magnesium ions," Int J Biochem Cell Biol. 30:89-97 (1998).
Linglart et al., "Hypophosphatasia," Curr Osteoporos Rep. 14(3):95-105; DOI 10.1007/s11914-016-0309-0 (2016) (11 pages).
Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Lo et al., "High level expression and secretion of Fc-X fusion proteins in mammalian cells," Protein Eng. 11 (6):495-500 (1998).
Madson et al., "Asfotase alfa: sustained efficacy and tolerability in children with hypophosphatasia treated for 5 years," ESPE Abstracts. 84:FC2.4 (2015) (2 pages).
Mahmood et al., "Selection of the first-time dose in humans: comparison of different approaches based on interspecies scaling of clearance," J Clin Pharmacol. 43:692-697 (2003).
Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).
Mather, "Establishment and characterization of two distinct mouse testicular epithelial cell lines," Biol Reprod. 23(1):243-52 (1980).
Mayer, "Microbiology and immunology on-line: Immunoglobulins: structure and function" <http://pathmicro.med.sc.edu/mayer/IgStruct2000.htm>, University of South Carolina School of Medicine, 12 pages (2009).
McKiernan et al., "Clinical and radiographic findings in adults with persistent hypophosphatasemia," J Bone Miner Res. 29(7):1651-60 (2014).
Mericq et al., "Regulation of fetal rat bone growth by C-type natriuretic peptide and cGMP," Pediatr Res. 47(2):189-193 (2000) (9 pages).
Meyer, "Can biological calcification occur in the presence of pyrophosphate?" Arch Biochem Biophys. 231:1-8(1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Millan, "Mammalian Alkaline Phosphatases," Wiley-WCH Verlag GmbH & Co., Weinheim, Germany, 1-322 (2006).
Millán et al., "Alkaline phosphatase and hypophosphatasia," Calcif Tissue Int. 98(4):398-416 (2016).
Millán et al., "Enzyme replacement therapy for murine hypophosphatasia," J Bone Miner Res. 23(6): 777-87 (2008).
Millán et al., "Hypophosphatasia—pathophysiology and treatment," available in PMC Sep. 22, 2014, published in final edited form as: Actual Osteol. 8(3):164-182 (2012) (21 pages).
Miyazawa et al., "Cyclic GMP-dependent protein kinase II plays a critical role in C-type natriuretic peptide-mediated endochondral ossification," Endocrinology. 143(9):3604-3610 (2002).
Mori et al., "Case series: odontohypophosphatasia or missed diagnosis of childhood/adult-onset hypophosphatasia? —Call for a long-term follow-up of premature loss of primary teeth," Bone Rep. 5:228-232 (2016).
Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Mornet et al., "Structural evidence for a functional role of human tissue nonspecific alkaline phosphatase in bone mineralization," J Biol Chem. 276(33):31171-8 (2001).
Mornet, "Hypophosphatasia," Orphanet J Rare Dis. 2:(40) (2007) (8 pages).
Mornet, "Hypophosphatasia," Metabolism. 82:142-155; DOI: 10.1016/j.metabol.2017.08.013 (2018) (30 pages).
Mornet, "Molecular genetics of hypophosphatasia and phenotype-genotype correlations," Subcell Biochem. 76:25-43 (2015).
Morris et al., "Immunolocalization of alkaline phosphatase in osteoblasts and matrix vesicles of human fetal bone," Bone Miner. 19:287-298 (1992).
Morrow, "Expensive new biologic helps children fight hypophosphatasia," Manag Care. 24(12) (2015) (7 pages).
Moss et al., "Association of inorganic-pyrophosphatase activity with human alkaline-phosphatase preparations," Biochem J. 102:53-57 (1967).
Murray, "Lectin-specific targeting of lysosomal enzymes to reticuloendothelial cells," Methods Enzymol. 149:25-42 (1987).
Murshed et al., "Unique coexpression in osteoblasts of broadly expressed genes accounts for the spatial restriction of ECM mineralization to bone," Genes Dev. 19:1093-1104 (2005).
Nahabet et al., "Postnatal Pancraniosynostosis in a Patient With Infantile Hypophosphatasia," Cleft Palate Craniofac J. 53(6):741-4 (2016).
Nakao et al., "The pharmacokinetics of alpha-human atrial natriuretic polypeptide in healthy subjects," Eur J Clin Pharmacol. 31:101-103 (1986).
Narisawa et al., "Abnormal vitamin B6 metabolism in alkaline phosphatase knock-out mice causes multiple abnormalities, but not the impaired bone mineralization," J Pathol. 193:125-133 (2001).
Narisawa et al., "Inactivation of two mouse alkaline phosphatase genes and establishment of a model of infantile hypophosphatasia," Dev Dyn. 208:432-446 (1997).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAC33858. Retrieved on Apr. 16, 2013 (1 page).
NCBI Protein Database Accession No. AAF64516. Retrieved on Apr. 16, 2013 (2 pages).
NCBI Protein Database Accession No. AAH21289. Retrieved on Apr. 16, 2013 (2 pages).
NCBI Protein Database Accession No. AAH66116. Retrieved on Apr. 16, 2013 (2 pages).

(56) References Cited

OTHER PUBLICATIONS

NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI18209. Retrieved on Apr. 17, 2013 (2 pages).
NCBI Protein Database Accession No. AAI26166. Retrieved on Apr. 16, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (2 pages).
NCBI Protein Database Accession No. NP_001036028. Retrieved on Apr. 16, 2013 (2 pages).
NCBI Protein Database Accession No. NP_001253798.1, downloaded on Apr. 17, 2013. (2 pages).
NCBI Protein Database Accession No. NP_001622. Retrieved on Apr. 16, 2013 (3 pages).
NCBI Protein Database Accession No. NP_001623. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_112603. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09242. Retrieved on Apr. 16, 2013 (6 pages).
NCBI Protein Database Accession No. P09487. Retrieved on Apr. 16, 2013 (4 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q6PYX1. Retrieved on Oct. 15, 2013 (2 pages).
NCBI Protein Database Accession No. Q9N0V0. Retrieved on Apr. 16, 2013 (1 page).
NCBI Protein Database Accession No. XP_001109717. Retrieved on Apr. 17, 2013 (1 page).
Ngo et al., Computational complexity, protein structure prediction, and the levinthal paradox. *The Protein Folding Problem and Tertiary Structure Prediction*. Merz et al. (ed.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Nosjean et al., "Human tissue non-specific alkaline phosphatases: sugar-moiety-induced enzymic and antigenic modulations and genetic aspects," Biochem J. 321:297-303 (1997).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).
Office Action for U.S. Appl. No. 11/484,870, dated Feb. 2, 2009 (16 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).
Office Action for U.S. Appl. No. 12/793,517, dated Aug. 16, 2010 (9 pages).
Office Action for U.S. Appl. No. 13/071,445, dated Feb. 6, 2012 (12 pages).
Office Action for U.S. Appl. No. 13/071,445, dated May 25, 2012 (14 pages).
Official Action for Japanese Application No. 2013-544989, dated Oct. 27, 2015 (3 pages).
Official Notification and Search Report for Eurasian Patent Application No. 201291138, dated May 17, 2013 (3 pages).
Oikawa et al., "Enzyme replacement therapy on hypophosphatasia mouse model," J Inherit Metab Dis. 9 pages (2013).
Okazaki et al., "Lethal hypophosphatasia successfully treated with enzyme replacement from day 1 afterbirth," Eur J Pediatr. 175(3):433-7; DOI 10.1007/s00431-015-2641-2 (2016) (5 pages).
Orimo, "Pathophysiology of hypophosphatasia and the potential role of asfotase alfa," Ther Clin Risk Manag. 12:777-86 (2016).
Orimo, "The mechanism of mineralization and the role of alkaline phosphatase in health and disease," J Nippon Med Sch. 77(1):4-12 (2010).
Padidela et al., "Enzyme-replacement therapy in life-threatening perinatal hypophosphatasia in a premature infant," Endocrine Abstracts. 33:P9 (2013) (1 page).
Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Panesar, "Hypophosphatasia: a rare disorder," US Pharm. 42(5) (2017) (8 pages).
Park et al., "First Korean case of infantile hypophosphatasia with novel mutation in ALPL and literature review," Ann Clin Lab Sci. 46(3):302-7 (2016).
Patti et al., "Critical residues in the ligand-binding site of the *Staphylococcus aureus* collagen-binding adhesin (MSCRAMM)," J Biol Chem. 270(20):12005-12011 (1995).
Pedersen et al., "Removal of N-terminal polyhistidine tags from recombinant proteins using engineered aminopeptidases," Protein Expr Purif. 15(3):389-400 (1999).
Pfeifer et al., "Intestinal secretory defects and dwarfism in mice lacking cGMP-dependent protein kinase II," Science. 274:2082-2086 (1996).
Phillips et al., "A modified performance-oriented mobility assessment tool for assessing clinically relevant gait impairments and change in children with hypophosphatasia: development and validation," Bone Abstracts. 4 P136 (2015).
Phillips et al., "Gait assessment in children with childhood hypophosphatasia: impairments in muscle strength and physical function," The Endocrine Society's 97th Annual Meeting & Expo, Mar. 5-8, 2015, San Diego, California (2 pages).
Phillips et al., "Physical therapy management of infants and children with hypophosphatasia," Mol Genet Metab. 119(1-2):14-9 (2016).

(56) References Cited

OTHER PUBLICATIONS

Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Potter et al., "Natriuretic peptides, their receptors, and cyclic guanosine monophosphate-dependent signaling functions," Endocr Rev. 27(1):47-72 (2006).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Ratner, "Alexion pays big for Synageva's rare disease drug candidate," Nat Biotechnol. 33(7):679 (2015).
Remde et al., "Successful asfotase alfa treatment in an adult dialysis patient with childhood-onset hypophosphatasia," J Endoc Soc. 1(9):1188-93 (2017).
Reply Brief as Filed in U.S. Appl. No. 12/638,527, dated Apr. 22, 2016 (4 pages).
Reply to Final Office Action for U.S. Appl. No. 13/071,445, dated Oct. 25, 2012 (14 pages).
Reply to Office Action for U.S. Appl. No. 11/111,664, dated Sep. 10, 2008 (32 pages).
Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961-969(1971).
Saglam et al., "Clinical and genetic findings of Turkish hypophosphatasia cases," J Clin Res Pediatr Endocrinol. 9(3):229-236 (2017).
Salih et al., "Identification of the phosphorylated sites of metabolically 32P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Saraff et al., "A diagnostic algorithm for children with low alkaline phosphatase activities: lessons learned from laboratory screening for hypophosphatasia," J Pediatr. 172:181-6 (2016) (7 pages).
Sather, "008-case study: 3 year old female with hypophosphatasia, treated with asfotase alfa replacement," Journal of Pediatric Nursing. 34:104 (2017).
Sawai et al., "Severe perinatal hypophosphatasia due to homozygous deletion of T at nucleotide 1559 in the tissue nonspecific alkaline phosphatase gene,". Prenat Diagn. 23(9):743-6 (2003).
Schindeler et al., "Modeling bone morphogenetic protein and bisphosphonate combination therapy in wild-type and Nf1 haploinsufficient mice," J Orthop Res. 26(1):65-74 (2008).
Schmidt et al., "Clinical radiographic and biochemical characteristics of adult hypophosphatasia," Osteoporos Int. 28(9):2653-2662 (2017).
Schmidt et al., "Hypophosphatasia: What is currently available for treatment?" Internist (Berl). 57(12):1145-1154 (2016) (Article in German) (English abstract).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL. (1 page).
Sekido et al., "Novel drug delivery system to bone using acidic oligopeptide: pharmacokinetic characteristics and pharmacological potential," J Drug Target. 9(2):111-21 (2001).
Shapiro et al., "Hypophosphatasia in adults: clinical assessment and treatment considerations," J Bone Miner Res. 32(10):1977-1980 (2017).
Sharom et al., "Glycosylphosphatidylinositol-anchored proteins: structure, function, and cleavage by phosphatidylinositol-specific phospholipase C," Biochem Cell Biol. 80:535-549 (2002).
Sheikh et al., "A newborn with no bones: neonatal hypophosphatasia with respiratory distress," J Pediatr. 188:306 (2017).
Shukla et al., "RNA interference and inhibition of MEK-ERK signaling prevent abnormal skeletal phenotypes in a mouse model of craniosynostosis," Nat Genet. 39(9):1145-1150 (2007).
Shull et al., "Enzyme replacement in a canine model of hurler syndrome," Proc Natl Acad Sci USA. 91:12937-12941 (1994).
Siller et al., "Alkaline phosphatase: discovery and naming of our favorite enzyme," J Bone Miner Res. 33(2):362-4 (2018).
Simm et al., "Successful use of enzyme replacement therapy in infantile hypophosphatasia," J Paediatr Child Health. 53(9):925-926 (2017).
Siris et al., "Paget's disease of bone," Trends Endocrinol Metab. 2(6):207-12 (1991).
Skolnick et al., "From genes to protein structure and function: novel applications of computational approaches in the genomic era," Trends Biotechnol. 18(1):34-9 (2000).
Sotillo et al., "Signs and symptoms of hypophosphatasia," Dimensions of Dental Hygiene. 15(4):44-47 (2017).
Spears et al., "Deoxyuridylate effects on thymidylate synthase-5-fluorodeoxyuridylate-folate ternary complex formation," Biochem Pharmacol. 38(18):2985-2993 (1989).
Spentchian et al., "Severe hypophosphatasia: characterization of fifteen novel mutations in the ALPL gene," Hum Mutat. 22(1) (2003) (5 pages).
Srinivas et al., "Assessment of dose proportionality, absolute bioavailability, and immunogenicity response of CTLA4Ig (BMS-188667), a novel immunosuppressive agent, following subcutaneous and intravenous administration to rats," Pharmaceutical Res. 14(7): 911-916 (1997).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Stec et al., "A revised mechanism for the alkaline phosphatase reaction involving three metal ions," J Mol Biol. 299(5):1303-11 (2000).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Suda et al., "C-type natriuretic peptide as an autocrine/paracrine regulator of osteoblast: evidence for possible presence of bone natriuretic peptide system," Biochem Biophys Res Commun. 223:1-6 (1996).
Supplementary European Search Report for European Application No. EP 05 73 9065 (date of completion of search Nov. 7, 2008, dated Dec. 2, 2008).
Supplementary European Search Report for European Application No. EP 08757088, date of completion Jun. 7, 2010 (5 pages).
Supplementary European Search Report for European Patent Application No. 11853820.6, dated Mar. 25, 2014 (3 pages).
Symersky et al., "Structure of the collagen-binding domain from a *Staphylococcus aureus* adhesin," Nat Struct Biol. 4(10):833-838 (1997).
Takahashi et al., "Parental serum alkaline phosphatase activity as an auxiliary tool for prenatal diagnosis of hypophosphatasia," Prenat Diagn. 37(5):491-6 (2017).
Takano et al., "Molecular evolution of shark C-type natriuretic peptides," Zoolog Sci. 11:451-454 (1994).

(56) References Cited

OTHER PUBLICATIONS

Taketani et al., "Ex vivo expanded allogeneic mesenchymal stem cells with bone marrow transplantation improved osteogenesis in infants with severe hypophosphatasia," Cell Transplant. 24(10):1931-43 (2015).
Takinami et al.. "The mutant (F310L and V365I) tissue-nonspecific alkaline phosphatase gene from hypophosphatasia," J Med Dent Sci. 51(1):67-74 (2004).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319:171-178 (2008).
Tenorio et al., "Molecular and clinical analysis of ALPL in a cohort of patients with suspicion of hypophosphatasia," Am J Med Genet A. 173(3):601 -10 (2017).
Tomatsu, Declaration Under 37 C.F.R. § 1.132 for U.S. Appl. No. 11/484,870, dated Jun. 1, 2009 (3 pages).
Tomatsu, Declaration Under 37 C.F.R. § 1.132 for U.S. Appl. No. 11/484,870, dated Nov. 27, 2007 (2 pages).
Tsiantouli et al., "Hypophosphatasia," Rev Med Suisse. 13(559):855-8 (2017) (Article in French).
Tsuji et al., "A loss-of-function mutation in natriuretic peptide receptor 2 (Npr2) gene is responsible for disproportionate dwarfism in cn/cn mouse," J Biol Chern. 280(14):14288-14292 (2005).
Tye et al., "Delineation of the hydroxyapatite-nucleating domains of bone sialoprotein," J Biol Chem. 278(10):7949-7955 (2003).
Uludag et al., "Bone affinity of a bisphosphonate-conjugated protein in vivo," Biotechnol Prog. 16(6):1115-8 (2000).
UniProtKB Accession No. P01857. Retrieved May 2, 2018 (13 pages).
UniProtKB Accession No. P05186. Retrieved May 2, 2018 (19 pages).
Urlaub et al., "Deletion of the diploid dihydrofolate reductase locus from cultured mammalian cells," Cell. 33:405-412 (1983).
Urlaub et al., "Isolation of Chinese hamster cell mutants deficient in dihydrofolate reductase activity," Proc Natl Acad Sci U S A. 77(7):4216-20 (1980).
Wang et al., "A mouse model for achondroplasia produced by targeting fibroblast growth factor receptor 3," Proc Natl Acad Sci USA. 96:4455-4460 (1999).
Wang et al., "Current concepts in odontohypophosphatasia form of hypophosphatasia and report of two cases," BMC Oral Health. 16(1):70 (2016) (8 pages).
Wang et al., "Mice lacking Nf1 in osteochondroprogenitor cells display skeletal dysplasia similar to patients with neurofibromatosis type 1," Hum Mol Genet. 20(20):3910-3924 (2011).
Wang et al., "Structure-based chemical modification strategy for enzyme replacement treatment of phenylketonuria," Mol Genet Metab. 86:134-140 (2005).
Waymire et al., "Mice lacking tissue non-specific alkaline phosphatase die from seizures due to defective metabolism of vitamin B-6," Nat Genet. 11(1):45-51 (1995).
Weber et al., "Burden of disease in adult patients with hypophosphatasia: Results from two patient-reported surveys," Metabolism. 65(10):1522-30 (2016).
Weinberg, "An overview of infliximab, etanercept, efalizumab, and alefacept as biologic therapy for psoriasis," Clin Ther. 25(10):2487-505 (2003).
Weiss et al., "A missense mutation in the human liver/bone/kidney alkaline phosphatase gene causing a lethal form of hypophosphatasia," Proc Natl Acad Sci USA. 85:7666-7669 (1988).
Weiss et al., "Isolation and characterization of a cDNA encoding a human liver/bone/kidney-type alkaline phosphatase," Proc Natl Acad Sci USA. 83(19):7182-6 (1986).
Weiss et al., "Structure of the human liver/bone/kidney alkaline phosphatase gene," J Biol Chem. 263(24):12002-10 (1988).

Weninger et al., "Biochemical and morphological effects of human hepatic alkaline phosphatase in a neonate with hypophosphatasia," Acta Paediatr Scand. Suppl. 360:154-160 (1989).
Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).
Whyte et al., "Asfotase alfa therapy for children with hypophosphatasia," JCI Insight. 1(9):e85971 (2016) (11 pages).
Whyte et al., "Asfotase alfa treatment improves survival for perinatal and infantile hypophosphatasia," J Clin Endocrinol Metab. 101(1):334-42 (2016) (17 pages).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Enzyme-replacement therapy in life-threatening hypophosphatasia," N Engl J Med. 366(10):904-13 (2012).
Whyte et al., "Heritable Forms of Rickets and Osteomalacia," in Connective Tissues and Its Heritable Disorders, pp. 765-787, 2002 (eds. R.M. Royce and B. Steinmann, Wiley-Liss, Inc. Hoboken).
Whyte et al., "Hypophosphatasia," in The Metabolic and Molecular Bases of Inherited Disease (8th ed.), pp. 5313-5329, 2001 (McGraw-Hill Book Company) (epub pp. 1-41).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Whyte et al., "Markedly increased circulating pyridoxal-5'-phosphate levels in hypophosphatasia," J Clin Invest. 76:752-756 (1985).
Whyte et al., "Marrow cell transplantation for infantile hypophosphatasia," J Bone Miner Res. 18(4):624-36 (2003).
Whyte, "Hypophosphatasia: enzyme replacement therapy brings new opportunities and new challenges," J Bone Miner Res. 32(4):667-675 (2017).
Whyte, "Hypophosphatasia and the role of alkaline phosphatase in skeletal mineralization," EndocrRev. 15(4):439-461 (1994).
Whyte, Hypophosphatasia: Nature's window on alkaline phosphatase function in man, *Principles of Bone Biology*, 2nd ed., Bilezikian, Raisz, and Rodan. 2:1229-1248 (2002).
Whyte, "Hypophosphatasia—aetiology, nosology, pathogenesis, diagnosis and treatment," Nat Rev Endocrinol. 12(4):233-46 (2016).
Whyte, "Hypophosphatasia: an overview for 2017," Bone. 102:15-25 (2017).
Wickramasinghe et al., "A case of hypophosphatasia," Ceylon Med J. 48(3):94-5 (2003).
Williams et al., "Solute transport in growth plate cartilage: In vitro and in vivo," Biophys J. 93(3):1039-1050 (2007).
Wroblewski et al., "Pharmacokinetics, metabolic stability, and subcutaneous bioavailability of a genetically engineered analog of DcR3, flint [DcR3(R218Q)], in cynomolgus monkeys and mice," Drug Metab Dispos. 31(4):502-507 (2003).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yamamoto et al., "A successful treatment with pyridoxal phosphate for West syndrome in hypophosphatasia," Pediatr Neurol. 30(3):216-8 (2004).

(56) References Cited

OTHER PUBLICATIONS

Yamamoto et al., "Long term phenotypic correction of severe infantile hypophosphatasia in a mouse model by neonatal injection of lentiviral vector," Mol Ther. 17:S67-S68, Abstract 171 (2009).
Yamamoto et al., "Prolonged survival and phenotypic correction of Akp2(-/-) hypophosphatasia mice by lentiviral gene therapy," J Bone Miner Res. 26(1):135-42 (2011).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Overexpression of CNP in chondrocytes rescues achondroplasia through a MAPK-dependent pathway," Nat Med. 10(1):80-86 (2004).
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in lbab -/- mice," Peptides. 29(9):1575-1581 (2008).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Zierhut et al., "Population PK-PD model for Fc-osteoprotegerin in healthy postmenopausal women," J Pharmacokinet Pharmacodyn. 35:379-399 (2008).
Zurutuza et al., "Correlations of genotype and phenotype in hypophosphatasia," Hum Mol Genet. 8(6):1039-1046 (1999).
International Search Report and Written Opinion for International Patent Application No. PCT/US2018/020859, dated Jun. 19, 2018 (14 pages).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Matsumoto et al., "Rescue of severe infantile hypophosphatasia mice by AAV-mediated sustained expression of soluble alkaline phosphatase," Hum Gene Ther. 22(11):1355-64 (2011).
Hofmann et al., "Clinical aspects of hypophosphatasia: an update," Clinic Rev Bone Miner Metab. 11(2):60-70 (2013).
Taketani et al., "Clinical and genetic aspects of hypophosphatasia in Japanese patients," Arch Dis Child. 99(3):211-5 (2014) (6 pages).
Whyte, "Physiological role of alkaline phosphatase explored in hypophosphatasia," Ann N Y Acad Sci. 1192:190-200 (2010).
Hofmann et al., "Compound heterozygosity of two functional null mutations in the ALPL gene associated with deleterious neurological outcome in an infant with hypophosphatasia," Bone. 55:150-7 (2013).
De Roo et al., "Infantile hypophosphatasia without bone deformities presenting with severe pyridoxine-resistant seizures," Molecular Genetics and Metabolism 111(3):404-7 (2014).
International Search Report and Written Opinion for International Patent Application No. PCT/US2015/064003, dated Mar. 31, 2016 (13 pages).
Lazdunski et al., "Structure-function relationships for some metalloalkaline phosphatases of *E. coli*," Eur J Biochem. 8(4):510-7 (1969).
Bobyr et al., "High-resolution analysis of Zn(2+) coordination in the alkaline phosphatase superfamily by EXAFS and x-ray crystallography," J Mol Biol. 415(1):102-17 (2012).
International Search Report and Written Opinion for International Patent Application No. PCT/US2017/036133, dated Aug. 24, 2017 (10 pages).
International Search Report and Written Opinion for International Patent Application No. PCT/US2018/025206, dated Jul. 3, 2018 (25 pages).

Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
International Search Report and Written Opinion for International Patent Application No. PCT/US2017/025618, dated Jul. 11, 2017 (22 pages).
Li et al., "Standard reference for the six-minute-walk test in healthy children aged 7 to 16 years," Am J Respir Grit Care Med. 176(2):174-80 (2007).
Park et al., "Ex vivo assessment of contractility, fatigability and alternans in isolated skeletal muscles," J Vis Exp. 69:e4198 (2012) (8 pages).
Phillips et al., "FRI-224: Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, San Diego, California, Mar. 5-8, 2015 (1 page).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012).
Sugano et al., "Successful gene therapy in utero for lethal murine hypophosphatasia," Hum Gene Ther. 23(4):399-406 (2012).
International Search Report and Written Opinion for International Patent Application No. PCT/US2015/039973, dated Oct. 5, 2015 (12 pages).
Johnson et al., "Motor proficiency in children with neurofibromatosis type 1," Pediatr Phys Ther. 22(4):344-8 (2010).
Gates et al., "Effects of age, sex, and comorbidities on the pediatric outcomes data collection instrument (PODCI) in the general population," J Pediatr Orthop. 35(2):203-9 (2015).
International Search Report and Written Opinion for International Patent Application No. PCT/US2016/049983, dated Nov. 29, 2016 (12 pages).
International Search Report and Written Opinion for International Patent Application No. PCT/US2016/015366, dated Aug. 9, 2016 (14 pages).
Extended European Search Report for European Application No. 18173111.8, dated Aug. 21, 2018 (9 pages).
Di Rocco et al., "Craniosynostosis and hypophosphatasia," Arch Pediatr. 24(5S2):5S89-5S92 (2017).
Official Action for Russian Patent Application No. 2017123540, dated Jul. 8, 2019 (15 pages).
Whyte et al., "Natural history of perinatal and infantile hypophosphatasia: a retrospective study," J Pediatr. 209:116-124.e4 (2019) (13 pages).
Leung et al., "Outcome of perinatal hypophosphatasia in manitoba mennonites: a retrospective cohort analysis," JIMD Rep. 11:73-78 (2013).
Taketani et al., Chapter 9: Hypophosphatasia. *Human Pathobiochemistry*. T. Oohashi et al. (eds.), 91-100 (2019).
Morrison et al., "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).
Whyte et al., "Asfotase alfa for infants and young children with hypophosphatasia: 7 year outcomes of a single-arm, open-label, phase 2 extension trial," Lancet Diabetes Endocrinol. 7(2):93-105 (2019) (52 pages).
Mornet, "The tissue nonspecific alkaline phosphatase gene mutations database," <http://www.sesep.uvsq.fr/03_hypo_mutations.php>, accessed Oct. 9, 2019 (14 pages).
Hancarova et al., "Hypophosphatasia due to uniparental disomy," Bone. 81:765-766 (2015) (2 pages).
Carden et al., "Tracheomalacia and tracheobronchomalacia in children and adults: an in-depth review," Chest. 127(3):984-1005 (2005).
Murgu et al., "Tracheobronchomalacia and excessive dynamic airway collapse," Respirology. 11(4):388-406 (2006).

(56) References Cited

OTHER PUBLICATIONS

International Preliminary Report on Patentability for International Patent Application No. PCT/US2016/049983, dated Sep. 11, 2018 (9 pages).
Sequence 4, U.S. Appl. No. 12/599,679, Retrieved Nov. 17, 2018 (2 pages).
Agochukwu et al., "Hearing loss in syndromic craniosynostoses: introduction and consideration of mechanisms," available in PMC Aug. 13, 2014, published in final edited form as: Am J Audiol. 23(2): 135-41 (2014) (13 pages).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).
Barcia et al., "Infantile hypophosphatasia: treatment options to control hypercalcemia, hypercalciuria, and chronic bone demineralization," J Pediatr. 130(5):825-8 (1997).
Barvencik et al., "Skeletal mineralization defects in adult hypophosphatasia—a clinical and histological analysis," Osteoporosis Int. 22(10):2667-75 (2011).
Baumgartner-Sigi et al., "Pyridoxine-responsive seizures as the first symptom of infantile hypophosphatasia caused by two novel missense mutations (c.677T>C, p.M226T; c.1112C>T, p.T371l) of the tissue-nonspecific alkaline phosphatase gene," Bone. 40(6):1655-61 (2007).
Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).
Boulet et al., "A population-based study of craniosynostosis in metropolitan Atlanta, 1989-2003," Am J Med Genet A. 146A(8): 984-91 (2008).
Chan et al., "Endoscope-assisted versus open repair of craniosynostosis: a comparison of perioperative cost and risk," J Craniofac Surg. 24(1): 170-4 (2013).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Clarke, "Normal bone anatomy and physiology," Clin J Am Soc Nephrol. 3 Suppl 3: S131-9 (2008).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugia. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-159 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: craniosynostosis," BBA Clin. 6:165-76 (2016).
Khanna et al., "Pictorial essay: The many faces of craniosynostosis," retrieved from <www.ncbi.nlm.nih.gov/pmc/articles/PMC3056371/> on Sep. 10, 2017, Indian J Radiol Imaging. 21(1):49-56 (2011) (8 pages).
Kim et al., "Craniosynostosis: Updates in radiologic diagnosis," J Korean Neurosurg Soc. 59(3):219-26 (2016).
Kozlowski et al., "Hypophosphatasia. Review of 24 Cases," Pediatr Radiol. 5(2):103-17 (1976).
Krakow et al., "Clinical and radiographic delineation of Bent Bone Dysplasia-FGFR2 type or Bent Bone Dysplasia with Distinctive Clavicles and Angel-shaped Phalanges," Am J Med Genet A. 170(10):2652-61 (2016).
Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Millán, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with postoperative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).

(56) References Cited

OTHER PUBLICATIONS

Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988) (12 pages).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c.1559delT in ALPL, a common mutation resulting in the perinatal (lethal) form of hypophosphatasia in Japanese and effects of the mutation on heterozygous carriers," J Hum Genet. 56(2):166-8 (2011).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).
Zaleckas et al., "Diagnosis and treatment of craniosynostosis: Vilnius team experience," Acta Med Litu. 22(2):111-21 (2015).
Anderson, "Mechanism of Mineral Formation in Bone," *Pathology Reviews*. Emanuel Rubin and Ivan Damjanov (eds.), 13-23 (1990).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz and T. John Martin (eds.), 1573-98 (2008).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Del Angel et al., "Birth prevalence estimation of severe Hypophosphatasia in European populations using large-scale protein-coding genetic variation databases," American Society of Human Genetics 66th Annual Meeting, October 18-22, Vancouver, Canada. Poster abstract 1670T (2016) (2 pages).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Simmons, "Best Practices In: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).
Weber et al., "Burden of disease in children with hypophosphatasia: results from patient-reported surveys," 7th International Conference on Children's Bone Health, Jun. 27-30, Salzburg, Austria. *Bone Abstracts*. 4: P119 (2015) (3 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Stoll et al., "Severe hypophosphatasia due to mutations in the tissue-nonspecific alkaline phosphatase (TNSALP) gene," Genet Couns. 13(3):289-95 (2002).
Mornet, "Hypophosphatasia," Best Pract Res Clin Rheumatol. 22(1):113-27 (2008).
Kajdic et al., "Craniosynostosis—Recognition, clinical characteristics, and treatment," Bosn J Basic Med Sci. 18(2):110-6 (2018).
Dortschy et al., "Bevölkerungsbezogene verteilungswerte ausgewählter laborparameter aus der studie zur gesundheit von kindern und jugendlichen in Deutschland (KiGGS)," Robert Koch Institute (2009) (136 pages).
Communication pursuant to Rule 164(2)(b) and Article 94(3) EPC for European Application No. 16707571.2, dated Feb. 26, 2019 (12 pages).
Fong et al., "Hypocalcemia: Updates in diagnosis and management for primary care," Can Fam Physician. 58(2):158-62 (2012).
Makras et al., "Medical treatment of Hypercalcaemia," Hormones. 8(2):83-95 (2009).
Extended European Search Report for European Application No. 15907550.6, dated Jun. 4, 2019 (7 pages).
International Search Report and Written Opinion for International Application No. PCT/US2019/045963, dated Jan. 30, 2020 (26 pages).
Li et al., "Timing of the initiation of bisphosphonates after surgery for fracture healing: a systematic review and meta-analysis of randomized controlled trials," Osteoporos Int. 26(2):431-41 (2015) (11 pages).
Park et al., "The effect of alendronate loaded biphasic calcium phosphate scaffolds on bone regeneration in a rat tibial defect model," Int J Mol Sci. 16(11):26738-53 (2015) (17 pages).
Rodionova et al., "Hypophosphatasia in adults: clinical cases and literature review," Osteoporosis and Bone Diseases. 18(2):25-7 (2015) (4 pages).
Search Report and Translation for Russian Application No. 2018109368, dated Feb. 5, 2020 (4 pages).
Wang et al., "The effects of tissue-non-specific alkaline phosphatase gene therapy on craniosynostosis and craniofacial morphology in the FGFR2C342Y/+ mouse model of Crouzon craniosynostosis," Orthod Craniofac Res. 18 Suppl 1:196-206 (2015).
Whyte et al., "Hypophosphatasia (HPP) in children: enzyme replacement therapy (EzRT) using bone-targeted, tissue-nonspecific alkaline phosphatase (TNSALP)," Ann Neurol. 68(Suppl 14):S70 Abstract WIP-28 (2010) (1 page).
Abrams et al., "Calcium and Vitamin D Requirements of Enterally Fed Preterm Infants," Pediatrics. 131(5): e1676-e1683 (2013) (9 pages).
Kishnani et al., "Hypophosphatasia: enzyme replacement therapy (ENB-0040) decreases TNSALP substrate accumulation and improves functional outcome in affected adolescents and adults," Endocrine Society's 15th International & 14th European Congress of Endocrinology, May 5-9, Florence, Italy. Abstract OC8.1 (2012) (4 pages).
Notice of Reasons for Rejection for Japanese Application No. 2018-508754, dated Jun. 30, 2020 (11 pages).
Phillips et al., "Gait Assessment in Children with Childhood Hypophosphatasia: Impairments in Muscle Strength and Physical Function," The Endocrine Society's 97th Annual Meeting & Expo, Mar. 5-8, San Diego, CA (2015) (2 pages).
Communication pursuant to Article 94(3) EPC for European Patent Application No. 16739617.5, dated May 11, 2020 (10 pages).
Rodionova et al., "Hypophosphatasia in Adults: Clinical Cases and Literature Review," Osteoporosis and Bone Diseases. 18(2):25-28 (2015) 10.14341/osteo2015225-28 (English language abstract).
Office Action for Russian Patent Application No. 2018137822, dated Jul. 24, 2020 (20 pages).
Bishop et al., "Life-threatening hypophosphatasia (HPP): Results of up to two years bone-targeted Enzyme Replacement Therapy (ERT) in infants and young children," Bone. 48:S82 (2011) (1 page) (Abstract only).

(56) References Cited

OTHER PUBLICATIONS

Kim et al., "Comparison of phenylketonuria (PKU) patients' height, weight and body mass index (BMI) to the general population," Mol Genet Metab. 105:328-329 (2012).

Whyte et al., "Treatment of children with hypophosphatasia (HPP) with ENB-0040: radiographic and DXA outcomes after 6 months of therapy," Horm Res Paediatr. 76(Suppl 2):26 (2011) (Abstract only).

Notice of Reasons for Rejection for Japanese Patent Application No. 2018-515934, dated Jul. 28, 2020 (7 pages).

Dbfetch, "Bone targeted alkaline phosphatase, kits and methods of use thereof," Database No. Hl520929, last updated Nov. 2, 2010 (1 page).

Fu-Hang et al., "Preliminary study on the effect of $Zn^{2+}$ on the activities of peptidase and alkaline phosphatase," Marine Sciences. 27(3):64-65 (2003) (Abstract only).

Office Action for Chinese Patent Application No. 201680048588.5, dated Jan. 18, 2021 (28 pages).

Dutta et al., "Men and mice: Relating their ages," Life Sci. 152:244-8 (2016) (5 pages).

Zhang et al., "Engineering E. coli Alkaline Phosphatase Yields Changes of Catalytic Activity, Thermal Stability and Phosphate Inhibition," Biocatal Biotransfor. 20(6):381-389 (2002).

Nangia et al., "Disorders of Calcium Metabolism in Newborns," Journal of Neonatology. 17(2):43-49 (2003).

Kochanowski et al., "Medium and feed optimization for fed-batch production of a monoclonal antibody in CHO cells," BMC Proc. 5(Suppl 8):P75 (2011) (3 pages).

"Data file 29-0929-25 AA. Xcellerex™ XDR cell culture bioreactor systems," GE Healthcare Life Sciences, published Feb. 2014 (4 pages).

Yagasaki et al., "Animal Cell Technology: Basic & Applied Aspects," Proceedings of the Fifteenth Annual Meeting of the Japanese Association for Animal Cell Technology (JAACT), vol. 13, Fuchu, Nov. 11-15, 2002 (461 pages).

Kozlenkov et al., "Residues determining the binding specificity of uncompetitive inhibitors to tissue-nonspecific alkaline phosphatase," J Bone Miner Res. 19(11):1862-72 (2004).

NCBI Protein Database Accession No. NM_000478.2, retrieved on Feb. 23, 2021 (7 pages).

Pradhan et al., "Exposure-Response Modeling and Simulation to Support Evaluation of Efficacious and Safe Exposure and Dose Range for Asfotase alfa in Patients with Hypophosphatasia," ASBMR 2015 Annual Meeting Abstracts. J Bone and Med Res. SU0380:S316 (2015) (1 page).

Abbruzzese, "The Tinetti Performance-Oriented Mobility Assessment Tool," Am J Nursing. 98(12):16J-16L (1998) (3 pages).

International Search Report and Written Opinion for International Patent Application No. PCT/US20/64140, dated Apr. 23, 2021 (70 pages).

Kishnani et al., "Five-year efficacy and safety of asfotase alfa therapy for adults and adolescents with hypophosphatasia," Bone. 121:149-162 (2019).

Alexion Pharmaceuticals, "Safety Study of Human Recombinant Tissue Non-Specific Alkaline Phosphatase Fusion Protein Asfotase Alfa in Adults With Hypophosphatasia (HPP)," ClinicalTrials.gov. NCT00739505, <https://www.clinicaltrials.gov/ct2/show/NCT00739505>, last updated Mar. 29, 2019 (8 pages).

Alexion Pharmaceuticals, "Safety and Efficacy Study of Asfotase Alfa in Adolescents and Adults With Hypophosphatasia (HPP)," ClinicalTrials.gov. NCT01163149, <https://clinicaltrials.gov/ct2/show/NCT01163149>, last updated Mar. 13, 2019 (9 pages).

Alexion Pharmaceuticals, "Strensiq (asfotase alfa) for injection," retrieved from <globalgenes.org/2015/11/05/alexion-announces-fda-approval-for--strensiq/?gclid=CjwKCAjwwqaGBhBKEiwAMk-FtFQOKvuVN-WmNcDVyu9Q9X3f6QB-V0Two0x216TR2H4_Qc6jSlhvxoCiLMQAvD_BwE>, dated Nov. 5, 2015 (1 page).

European Medicines Agency, "Strensiq: Asfotase Alfa," <www.ema.europa.eu/en/medicines/human/EPAR/strensiq>, last updated Mar. 25, 2021 (8 pages).

Hofmann et al., "Efficacy and safety of asfotase alfa in infants and young children with hypophosphatasia: a phase 2 open-label study," J Clin Endocrinol Metab. 104(7): 2735-2747 (2019) (14 pages).

Examination Report No. 1 for Australian Patent Application No. 2016308624, dated Aug. 27, 2021 (6 pages).

Kim et al., "CHO cells in biotechnology for production of recombinant proteins: current state and further potential," Appl Microbiol Biotechnol. 93(3):917-30 (2012).

Office Action for Chinese Patent Application No. 201780021666.7, issued Jul. 21, 2021 (34 pages).

McCormack et al., "Is bigger better? An argument for very low starting doses," CMAJ. 183(1):65-9 (2011).

Rush, "Childhood hypophosphatasia: to treat or not to treat," Orphanet J Rare Dis. 13(1):116(2018) (5 pages).

Phillips et al., "Clinical Outcome Assessments: Use of Normative Data in a Pediatric Rare Disease," Value Health. 21(5):508-514 (2018).

Office Action for Japanese Patent Application No. 2018-551309, dated Nov. 2, 2021 (11 pages).

Office Action for Russian Patent Application No. 2019134794, dated on Dec. 7, 2021 (11 pages).

Examination Report for Canadian Patent Application No. 2,967,851, dated Dec. 21, 2021 (4 pages).

Communication pursuant to Article 94(3) EPC for European Patent Application No. 16852428.8, dated Dec. 8, 2021 (4 pages).

"Scale-up of CHO fed-batch cultures in HyClone (TM) ActiPro (TM) medium supplemented with Cell Boost (TM) 7a and 7b," GE Healthcare Bio-Sciences AB, dated Sep. 2016 (4 pages).

Decision on Rejection for Chinese Patent Application No. 201680048588.5, dated Jan. 20, 2022 (19 pages).

Communication pursuant to Article 94(3) EPC for European Patent Application No. 16758322.8, dated Jan. 25, 2022 (3 pages). .

\* cited by examiner

SEQUENCE LISTING

```
<160> NUMBER OF SEQ ID NOS: 20

<210> SEQ ID NO 1
<211> LENGTH: 524
<212> TYPE: PRT
<213> ORGANISM: Homo sapiens

<400> SEQUENCE: 1

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
```

```
            35                  40                  45
Asn Val Ala Lys Asn Val Ile Met Phe Leu Gly Asp Gly Met Gly Val
             50                  55                  60

Ser Thr Val Thr Ala Ala Arg Ile Leu Lys Gly Gln Leu His His Asn
 65                  70                  75                  80

Pro Gly Glu Glu Thr Arg Leu Glu Met Asp Lys Phe Pro Phe Val Ala
                 85                  90                  95

Leu Ser Lys Thr Tyr Asn Thr Asn Ala Gln Val Pro Asp Ser Ala Gly
                100                 105                 110

Thr Ala Thr Ala Tyr Leu Cys Gly Val Lys Ala Asn Glu Gly Thr Val
                115                 120                 125

Gly Val Ser Ala Ala Thr Glu Arg Ser Arg Cys Asn Thr Thr Gln Gly
                130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
                195                 200                 205

Met His Asn Ile Arg Asp Ile Asp Val Ile Met Gly Gly Gly Arg Lys
                210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
                260                 265                 270

Thr Glu Leu Leu Thr Leu Asp Pro His Asn Val Asp Tyr Leu Leu Gly
                275                 280                 285

Leu Phe Glu Pro Gly Asp Met Gln Tyr Glu Leu Asn Arg Asn Asn Val
                290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
                355                 360                 365

Glu Asp Thr Leu Thr Val Val Thr Ala Asp His Ser His Val Phe Thr
                370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
                435                 440                 445

Leu Arg His Glu Thr His Gly Gly Glu Asp Val Ala Val Phe Ser Lys
                450                 455                 460
```

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
        515                 520

<210> SEQ ID NO 2
<211> LENGTH: 524
<212> TYPE: PRT
<213> ORGANISM: Homo sapiens

<400> SEQUENCE: 2

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg His Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Val Ala Ile Gln Ile Leu

-continued

```
                305                 310                 315                 320
Arg Lys Asn Pro Lys Gly Phe Phe Leu Leu Val Glu Gly Arg Ile
            325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
            450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
            515                 520

<210> SEQ ID NO 3
<211> LENGTH: 524
<212> TYPE: PRT
<213> ORGANISM: Homo sapiens

<400> SEQUENCE: 3

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160
```

```
Val Gly Ile Val Thr Thr Arg Val Asn His Ala Thr Pro Ser Ala
            165                 170                 175

Ala Tyr Ala His Ser Ala Asp Arg Asp Trp Tyr Ser Asp Asn Glu Met
        180                 185                 190

Pro Pro Glu Ala Leu Ser Gln Gly Cys Lys Asp Ile Ala Tyr Gln Leu
            195                 200                 205

Met His Asn Ile Arg Asp Ile Asp Val Ile Met Gly Gly Gly Arg Lys
        210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
            245                 250                 255

Lys Ser Phe Lys Pro Arg Tyr Lys His Ser His Phe Ile Trp Asn Arg
        260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
        290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
            325                 330                 335

Asp His Gly His His Glu Gly Lys Ala Lys Gln Ala Leu His Glu Ala
        340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
            405                 410                 415

Asn Gly Pro Gly Tyr Lys Val Val Gly Gly Glu Arg Glu Asn Val Ser
        420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
            485                 490                 495

Cys Ala Pro Ala Ser Ser Ala Gly Ser Leu Ala Ala Gly Pro Leu Leu
        500                 505                 510

Leu Ala Leu Ala Leu Tyr Pro Leu Ser Val Leu Phe
            515                 520

<210> SEQ ID NO 4
<211> LENGTH: 524
<212> TYPE: PRT
<213> ORGANISM: Homo sapiens

<400> SEQUENCE: 4

Met Ile Ser Pro Phe Leu Val Leu Ala Ile Gly Thr Cys Leu Thr Asn
1               5                   10                  15
```

-continued

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
 50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Ser Ala Gly
            100                 105                 110

Thr Ala Thr Ala Tyr Leu Cys Gly Val Lys Ala Asn Glu Gly Thr Val
            115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
            195                 200                 205

Met His Asn Ile Arg Asp Ile Asp Val Ile Met Gly Gly Gly Arg Lys
            210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

-continued

```
Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 5
<211> LENGTH: 524
<212> TYPE: PRT
<213> ORGANISM: Homo sapiens

<400> SEQUENCE: 5

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg His Lys His Ser His Phe Ile Trp Asn Arg
            260                 265                 270

Thr Glu Leu Leu Thr Leu Asp Pro His Asn Val Asp Tyr Leu Leu Gly
        275                 280                 285
```

Leu Phe Glu Pro Gly Asp Met Gln Tyr Glu Leu Asn Arg Asn Asn Val
            290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
            370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
            450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 6
<211> LENGTH: 652
<212> TYPE: PRT
<213> ORGANISM: Macaca mulatta

<400> SEQUENCE: 6

Met Pro Thr Val Lys Thr Lys Gln Glu Ser His Ala Gly Ser Gly Ser
1               5                   10                  15

Gly Pro Arg Leu Ala Glu Arg Lys Gly Arg Val Gly Ala Ala Arg Arg
                20                  25                  30

Gln Ser Pro Arg Ala Pro Gly Gly Leu Pro Gly Pro Arg Ser Gly
            35                  40                  45

Pro Ala Ala Ala Phe Ile Arg Arg Arg Gly Arg Trp Pro Gly Pro Arg
50                  55                  60

Cys Ala Pro Ala Thr Pro Arg Pro Arg Ser Arg Leu Cys Ala Pro Thr
65                  70                  75                  80

Arg Leu Cys Leu Asp Glu Pro Ser Ser Val Leu Cys Ala Gly Leu Glu
                85                  90                  95

His Gln Leu Thr Ser Asp His Cys Gln Pro Thr Pro Ser His Pro Arg
                100                 105                 110

Arg Ser His Leu Trp Ala Ser Gly Ile Lys Gln Val Leu Gly Cys Thr
            115                 120                 125

Met Ile Ser Pro Phe Leu Val Leu Ala Ile Gly Thr Cys Leu Thr Asn

```
            130             135             140
Ser Leu Val Pro Glu Lys Glu Lys Asp Pro Lys Tyr Trp Arg Asp Gln
145                 150                 155                 160

Ala Gln Glu Thr Leu Lys Tyr Ala Leu Glu Leu Gln Lys Leu Asn Thr
            165                 170                 175

Asn Val Ala Lys Asn Val Ile Met Phe Leu Gly Asp Gly Met Gly Val
                180                 185                 190

Ser Thr Val Thr Ala Thr Arg Ile Leu Lys Gly Gln Leu His His Asn
            195                 200                 205

Pro Gly Glu Glu Thr Arg Leu Glu Met Asp Lys Phe Pro Phe Val Ala
        210                 215                 220

Leu Ser Lys Thr Tyr Asn Thr Asn Ala Gln Val Pro Asp Ser Ala Gly
225                 230                 235                 240

Thr Ala Thr Ala Tyr Leu Cys Gly Val Lys Ala Asn Glu Gly Thr Val
            245                 250                 255

Gly Val Ser Ala Ala Thr Glu Arg Ser Arg Cys Asn Thr Thr Gln Gly
                260                 265                 270

Asn Glu Val Thr Ser Ile Leu Arg Trp Ala Lys Asp Ala Gly Lys Ser
            275                 280                 285

Val Gly Ile Val Thr Thr Thr Arg Val Asn His Ala Thr Pro Ser Ala
        290                 295                 300

Ala Tyr Ala His Ser Ala Asp Arg Asp Trp Tyr Ser Asp Asn Glu Met
305                 310                 315                 320

Pro Pro Glu Ala Leu Ser Gln Gly Cys Lys Asp Ile Ala Tyr Gln Leu
            325                 330                 335

Val His Asn Ile Arg Asp Ile Asp Val Ile Met Gly Gly Gly Arg Lys
                340                 345                 350

Tyr Met Tyr Pro Lys Asn Lys Thr Asp Val Glu Tyr Glu Ile Asp Glu
            355                 360                 365

Lys Ala Arg Gly Thr Arg Leu Asp Gly Leu Asp Leu Val Asn Ile Trp
370                 375                 380

Lys Ser Phe Lys Pro Arg His Lys His Ser His Phe Ile Trp Asn Arg
385                 390                 395                 400

Thr Glu Leu Leu Thr Leu Asp Pro His Asn Val Asp Tyr Leu Leu Gly
            405                 410                 415

Leu Phe Glu Pro Gly Asp Met Glu Tyr Glu Leu Asn Arg Asn Asn Val
                420                 425                 430

Thr Asp Pro Ser Leu Ser Glu Met Val Val Ala Ile Gln Ile Leu
            435                 440                 445

Arg Lys Asn Pro Lys Gly Phe Phe Leu Leu Val Glu Gly Gly Arg Ile
450                 455                 460

Asp His Gly His His Glu Gly Lys Ala Lys Gln Ala Leu His Glu Ala
465                 470                 475                 480

Val Glu Met Asp Arg Ala Ile Gly Gln Ala Gly Ser Met Thr Ser Leu
            485                 490                 495

Glu Asp Thr Leu Thr Val Val Thr Ala Asp His Ser His Val Phe Thr
                500                 505                 510

Phe Gly Gly Tyr Thr Pro Arg Gly Asn Ser Ile Phe Gly Leu Ala Pro
            515                 520                 525

Met Leu Ser Asp Thr Asp Lys Lys Pro Phe Thr Ala Ile Leu Tyr Gly
        530                 535                 540

Asn Gly Pro Gly Tyr Lys Val Val Gly Gly Glu Arg Glu Asn Val Ser
545                 550                 555                 560
```

Met Val Asp Tyr Ala His Asn Tyr Gln Ala Gln Ser Ala Val Pro
              565                 570                 575

Leu Arg His Glu Thr His Gly Gly Glu Asp Val Ala Val Phe Ser Lys
            580                 585                 590

Gly Pro Met Ala His Leu Leu His Gly Val His Glu Gln Asn Tyr Ile
            595                 600                 605

Pro His Val Met Ala Tyr Ala Ala Cys Ile Gly Ala Asn Leu Asp His
        610                 615                 620

Cys Ala Pro Ala Ser Ser Ala Gly Ser Leu Ala Ala Gly Pro Leu Leu
625                 630                 635                 640

Leu Pro Leu Ala Leu Phe Pro Leu Ser Ile Leu Phe
            645                 650

<210> SEQ ID NO 7
<211> LENGTH: 524
<212> TYPE: PRT
<213> ORGANISM: Rattus norvegicus

<400> SEQUENCE: 7

Met Ile Leu Pro Phe Leu Val Leu Ala Ile Gly Pro Cys Leu Thr Asn
1               5                   10                  15

Ser Phe Val Pro Glu Lys Glu Lys Asp Pro Ser Tyr Trp Arg Gln Gln
            20                  25                  30

Ala Gln Glu Thr Leu Lys Asn Ala Leu Lys Leu Gln Lys Leu Asn Thr
        35                  40                  45

Asn Val Ala Lys Asn Ile Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Thr Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Thr Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Arg Pro Glu Ala Leu Ser Gln Gly Cys Lys Asp Ile Ala Tyr Gln Leu
        195                 200                 205

Met His Asn Ile Lys Asp Ile Asp Val Ile Met Gly Gly Gly Arg Lys
    210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
                245                 250                 255

Lys Ser Phe Lys Pro Arg His Lys His Ser His Tyr Val Trp Asn Arg
            260                 265                 270

Thr Glu Leu Leu Ala Leu Asp Pro Ser Arg Val Asp Tyr Leu Leu Gly

```
            275                 280                 285

Leu Phe Glu Pro Gly Asp Met Gln Tyr Glu Leu Asn Arg Asn Asn Leu
    290                 295                 300

Thr Asp Pro Ser Leu Ser Glu Met Val Glu Val Ala Leu Arg Ile Leu
305                 310                 315                 320

Thr Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Glu Ala Ile Gly Lys Ala Gly Thr Met Thr Ser Gln
        355                 360                 365

Lys Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                485                 490                 495

Cys Ala Trp Ala Ser Ser Ala Ser Ser Pro Ser Pro Gly Ala Leu Leu
            500                 505                 510

Leu Pro Leu Ala Leu Phe Pro Leu Arg Thr Leu Phe
        515                 520

<210> SEQ ID NO 8
<211> LENGTH: 502
<212> TYPE: PRT
<213> ORGANISM: Canis lupus familiaris

<400> SEQUENCE: 8

Glu Lys Asp Pro Lys Tyr Trp Arg Asp Gln Ala Gln Gln Thr Leu Lys
1               5                   10                  15

Tyr Ala Leu Arg Leu Gln Asn Leu Asn Thr Asn Val Ala Lys Asn Val
            20                  25                  30

Ile Met Phe Leu Gly Asp Gly Met Gly Val Ser Thr Val Thr Ala Thr
        35                  40                  45

Arg Ile Leu Lys Gly Gln Leu His His Asn Pro Gly Glu Glu Thr Arg
    50                  55                  60

Leu Glu Met Asp Lys Phe Pro Tyr Val Ala Leu Ser Lys Thr Tyr Asn
65                  70                  75                  80

Thr Asn Ala Gln Val Pro Asp Ser Ala Gly Thr Ala Thr Ala Tyr Leu
                85                  90                  95

Cys Gly Val Lys Ala Asn Glu Gly Thr Val Gly Val Ser Ala Ala Thr
            100                 105                 110

Gln Arg Thr His Cys Asn Thr Thr Gln Gly Asn Glu Val Thr Ser Ile
        115                 120                 125
```

```
Leu Arg Trp Ala Lys Asp Ala Gly Lys Ser Val Gly Ile Val Thr Thr
130                 135                 140

Thr Arg Val Asn His Ala Thr Pro Ser Ala Ala Tyr Ala His Ser Ala
145                 150                 155                 160

Asp Arg Asp Trp Tyr Ser Asp Asn Glu Met Pro Pro Glu Ala Leu Ser
                165                 170                 175

Gln Gly Cys Lys Asp Ile Ala Tyr Gln Leu Met His Asn Val Lys Asp
            180                 185                 190

Ile Glu Val Ile Met Gly Gly Arg Lys Tyr Met Phe Pro Lys Asn
        195                 200                 205

Arg Thr Asp Val Glu Tyr Glu Met Asp Glu Lys Ser Thr Gly Ala Arg
210                 215                 220

Leu Asp Gly Leu Asn Leu Ile Asp Ile Trp Lys Asn Phe Lys Pro Arg
225                 230                 235                 240

His Lys His Ser His Tyr Val Trp Asn Arg Thr Glu Leu Leu Ala Leu
                245                 250                 255

Asp Pro Tyr Thr Val Asp Tyr Leu Leu Gly Leu Phe Asp Pro Gly Asp
                260                 265                 270

Met Gln Tyr Glu Leu Asn Arg Asn Asn Val Thr Asp Pro Ser Leu Ser
            275                 280                 285

Glu Met Val Glu Ile Ala Ile Lys Ile Leu Ser Lys Lys Pro Arg Gly
290                 295                 300

Phe Phe Leu Leu Val Glu Gly Gly Arg Ile Asp His Gly His His Glu
305                 310                 315                 320

Gly Lys Ala Lys Gln Ala Leu His Glu Ala Val Glu Met Asp Arg Ala
                325                 330                 335

Ile Gly Lys Ala Gly Val Met Thr Ser Leu Glu Asp Thr Leu Thr Val
            340                 345                 350

Val Thr Ala Asp His Ser His Val Phe Thr Phe Gly Gly Tyr Thr Pro
                355                 360                 365

Arg Gly Asn Ser Ile Phe Gly Leu Ala Pro Met Val Ser Asp Thr Asp
370                 375                 380

Lys Lys Pro Phe Thr Ala Ile Leu Tyr Gly Asn Gly Pro Gly Tyr Lys
385                 390                 395                 400

Val Val Gly Gly Glu Arg Glu Asn Val Ser Met Val Asp Tyr Ala His
                405                 410                 415

Asn Asn Tyr Gln Ala Gln Ser Ala Val Pro Leu Arg His Glu Thr His
            420                 425                 430

Gly Gly Glu Asp Val Ala Val Phe Ala Lys Gly Pro Met Ala His Leu
        435                 440                 445

Leu His Gly Val His Glu Gln Asn Tyr Ile Pro His Val Met Ala Tyr
450                 455                 460

Ala Ala Cys Ile Gly Ala Asn Gln Asp His Cys Ala Ser Ala Ser Ser
465                 470                 475                 480

Ala Gly Gly Pro Ser Pro Gly Pro Leu Leu Leu Leu Ala Leu Leu
                485                 490                 495

Pro Val Gly Ile Leu Phe
            500

<210> SEQ ID NO 9
<211> LENGTH: 252
<212> TYPE: PRT
<213> ORGANISM: Sus scrofa

<400> SEQUENCE: 9
```

Ala Glu Leu Leu Ala Leu Asp Pro His Thr Val Asp Tyr Leu Leu Gly
1               5                   10                  15

Leu Phe Glu Pro Gly Asp Met Gln Tyr Glu Leu Asn Arg Asn Asn Val
                20                  25                  30

Thr Asp Pro Ser Leu Ser Glu Met Val Glu Met Ala Ile Arg Ile Leu
            35                  40                  45

Ile Lys Asn Pro Lys Gly Phe Phe Leu Leu Val Glu Gly Gly Arg Ile
50                  55                  60

Asp His Gly His His Glu Gly Lys Ala Lys Gln Ala Leu His Glu Ala
65                  70                  75                  80

Val Glu Met Asp Arg Ala Ile Glu Gln Ala Gly Ser Met Thr Ser Val
                85                  90                  95

Glu Asp Thr Leu Thr Val Val Thr Ala Asp His Ser His Val Phe Thr
            100                 105                 110

Phe Gly Gly Tyr Thr Pro Arg Gly Asn Ser Ile Phe Gly Leu Ala Pro
        115                 120                 125

Met Val Ser Asp Thr Asp Lys Lys Pro Phe Thr Ala Ile Leu Tyr Gly
    130                 135                 140

Asn Gly Pro Gly Tyr Lys Val Val Gly Gly Glu Arg Glu Asn Val Ser
145                 150                 155                 160

Met Val Asp Tyr Ala His Asp Asn Tyr Gln Ala Gln Ser Ala Val Pro
                165                 170                 175

Leu Arg His Glu Thr His Gly Gly Glu Asp Val Ala Ile Phe Ala Arg
            180                 185                 190

Gly Pro Met Ala His Leu Leu His Gly Val His Glu Gln Asn Tyr Ile
        195                 200                 205

Pro His Val Met Ala Tyr Ala Ala Cys Val Gly Ala Asn Arg Asp His
    210                 215                 220

Cys Ala Ser Ala Ser Ser Gly Ser Pro Ser Pro Gly Pro Leu Leu
225                 230                 235                 240

Leu Leu Leu Ala Leu Leu Pro Leu Gly Ile Leu Phe
            245                 250

<210> SEQ ID NO 10
<211> LENGTH: 524
<212> TYPE: PRT
<213> ORGANISM: Mus musculus

<400> SEQUENCE: 10

Met Ile Ser Pro Phe Leu Val Leu Ala Ile Gly Thr Cys Leu Thr Asn
1               5                   10                  15

Ser Phe Val Pro Glu Lys Glu Arg Asp Pro Ser Tyr Trp Arg Gln Gln
                20                  25                  30

Ala Gln Glu Thr Leu Lys Asn Ala Leu Lys Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Thr Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val

```
            115                 120                 125
Gly Val Ser Ala Ala Thr Glu Arg Thr Arg Cys Asn Thr Thr Gln Gly
            130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Asp Val Ile Met Gly Gly Gly Arg Lys
    210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
                245                 250                 255

Lys Ser Phe Lys Pro Arg His Lys His Ser His Tyr Val Trp Asn Arg
            260                 265                 270

Thr Glu Leu Leu Ala Leu Asp Pro Ser Arg Val Asp Tyr Leu Leu Gly
        275                 280                 285

Leu Phe Glu Pro Gly Asp Met Gln Tyr Glu Leu Asn Arg Asn Asn Leu
    290                 295                 300

Thr Asp Pro Ser Leu Ser Glu Met Val Glu Val Ala Leu Arg Ile Leu
305                 310                 315                 320

Thr Lys Asn Leu Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Lys Ala Gly Ala Met Thr Ser Gln
        355                 360                 365

Lys Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                485                 490                 495

Cys Ala Trp Ala Gly Ser Gly Ser Ala Pro Ser Pro Gly Ala Leu Leu
            500                 505                 510

Leu Pro Leu Ala Val Leu Ser Leu Arg Thr Leu Phe
        515                 520

<210> SEQ ID NO 11
```

```
<211> LENGTH: 524
<212> TYPE: PRT
<213> ORGANISM: Bos taurus

<400> SEQUENCE: 11

Met Ile Ser Pro Phe Leu Leu Leu Ala Ile Gly Thr Cys Phe Ala Ser
1               5                   10                  15

Ser Leu Val Pro Glu Lys Glu Lys Asp Pro Lys Tyr Trp Arg Asp Gln
                20                  25                  30

Ala Gln Gln Thr Leu Lys Asn Ala Leu Arg Leu Gln Thr Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Ser
65                  70                  75                  80

Pro Gly Glu Glu Thr Lys Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Ser Gln Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Glu Val Ile Met Gly Gly Gly Arg Lys
    210                 215                 220

Tyr Met Phe Pro Lys Asn Arg Thr Asp Val Glu Tyr Glu Leu Asp Glu
225                 230                 235                 240

Lys Ala Arg Gly Thr Arg Leu Asp Gly Leu Asn Leu Ile Asp Ile Trp
                245                 250                 255

Lys Ser Phe Lys Pro Lys His Lys His Ser His Tyr Val Trp Asn Arg
            260                 265                 270

Thr Asp Leu Leu Ala Leu Asp Pro His Ser Val Asp Tyr Leu Leu Gly
        275                 280                 285

Leu Phe Glu Pro Gly Asp Met Gln Tyr Glu Leu Asn Arg Asn Asn Ala
    290                 295                 300

Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Gln Ala Gly Ala Met Thr Ser Val
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
```

```
                385                 390                 395                 400
        Met Val Ser Asp Thr Asp Lys Lys Pro Phe Thr Ala Ile Leu Tyr Gly
                        405                 410                 415

Asn Gly Pro Gly Tyr Lys Val Val Gly Gly Glu Arg Glu Asn Val Ser
                    420                 425                 430

Met Val Asp Tyr Ala His Asn Asn Tyr Gln Ala Gln Ser Ala Val Pro
                    435                 440                 445

Leu Arg His Glu Thr His Gly Gly Asp Val Ala Val Phe Ala Lys
                    450                 455                 460

Gly Pro Met Ala His Leu Leu His Gly Val His Glu Gln Asn Tyr Ile
        465                 470                 475                 480

Pro His Val Met Ala Tyr Ala Ala Cys Ile Gly Ala Asn Arg Asp His
                        485                 490                 495

Cys Ala Ser Ala Ser Ser Ser Gly Ser Pro Ser Pro Gly Pro Leu Leu
                    500                 505                 510

Leu Leu Leu Ala Leu Leu Pro Leu Gly Ser Leu Phe
                    515                 520

<210> SEQ ID NO 12
<211> LENGTH: 524
<212> TYPE: PRT
<213> ORGANISM: Bos taurus

<400> SEQUENCE: 12

Met Ile Ser Pro Phe Leu Leu Ala Ile Gly Thr Cys Phe Ala Ser
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Thr Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Ser
65                  70                  75                  80

Pro Gly Glu Glu Thr Lys Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Ser Gln Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Glu Val Ile Met Gly Gly Gly Arg Lys
    210                 215                 220

Tyr Met Phe Pro Lys Asn Arg Thr Asp Val Glu Tyr Glu Leu Asp Glu
225                 230                 235                 240
```

```
Lys Ala Arg Gly Thr Arg Leu Asp Gly Leu Asn Leu Ile Asp Ile Trp
                245                 250                 255
Lys Ser Phe Lys Pro Lys His Lys His Ser His Tyr Val Trp Asn Arg
            260                 265                 270
Thr Asp Leu Leu Ala Leu Asp Pro His Ser Val Asp Tyr Leu Leu Gly
        275                 280                 285
Leu Phe Glu Pro Gly Asp Met Gln Tyr Glu Leu Asn Arg Asn Asn Ala
    290                 295                 300
Thr Asp Pro Ser Leu Ser Glu Met Val Glu Met Ala Ile Arg Ile Leu
305                 310                 315                 320
Asn Lys Asn Pro Lys Gly Phe Phe Leu Leu Val Glu Gly Gly Arg Ile
                325                 330                 335
Asp His Gly His His Glu Gly Lys Ala Lys Gln Ala Leu His Glu Ala
            340                 345                 350
Val Glu Met Asp Gln Ala Ile Gly Gln Ala Gly Ala Met Thr Ser Val
        355                 360                 365
Glu Asp Thr Leu Thr Val Val Thr Ala Asp His Ser His Val Phe Thr
    370                 375                 380
Phe Gly Gly Tyr Thr Pro Arg Gly Asn Ser Ile Phe Gly Leu Ala Pro
385                 390                 395                 400
Met Val Ser Asp Thr Asp Lys Lys Pro Phe Thr Ala Ile Leu Tyr Gly
                405                 410                 415
Asn Gly Pro Gly Tyr Lys Val Val Gly Glu Arg Glu Asn Val Ser
            420                 425                 430
Met Val Asp Tyr Ala His Asn Asn Tyr Gln Ala Gln Ser Ala Val Pro
        435                 440                 445
Leu Arg His Glu Thr His Gly Gly Glu Asp Val Ala Val Phe Ala Lys
    450                 455                 460
Gly Pro Met Ala His Leu Leu His Gly Val His Glu Gln Asn Tyr Ile
465                 470                 475                 480
Pro His Val Met Ala Tyr Ala Ala Cys Ile Gly Ala Asn Arg Asp His
                485                 490                 495
Cys Ala Ser Ala Ser Ser Ser Gly Ser Pro Ser Pro Gly Pro Leu Leu
            500                 505                 510
Leu Leu Leu Ala Leu Leu Pro Leu Gly Ser Leu Phe
        515                 520

<210> SEQ ID NO 13
<211> LENGTH: 124
<212> TYPE: PRT
<213> ORGANISM: Bos taurus

<400> SEQUENCE: 13

Asp Pro Lys Tyr Trp Arg Asp Gln Ala Gln Gln Thr Leu Lys Asn Ala
1               5                   10                  15
Leu Gly Leu Gln Lys Leu Asn Thr Lys Val Ala Lys Asn Val Ile Leu
            20                  25                  30
Phe Leu Gly Asp Gly Met Gly Val Ser Thr Val Thr Ala Ala Arg Ile
        35                  40                  45
Leu Lys Gly Gln Leu His His Asn Pro Gly Glu Glu Thr Arg Leu Glu
    50                  55                  60
Met Asp Lys Phe Pro Phe Val Ala Leu Ser Lys Thr Tyr Asn Thr Asn
65                  70                  75                  80
Ala Gln Val Pro Asp Ser Ala Gly Thr Ala Pro His Pro Val Arg Val
                85                  90                  95
```

Lys Ala Met Arg Ala Pro Trp Gly Glu Pro His Gln Arg Gln Cys Asn
            100                 105                 110

Thr Arg Arg Ala Thr Ser Thr His Leu Leu Ala Gly
            115                 120

<210> SEQ ID NO 14
<211> LENGTH: 524
<212> TYPE: PRT
<213> ORGANISM: Felis catus

<400> SEQUENCE: 14

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Lys Leu Asn Thr
            35                  40                  45

Asn Val Val Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
            115                 120                 125

Gly Val Ser Ala Ala Thr Gln Arg Thr Gln Cys Asn Thr Thr Gln Gly
    130                 135                 140

Asn Glu Val Thr Ser Ile Leu Arg Trp Ala Lys Asp Ser Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
            195                 200                 205

Met His Asn Val Arg Asp Ile Glu Val Ile Met Gly Gly Gly Arg Lys
    210                 215                 220

Tyr Met Phe Pro Lys Asn Arg Thr Asp Val Glu Tyr Glu Met Asp Glu
225                 230                 235                 240

Lys Ala Arg Gly Thr Arg Leu Asp Gly Leu Asn Leu Val Asp Ile Trp
                245                 250                 255

Lys Ser Phe Lys Pro Arg His Lys His Ser His Tyr Val Trp Asn Arg
            260                 265                 270

Thr Glu Leu Leu Thr Leu Asp Pro Tyr Gly Val Asp Tyr Leu Leu Gly
            275                 280                 285

Leu Phe Glu Pro Gly Asp Met Gln Tyr Glu Leu Asn Arg Asn Ser Thr
    290                 295                 300

Thr Asp Pro Ser Leu Ser Glu Met Val Glu Ile Ala Ile Lys Ile Leu
305                 310                 315                 320

Ser Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala

```
              340                 345                 350
Val Glu Met Asp Gln Ala Ile Gly Arg Ala Gly Ala Met Thr Ser Val
        355                 360                 365

Glu Asp Thr Leu Thr Ile Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ser Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ala Lys
        450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Leu Asp His
                485                 490                 495

Cys Ala Ser Ala Ser Ser Ala Gly Gly Pro Ser Pro Gly Pro Leu Phe
                500                 505                 510

Leu Leu Leu Ala Leu Pro Ser Leu Gly Ile Leu Phe
            515                 520

<210> SEQ ID NO 15
<211> LENGTH: 532
<212> TYPE: PRT
<213> ORGANISM: Homo sapiens

<400> SEQUENCE: 15

Met Gln Gly Pro Trp Val Leu Leu Leu Gly Leu Arg Leu Gln Leu
1               5                   10                  15

Ser Leu Gly Ile Ile Pro Val Glu Glu Asn Pro Asp Phe Trp Asn
                20                  25                  30

Arg Gln Ala Ala Glu Ala Leu Gly Ala Ala Lys Lys Leu Gln Pro Ala
            35                  40                  45

Gln Thr Ala Ala Lys Asn Leu Ile Ile Phe Leu Gly Asp Gly Met Gly
        50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
                100                 105                 110

Ala Thr Ala Thr Ala Tyr Leu Cys Gly Val Lys Gly Asn Phe Gln Thr
            115                 120                 125

Ile Gly Leu Ser Ala Ala Ala Arg Phe Asn Gln Cys Asn Thr Thr Arg
        130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190
```

```
Val Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
                245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
        275                 280                 285

Glu Pro Gly Asp Met Lys Tyr Glu Ile His Arg Asp Ser Thr Leu Asp
    290                 295                 300

Pro Ser Leu Met Glu Met Thr Glu Ala Ala Leu Leu Leu Ser Arg
305                 310                 315                 320

Asn Pro Arg Gly Phe Phe Leu Phe Val Glu Gly Gly Arg Ile Asp His
                325                 330                 335

Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
        355                 360                 365

Thr Leu Ser Leu Val Thr Ala Asp His Ser His Val Phe Ser Phe Gly
    370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
        435                 440                 445

Glu Thr His Ala Gly Glu Asp Val Ala Val Phe Ala Arg Gly Pro Gln
    450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
            500                 505                 510

Pro Ala Leu Leu Pro Leu Leu Ala Gly Thr Leu Leu Leu Leu Gly Thr
        515                 520                 525

Ala Thr Ala Pro
    530

<210> SEQ ID NO 16
<211> LENGTH: 535
<212> TYPE: PRT
<213> ORGANISM: Homo sapiens

<400> SEQUENCE: 16

Met Leu Gly Pro Cys Met Leu Leu Leu Leu Leu Leu Leu Gly Leu Arg
1               5                   10                  15

Leu Gln Leu Ser Leu Gly Ile Ile Pro Val Glu Glu Glu Asn Pro Asp
            20                  25                  30
```

```
Phe Trp Asn Arg Glu Ala Ala Glu Ala Leu Gly Ala Ala Lys Lys Leu
         35                  40                  45

Gln Pro Ala Gln Thr Ala Ala Lys Asn Leu Ile Ile Phe Leu Gly Asp
         50                  55                  60

Gly Met Gly Val Ser Thr Val Thr Ala Ala Arg Ile Leu Lys Gly Gln
 65                  70                  75                  80

Lys Lys Asp Lys Leu Gly Pro Glu Ile Pro Leu Ala Met Asp Arg Phe
                 85                  90                  95

Pro Tyr Val Ala Leu Ser Lys Thr Tyr Asn Val Asp Lys His Val Pro
                100                 105                 110

Asp Ser Gly Ala Thr Ala Thr Ala Tyr Leu Cys Gly Val Lys Gly Asn
                115                 120                 125

Phe Gln Thr Ile Gly Leu Ser Ala Ala Arg Phe Asn Gln Cys Asn
                130                 135                 140

Thr Thr Arg Gly Asn Glu Val Ile Ser Val Met Asn Arg Ala Lys Lys
145                 150                 155                 160

Ala Gly Lys Ser Val Gly Val Val Thr Thr Thr Arg Val Gln His Ala
                165                 170                 175

Ser Pro Ala Gly Thr Tyr Ala His Thr Val Asn Arg Asn Trp Tyr Ser
                180                 185                 190

Asp Ala Asp Val Pro Ala Ser Ala Arg Gln Glu Gly Cys Gln Asp Ile
                195                 200                 205

Ala Thr Gln Leu Ile Ser Asn Met Asp Ile Asp Val Ile Leu Gly Gly
                210                 215                 220

Gly Arg Lys Tyr Met Phe Arg Met Gly Thr Pro Asp Pro Glu Tyr Pro
225                 230                 235                 240

Asp Asp Tyr Ser Gln Gly Gly Thr Arg Leu Asp Gly Lys Asn Leu Val
                245                 250                 255

Gln Glu Trp Leu Ala Lys Arg Gln Gly Ala Arg Tyr Val Trp Asn Arg
                260                 265                 270

Thr Glu Leu Met Gln Ala Ser Leu Asp Pro Ser Val Thr His Leu Met
                275                 280                 285

Gly Leu Phe Glu Pro Gly Asp Met Lys Tyr Glu Ile His Arg Asp Ser
                290                 295                 300

Thr Leu Asp Pro Ser Leu Met Glu Met Thr Glu Ala Ala Leu Arg Leu
305                 310                 315                 320

Leu Ser Arg Asn Pro Arg Gly Phe Phe Leu Phe Val Glu Gly Gly Arg
                325                 330                 335

Ile Asp His Gly His His Glu Ser Arg Ala Tyr Arg Ala Leu Thr Glu
                340                 345                 350

Thr Ile Met Phe Asp Asp Ala Ile Glu Arg Ala Gly Gln Leu Thr Ser
                355                 360                 365

Glu Glu Asp Thr Leu Ser Leu Val Thr Ala Asp His Ser His Val Phe
                370                 375                 380

Ser Phe Gly Gly Tyr Pro Leu Arg Gly Ser Ser Ile Phe Gly Leu Ala
385                 390                 395                 400

Pro Gly Lys Ala Arg Asp Arg Lys Ala Tyr Thr Val Leu Leu Tyr Gly
                405                 410                 415

Asn Gly Pro Gly Tyr Val Leu Lys Asp Gly Ala Arg Pro Asp Val Thr
                420                 425                 430

Glu Ser Glu Ser Gly Ser Pro Glu Tyr Arg Gln Gln Ser Ala Val Pro
                435                 440                 445
```

Leu Asp Glu Thr His Ala Gly Glu Asp Val Ala Val Phe Ala Arg
    450                 455                 460

Gly Pro Gln Ala His Leu Val His Gly Val Gln Glu Gln Thr Phe Ile
465                 470                 475                 480

Ala His Val Met Ala Phe Ala Ala Cys Leu Glu Pro Tyr Thr Ala Cys
                485                 490                 495

Asp Leu Ala Pro Pro Ala Gly Thr Thr Asp Ala Ala His Pro Gly Arg
                500                 505                 510

Ser Val Val Pro Ala Leu Leu Pro Leu Leu Ala Gly Thr Leu Leu Leu
                515                 520                 525

Leu Glu Thr Ala Thr Ala Pro
    530                 535

<210> SEQ ID NO 17
<211> LENGTH: 532
<212> TYPE: PRT
<213> ORGANISM: Homo sapiens

<400> SEQUENCE: 17

Met Gln Gly Pro Trp Val Leu Leu Leu Gly Leu Arg Leu Gln Leu
1               5                   10                  15

Ser Leu Gly Ile Ile Pro Val Glu Glu Glu Asn Pro Asp Phe Trp Asn
                20                  25                  30

Arg Gln Ala Ala Glu Ala Leu Gly Ala Ala Lys Lys Leu Gln Pro Ala
            35                  40                  45

Gln Thr Ala Ala Lys Asn Leu Ile Ile Phe Leu Gly Asp Gly Met Gly
        50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125

Ile Gly Leu Ser Ala Ala Ala Arg Phe Asn Gln Cys Asn Thr Thr Arg
130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Val Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
                245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
        275                 280                 285

```
Glu Pro Gly Asp Met Lys Tyr Glu Ile His Arg Asp Ser Thr Leu Asp
            290                 295                 300

Pro Ser Leu Met Glu Met Thr Glu Ala Ala Leu Leu Leu Leu Ser Arg
305                 310                 315                 320

Asn Pro Arg Gly Phe Phe Leu Phe Val Glu Gly Gly Arg Ile Asp His
                325                 330                 335

Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
                355                 360                 365

Thr Leu Ser Leu Val Thr Ala Asp His Ser His Val Phe Ser Phe Gly
370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
                420                 425                 430

Ser Gly Ser Pro Glu Tyr Arg Gln Gln Ser Ala Val Pro Leu Asp Gly
            435                 440                 445

Glu Thr His Ala Gly Glu Asp Val Ala Val Phe Ala Arg Gly Pro Gln
450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
                500                 505                 510

Pro Ala Leu Leu Pro Leu Leu Ala Gly Thr Leu Leu Leu Leu Gly Thr
            515                 520                 525

Ala Thr Ala Pro
            530

<210> SEQ ID NO 18
<211> LENGTH: 528
<212> TYPE: PRT
<213> ORGANISM: Homo sapiens

<400> SEQUENCE: 18

Met Gln Gly Pro Trp Val Leu Leu Leu Leu Gly Leu Arg Leu Gln Leu
1               5                   10                  15

Ser Leu Gly Val Ile Pro Ala Glu Glu Glu Asn Pro Ala Phe Trp Asn
                20                  25                  30

Arg Gln Ala Ala Glu Ala Leu Asp Ala Ala Lys Lys Leu Gln Pro Ile
            35                  40                  45

Gln Lys Val Ala Lys Asn Leu Ile Leu Phe Leu Gly Asp Gly Leu Gly
        50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
                100                 105                 110

Ala Thr Ala Thr Ala Tyr Leu Cys Gly Val Lys Ala Asn Phe Gln Thr
```

```
            115                 120                 125
Ile Gly Leu Ser Ala Ala Ala Arg Phe Asn Gln Cys Asn Thr Thr Arg
            130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                    165                 170                 175

Gly Thr Tyr Ala His Thr Val Asn Arg Asn Trp Tyr Ser Asp Ala Asp
                180                 185                 190

Met Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Arg Lys
            210                 215                 220

Tyr Met Phe Pro Met Gly Thr Pro Asp Pro Tyr Pro Ala Asp Ala
225                 230                 235                 240

Ser Gln Asn Gly Ile Arg Leu Asp Gly Lys Asn Leu Val Gln Glu Trp
                    245                 250                 255

Leu Ala Lys His Gln Gly Ala Trp Tyr Val Trp Asn Arg Thr Glu Leu
                260                 265                 270

Met Gln Ala Ser Leu Asp Gln Ser Val Thr His Leu Met Gly Leu Phe
            275                 280                 285

Glu Pro Gly Asp Thr Lys Tyr Glu Ile His Arg Asp Pro Thr Leu Asp
290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                    325                 330                 335

Gly His His Glu Gly Val Ala Tyr Gln Ala Leu Thr Glu Ala Val Met
                340                 345                 350

Phe Asp Asp Ala Ile Glu Arg Ala Gly Gln Leu Thr Ser Glu Glu Asp
            355                 360                 365

Thr Leu Thr Leu Val Thr Ala Asp His Ser His Val Phe Ser Phe Gly
            370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                    405                 410                 415

Gly Tyr Val Phe Asn Ser Gly Val Arg Pro Asp Val Asn Glu Ser Glu
                420                 425                 430

Ser Gly Ser Pro Asp Tyr Gln Gln Gln Ala Ala Val Pro Leu Ser Ser
            435                 440                 445

Glu Thr His Gly Gly Glu Asp Val Ala Val Phe Ala Arg Gly Pro Gln
            450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                    485                 490                 495

Pro Pro Ala Cys Thr Thr Asp Ala Ala His Pro Val Ala Ser Leu
                500                 505                 510

Pro Leu Leu Ala Gly Thr Leu Leu Leu Gly Ala Ser Ala Ala Pro
            515                 520                 525

<210> SEQ ID NO 19
```

<211> LENGTH: 726
<212> TYPE: PRT
<213> ORGANISM: Artificial Sequence
<220> FEATURE:
<223> OTHER INFORMATION: Synthetic Construct

<400> SEQUENCE: 19

```
Leu Val Pro Glu Lys Glu Lys Asp Pro Lys Tyr Trp Arg Asp Gln Ala
1               5                   10                  15
Gln Glu Thr Leu Lys Tyr Ala Leu Glu Leu Gln Lys Leu Asn Thr Asn
            20                  25                  30
Val Ala Lys Asn Val Ile Met Phe Leu Gly Asp Gly Met Gly Val Ser
        35                  40                  45
Thr Val Thr Ala Ala Arg Ile Leu Lys Gly Gln Leu His His Asn Pro
    50                  55                  60
Gly Glu Glu Thr Arg Leu Glu Met Asp Lys Phe Pro Phe Val Ala Leu
65                  70                  75                  80
Ser Lys Thr Tyr Asn Thr Asn Ala Gln Val Pro Asp Ser Ala Gly Thr
                85                  90                  95
Ala Thr Ala Tyr Leu Cys Gly Val Lys Ala Asn Glu Gly Thr Val Gly
            100                 105                 110
Val Ser Ala Ala Thr Glu Arg Ser Arg Cys Asn Thr Thr Gln Gly Asn
        115                 120                 125
Glu Val Thr Ser Ile Leu Arg Trp Ala Lys Asp Ala Gly Lys Ser Val
    130                 135                 140
Gly Ile Val Thr Thr Thr Arg Val Asn His Ala Thr Pro Ser Ala Ala
145                 150                 155                 160
Tyr Ala His Ser Ala Asp Arg Asp Trp Tyr Ser Asp Asn Glu Met Pro
                165                 170                 175
Pro Glu Ala Leu Ser Gln Gly Cys Lys Asp Ile Ala Tyr Gln Leu Met
            180                 185                 190
His Asn Ile Arg Asp Ile Asp Val Ile Met Gly Gly Gly Arg Lys Tyr
        195                 200                 205
Met Tyr Pro Lys Asn Lys Thr Asp Val Glu Tyr Glu Ser Asp Glu Lys
    210                 215                 220
Ala Arg Gly Thr Arg Leu Asp Gly Leu Asp Leu Val Asp Thr Trp Lys
225                 230                 235                 240
Ser Phe Lys Pro Arg Tyr Lys His Ser His Phe Ile Trp Asn Arg Thr
                245                 250                 255
Glu Leu Leu Thr Leu Asp Pro His Asn Val Asp Tyr Leu Leu Gly Leu
            260                 265                 270
Phe Glu Pro Gly Asp Met Gln Tyr Glu Leu Asn Arg Asn Asn Val Thr
        275                 280                 285
Asp Pro Ser Leu Ser Glu Met Val Val Ala Ile Gln Ile Leu Arg
    290                 295                 300
Lys Asn Pro Lys Gly Phe Phe Leu Leu Val Glu Gly Gly Arg Ile Asp
305                 310                 315                 320
His Gly His His Glu Gly Lys Ala Lys Gln Ala Leu His Glu Ala Val
                325                 330                 335
Glu Met Asp Arg Ala Ile Gly Gln Ala Gly Ser Leu Thr Ser Ser Glu
            340                 345                 350
Asp Thr Leu Thr Val Val Thr Ala Asp His Ser His Val Phe Thr Phe
        355                 360                 365
Gly Gly Tyr Thr Pro Arg Gly Asn Ser Ile Phe Gly Leu Ala Pro Met
    370                 375                 380
```

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
            405                 410                 415

Val Asp Tyr Ala His Asn Asn Tyr Gln Ala Gln Ser Ala Val Pro Leu
        420                 425                 430

Arg His Glu Thr His Gly Gly Glu Asp Val Ala Val Phe Ser Lys Gly
            435                 440                 445

Pro Met Ala His Leu Leu His Gly Val His Glu Gln Asn Tyr Val Pro
        450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
            485                 490                 495

Pro Ala Pro Glu Leu Leu Gly Gly Pro Ser Val Phe Leu Phe Pro Pro
        500                 505                 510

Lys Pro Lys Asp Thr Leu Met Ile Ser Arg Thr Pro Glu Val Thr Cys
            515                 520                 525

Val Val Val Asp Val Ser His Glu Asp Pro Glu Val Lys Phe Asn Trp
530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
            565                 570                 575

His Gln Asp Trp Leu Asn Gly Lys Glu Tyr Lys Cys Lys Val Ser Asn
        580                 585                 590

Lys Ala Leu Pro Ala Pro Ile Glu Lys Thr Ile Ser Lys Ala Lys Gly
            595                 600                 605

Gln Pro Arg Glu Pro Gln Val Tyr Thr Leu Pro Pro Ser Arg Glu Glu
        610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
            645                 650                 655

Asn Tyr Lys Thr Thr Pro Pro Val Leu Asp Ser Asp Gly Ser Phe Phe
        660                 665                 670

Leu Tyr Ser Lys Leu Thr Val Asp Lys Ser Arg Trp Gln Gln Gly Asn
            675                 680                 685

Val Phe Ser Cys Ser Val Met His Glu Ala Leu His Asn His Tyr Thr
        690                 695                 700

Gln Lys Ser Leu Ser Leu Ser Pro Gly Lys Asp Ile Asp Asp Asp Asp
705                 710                 715                 720

Asp Asp Asp Asp Asp Asp
            725

<210> SEQ ID NO 20
<211> LENGTH: 227
<212> TYPE: PRT
<213> ORGANISM: Artificial Sequence
<220> FEATURE:
<223> OTHER INFORMATION: Synthetic Construct

<400> SEQUENCE: 20

Asp Lys Thr His Thr Cys Pro Pro Cys Pro Ala Pro Glu Leu Leu Gly
1               5                   10                  15

```
Gly Pro Ser Val Phe Leu Phe Pro Pro Lys Pro Lys Asp Thr Leu Met
            20              25              30
Ile Ser Arg Thr Pro Glu Val Thr Cys Val Val Val Asp Val Ser His
        35              40              45
Glu Asp Pro Glu Val Lys Phe Asn Trp Tyr Val Asp Gly Val Glu Val
    50              55              60
His Asn Ala Lys Thr Lys Pro Arg Glu Glu Gln Tyr Asn Ser Thr Tyr
65              70              75              80
Arg Val Val Ser Val Leu Thr Val Leu His Gln Asp Trp Leu Asn Gly
            85              90              95
Lys Glu Tyr Lys Cys Lys Val Ser Asn Lys Ala Leu Pro Ala Pro Ile
            100             105             110
Glu Lys Thr Ile Ser Lys Ala Lys Gly Gln Pro Arg Glu Pro Gln Val
        115             120             125
Tyr Thr Leu Pro Pro Ser Arg Glu Glu Met Thr Lys Asn Gln Val Ser
    130             135             140
Leu Thr Cys Leu Val Lys Gly Phe Tyr Pro Ser Asp Ile Ala Val Glu
145             150             155             160
Trp Glu Ser Asn Gly Gln Pro Glu Asn Asn Tyr Lys Thr Thr Pro Pro
            165             170             175
Val Leu Asp Ser Asp Gly Ser Phe Phe Leu Tyr Ser Lys Leu Thr Val
            180             185             190
Asp Lys Ser Arg Trp Gln Gln Gly Asn Val Phe Ser Cys Ser Val Met
            195             200             205
His Glu Ala Leu His Asn His Tyr Thr Gln Lys Ser Leu Ser Leu Ser
        210             215             220
Pro Gly Lys
225
```

METHODS FOR TREATING CRANIOSYNOSTOSIS IN A PATIENT

FIELD

The disclosure concerns methods to treat craniosynostosis using a soluble alkaline phosphatase (sALP).

BACKGROUND

Hypophosphatasia (HPP) is a rare, heritable skeletal disease with an incidence of 1 per 100,000 births for the most severe forms of the disease. HPP is often fatal when observed at birth and has a high infant mortality rate of ~70%. Severely affected patients often die in infancy from respiratory insufficiency due to progressive chest deformity. The disorder results from loss-of-function mutations in the gene coding for tissue-nonspecific alkaline phosphatase (TNALP). TNALP activity plays an essential role in the development of the bone matrix. In particular, TNALP is an ectoenzyme present on the outer surface of osteoblast and chondrocyte cell membranes that hydrolyzes inorganic pyrophosphate (PPi), pyridoxal 5'-phosphate (PLP), and phosphoethanolamine (PEA). The primary role of TNALP in vivo is to regulate the extracellular PPi pool, as PPi is a potent inhibitor of bone mineralization. When there is a deficiency in TNALP activity, such as in HPP, PPi accumulates, which results in the inhibition of bone mineralization.

HPP leads to a remarkable range of symptoms and severity, from rickets (osteomalacia) to almost complete absence of bone mineralization in utero. Most patients exhibit the characteristics of skeletal changes, short stature, painful lower limbs, gait disturbance, and premature shedding of teeth. Bones of the cranium can also be affected, resulting in complex forms of craniosynostosis, particularly in cases of perinatal, childhood, and infantile HPP.

Craniosynostosis is a debilitating condition in which there is premature ossification of cranial sutures. Patients with craniosynostosis often suffer from high intracranial pressure, abnormal skull and facial shapes, airway impairments, obstructive sleep apnea, brain abnormalities, blindness, deafness, seizures, impairments in mental development, and death. The primary treatment available for craniosynostosis is surgical treatment with cranial vault remodeling in combination with genetic counseling, dental, and medical support.

Notably, surgically-corrected craniosynostosis may refuse necessitating multiple surgeries throughout infancy and childhood to relieve intracranial pressure, treat recurrent craniosynostosis, and normalize skull and facial shapes. Even with an early and accurate diagnosis, craniosynostosis has a high morbidity. Thus, there exists a need for methods that can be used to treat HPP patients with craniosynostosis.

SUMMARY

A first aspect of one embodiment features a method of treating craniosynostosis in a patient having hypophosphatasia (HPP) (e.g., a human). For example, the patient can exhibit or is likely to have increased intracranial pressure (ICP). The method includes administering a soluble alkaline phosphatase (sALP) to the patient, e.g., in combination with a cranial vault remodeling procedure.

In an embodiment, the sALP is administered to the patient prior to a cranial vault remodeling procedure. Alternatively, the sALP is administered to the patient after a cranial vault remodeling procedure. In particular, the sALP is administered to the patient about two months to about 1 day, particularly six weeks, one month, three weeks, two weeks, one week, 6 days, 5 days, four days, or two days, prior to or after a cranial vault remodeling procedure. For example, the sALP is administered about three weeks prior to or after the cranial vault remodeling procedure. Additionally, the sALP may be administered to the patient prior to premature fusion of cranial sutures.

In an embodiment, the patient is diagnosed with craniosynostosis requiring surgical correction prior to administration of the sALP. Alternatively, the patient is diagnosed with craniosynostosis requiring surgical correction prior to a cranial vault remodeling procedure. For example, craniosynostosis may be diagnosed by clinical examination, radiography (three-dimensional (3D) computed tomography (CT)), and/or ultrasonography.

In several embodiments of the first aspect of the disclosure, the patient is a human. In particular, the patient has infantile HPP, childhood HPP, perinatal benign HPP, or perinatal lethal HPP.

In various embodiments of the first aspect of the disclosure, the patient exhibits one or more additional symptoms of craniosynostosis, e.g., headaches, irritability, nausea and emesis (vomiting), pulsatile tinnitus, hearing loss, abnormal skull and facial shapes, airway impairments, obstructive sleep apnea, Chiari Type I malformation, brain abnormalities, papilledema, optic nerve damage, blindness, vision impairment, double vision, decreased visual acuity, deafness, seizures, impairments in mental development, herniation of cerebellar tonsils, syringomyelia, bilateral papilledema, nystagmus, microcephaly, brachycephaly, dolichocephaly, ventilator dependence, and/or chronic optic nerve edema.

In an embodiment of the first aspect of the disclosure, the method further includes monitoring ICP in the patient. For example, the method further includes monitoring one or more additional symptoms of craniosynostosis in the patient, such as by one or more of radiography (e.g., CT scan), ultrasonography, clinical examination, and/or determination of sALP activity. In particular, the determination of sALP activity includes measuring at least one of phosphoethanolamine (PEA), inorganic pyrophosphate (PPi), and/or pyridoxal 5'-phosphate (PLP) in a serum and/or blood sample from the patient. In particular embodiments, the sALP activity is below the age-adjusted normal range.

In various embodiments of the first aspect of the disclosure, the sALP is administered in an amount that is therapeutically effective to treat increased ICP. Furthermore, the sALP may be administered to treat and/or ameliorate one or more additional symptoms of craniosynostosis, e.g., headaches, irritability, nausea and emesis (vomiting), pulsatile tinnitus, hearing loss, abnormal skull and facial shapes, airway impairments, obstructive sleep apnea, Chiari Type I malformation, brain abnormalities, blindness, vision impairment, double vision, decreased visual acuity, deafness, seizures, impairments in mental development, herniation of cerebellar tonsils, syringomyelia, bilateral papilledema, nystagmus, microcephaly, brachycephaly, dolichocephaly, ventilator dependence, and/or chronic optic nerve edema.

In some embodiments of the first aspect of the disclosure, the sALP is administered in an amount that is therapeutically effective to treat at least one HPP phenotype, e.g., including one or more of premature loss of deciduous teeth, incomplete bone mineralization, elevated blood and/or urine levels of $PP_i$, elevated blood and/or urine levels of PEA, elevated blood and/or urine levels of PLP (particularly where PLP levels are at least twice the age-adjusted upper limit of normal), hypomineralization, rachitic ribs, hypercalciuria, short stature, skeletal deformity, waddling gait, bone pain, bone fracture, HPP-related seizure, inadequate weight gain, rickets, and/or calcium pyrophosphate dihydrate crystal deposition.

In some embodiments of the first aspect of the disclosure, the sALP is formulated in a pharmaceutical composition, with a pharmaceutically acceptable carrier (e.g., saline). In various embodiments, the pharmaceutical composition is formulated for intramuscular, subcutaneous, intravenous, oral, nasal, sublingual, intrathecal, or intradermal administration. For example, the pharmaceutical composition can be formulated for daily or weekly administration, e.g., in which the sALP is administered to the patient at a dosage of about 0.1 mg/kg to about 20 mg/kg, or at a weekly dosage of about 0.5 mg/kg to about 140 mg/kg.

In preferred embodiments of the first aspect of the disclosure, the sALP is physiologically active toward PEA, PPi, and PLP. For example, the sALP is catalytically competent to improve skeletal mineralization in bone.

In various embodiments of the first aspect of the disclosure, the sALP is the soluble extracellular domain of an alkaline phosphatase, e.g., in which the sALP is selected from the group consisting of tissue non-specific alkaline phosphatase (TNALP), placental alkaline phosphatase (PALP; e.g., SEQ ID NOs: 15 or 16), germ cell alkaline phosphatase (GCALP; e.g., SEQ ID NO: 17), and intestinal alkaline phosphatase (IALP; e.g., SEQ ID NO: 18). For example, the sALP is TNALP (e.g., the TNALP includes an amino acid sequence as set forth in SEQ ID NOs: 1-14).

In various embodiments of the first aspect of the disclosure, the sALP includes a polypeptide having the structure selected from the group consisting of Z-sALP-Y-spacer-X-$W_n$-V and Z—$W_n$-X-sALP-Y-spacer-V. For example, V, X, Y, and Z may each be absent or may be an amino acid sequence of at least one amino acid. In some embodiments, at least one of V, Z, and the spacer is absent. In particular embodiments, Y is two amino acid residues (e.g., Y is leucine-lysine) and/or X is two amino acid residues (e.g., X is aspartate-isoleucine). In certain embodiments, the structure is Z-sALP-Y-spacer-X-$W_n$-V.

$W_n$ can be a bone-targeting moiety, e.g., polyaspartic or polyglutamic region, in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50. Alternatively, $W_n$ is absent. In some embodiments, the spacer includes a fragment crystallizable (Fc) region, e.g., a CH2 domain, a CH3 domain, and a hinge region. In particular, the Fc is a constant domain of an immunoglobulin selected from the group consisting of IgG-1, IgG-2, IgG-3, and IgG-4. For example, the Fc is a constant domain of an immunoglobulin IgG-1.

In some embodiments of the first aspect of the disclosure, the sALP includes an amino acid sequence as set forth in SEQ ID NO: 19, e.g., the sALP is the amino acid sequence of SEQ ID NO: 19.

For any of the above aspects, the patient can exhibit an improvement in one or more symptoms of craniosynostosis, e.g., in which the one or more symptoms includes increased ICP, abnormal skull and facial shapes, intracranial hypertension, airway impairments, obstructive sleep apnea, pulsatile tinnitus, Chiari Type I malformation, brain abnormalities, hearing loss, blindness, vision impairment, double vision, deafness, seizures, impairments in mental development, irritability, nausea, vomiting, emesis, herniation of cerebellar tonsils, syringomyelia, headaches, bilateral papilledema, nystagmus, decreased visual acuity, microcephaly, brachycephaly, dolichocephaly, ventilator dependence, papilledema, and/or chronic optic nerve edema.

For any of the above aspects, the patient exhibits an improvement in one or more neurological symptoms.

For any of the above aspects, the sALP can be used in the manufacture of a medicament for treating or preventing craniosynostosis.

Another aspect of the disclosure features a method of diagnosing HPP in a patient, in which the method including determining the level of TNALP activity in a patient having craniosynostosis. In particular, the determination of TNALP activity can include measuring at least one of PEA, PPi, and/or PLP in a serum and/or blood sample from the patient (particularly where the PLP level is at least twice the upper limit of age-adjusted normal).

Another aspect of the disclosure features a method of diagnosing HPP in a patient, in which method including determining the presence of a mutation in TNALP in a patient having craniosynostosis. In various embodiments, the mutation in TNALP is associated with HPP.

Definitions

By "craniosynostosis" is meant a condition in which adjacent calvarial (skull cap) bones partially or completely fuse prematurely (including partial or complete mineralization), thereby deleteriously changing the growth pattern of the skull. Symptoms of craniosynostosis may include, but are not limited to, headaches, irritability, nausea and emesis (vomiting), pulsatile tinnitus, hearing loss, abnormal skull and facial shapes, airway impairments, obstructive sleep apnea, pulsatile tinnitus, Chiari Type I malformation, brain abnormalities, blindness, vision impairment, double vision, decreased visual acuity, deafness, seizures, impairments in mental development, herniation of cerebellar tonsils, syringomyelia, bilateral papilledema, nystagmus, microcephaly, brachycephaly, dolichocephaly, ventilator dependence, and/or chronic optic nerve edema.

The terms "intracranial pressure" and "ICP," as used herein, refer to pressure within the skull that impinges on the brain tissue and cerebrospinal fluid. For example, increased ICP includes but is not limited to ICP greater than 10 mm Hg, in which 10-20 mm Hg is greater than typical ICP, and severe increased ICP is greater than 20 mm Hg. Symptoms associated with increased ICP may include headaches, irritability, nausea and emesis (vomiting), pulsatile tinnitus, hearing loss, abnormal skull and facial shapes, airway impairments, obstructive sleep apnea, pulsatile tinnitus, Chiari Type I malformation, brain abnormalities, blindness, vision impairment, double vision, decreased visual acuity, deafness, seizures, impairments in mental development, herniation of cerebellar tonsils, syringomyelia, bilateral papilledema, nystagmus, microcephaly, brachycephaly, dolichocephaly, ventilator dependence, and/or chronic optic nerve edema. Without being so limited, increased ICP may be diagnosed and/or monitored with one or more of radiography (e.g., computed tomography (CT) scan), ultrasonography, and clinical examination.

The terms "cranial vault remodeling procedure," as used herein, refers to one or more surgeries involving repositioning and/or removal of bone of the skull, e.g., to relieve ICP and/or one or more other symptoms of craniosynostosis.

The terms "hypophosphatasia" and "HPP," as used herein, refer to a rare, heritable skeletal disorder caused by, e.g., one or more loss-of-function mutations in the ALPL (alkaline phosphatase, liver/bone/kidney) gene, which encodes tissue-nonspecific alkaline phosphatase (TNALP). HPP may be further characterized as infantile HPP, childhood HPP, perinatal HPP (e.g., benign perinatal HPP or lethal perinatal HPP), adult HPP, or odontohypophosphatasia.

The term "HPP phenotype," as used herein, refers to any one of craniosynostosis, rickets (defect in growth plate cartilage), osteomalacia, elevated blood and/or urine levels of inorganic pyrophosphate (PP;), phosphoethanolamine (PEA), or pyridoxal 5'-phosphate (PLP), seizure, bone pains, and calcium pyrophosphate dihydrate crystal deposition (CPPD) in joints leading to chondrocalcinosis and premature death. Without being so limited, a HPP phenotype can be documented by one or more of growth retardation with a decrease of long bone length (including but not limited to femur, tibia, humerus, radius, and/or ulna), a decrease of the mean density of total bone and a decrease of bone mineralization in bones such as femur, tibia, ribs and metatarsi, and phalange, a decrease in teeth mineralization, and a premature loss of deciduous teeth (e.g., aplasia, hypoplasia, or dysplasia of dental cementum). Without being so limited, correction or prevention of bone mineralization defect may be observed by one or more of the following: an increase of long bone length, an increase of mineralization in bone and/or teeth, a correction of bowing of the legs, a reduction of bone pain and a reduction of CPPD crystal deposition in joints.

The terms "sALP," "soluble alkaline phosphatase," and "extracellular domain of an alkaline phosphatase" are used interchangeably and refer to a soluble, non-membrane-bound alkaline phosphatase or a domain, biologically active fragment, or biologically active variant thereof. sALPs include, for example, an alkaline phosphatase lacking a C-terminal glycolipid anchor (GPI signal sequence, e.g., polypeptides including or consisting of the amino acid residues 18-502 of a human TNALP (SEQ ID NOs: 1, 2, 3, 4, or 5)). In particular, a TNALP may include, e.g., a polypeptide including or consisting of amino acid residues 1-485 of SEQ ID NO: 19. sALPs further include, for example, mammalian orthologs of human TNALP, such as a rhesus TNALP (SEQ ID NO: 6), a rat TNALP (SEQ ID NO: 7), a canine TNALP (SEQ ID NO: 8), a porcine TNALP (SEQ ID NO: 9), a murine TNALP (SEQ ID NO: 10), a bovine TNALP (SEQ ID NOs: 11-13), or a feline TNALP (SEQ ID NO: 14). sALPs also include soluble, non-membrane-bound forms of human PALP (e.g., polypeptides including or consisting of amino acid residues 18-502 of SEQ ID NOs: 15 or 16), GCALP (e.g., polypeptides including or consisting of amino acid residues 18-502 of SEQ ID NO: 17), and IALP (e.g., polypeptides including or consisting of amino acid residues 18-502 of SEQ ID NO: 18), and additional variants and analogs thereof that retain alkaline phosphatase activity, e.g., the ability to hydrolyze $PP_i$. A sALP, in particular, lacks the N-terminal signal peptide (e.g., aa 1-17 of SEQ ID NOs: 1-5, 7, 10-12, or 14 or aa 1-25 of SEQ ID NO: 6).

By "sALP polypeptide" is meant a polypeptide having the structure A-sALP-B, wherein sALP is as defined herein and each of A and B is absent or is an amino acid sequence of at least one amino acid (e.g., any sALP fusion polypeptide described herein).

By "Fc" is meant a fragment crystallizable region of an immunoglobulin, e.g., IgG-1, IgG-2, IgG-3, IgG-3 or IgG-4, including the CH2 and CH3 domains of the immunoglobulin heavy chain. Fc may also include any portion of the hinge region joining the Fab and Fc regions. The Fc can be of any mammal, including human, and may be post-translationally modified (e.g., by glycosylation). In a non-limiting example, Fc can be the fragment crystallizable region of human IgG-1 having the amino acid sequence of SEQ ID NO: 20.

By "bone-targeting moiety" is meant an amino acid sequence of between 1 and 50 amino acid residues in length having a sufficient affinity to the bone matrix, such that the bone-targeting moiety, singularly, has an in vivo binding affinity to the bone matrix that is about $10^{-6}$ M to about $10^{-15}$ M (e.g., $10^{-7}$ M, $10^{-8}$ M, $10^{-9}$ M, $10^{-19}$ M, $10^{-11}$ M, $10^{-12}$ M, $10^{-13}$ M, $10^{-14}$ M, or $10^{-15}$ M).

By "extracellular domain" is meant any functional extracellular portion of the native protein, e.g., alkaline phosphatase. In particular, the extracellular domain lacks the signal peptide.

By "signal peptide" is meant a short peptide (5-30 amino acids long) at the N-terminus of a polypeptide that directs a polypeptide towards the secretory pathway (e.g., the extracellular space). The signal peptide is typically cleaved during secretion of the polypeptide. The signal sequence may direct the polypeptide to an intracellular compartment or organelle, e.g., the Golgi apparatus. A signal sequence may be identified by homology, or biological activity, to a peptide with the known function of targeting a polypeptide to a particular region of the cell. One of ordinary skill in the art can identify a signal peptide by using readily available software (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). A signal peptide can be one that is, for example, substantially identical to amino acid residues 1-17 of SEQ ID NOs: 1-5, 7, 10-12, or 14 or amino acid residues 1-25 of SEQ ID NO: 6.

By "fragment" is meant a portion of a polypeptide or nucleic acid molecule that contains, preferably, at least 10%, 20%, 30%, 40%, 50%, 60%, 70%, 75%, 80%, 85%, 90%, 95%, 96%, 97%, 98%, 99%, or more of the entire length of the reference nucleic acid molecule or polypeptide. A fragment may contain, e.g., 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 400, 500, 600, 700, or more amino acid residues, up to the entire length of the polypeptide. Exemplary sALP fragments have amino acid residues 18-498, 18-499, 18-500, 18-501, 18-502, 18-503, 18-504, 18-505, 18-506, 18-507, 18-508, 18-509, 18-510, 18-511, or 18-512 of ALP (e.g., SEQ ID NO: 1-5), and may include additional C-terminal and/or N-terminal portions.

As used herein, when a polypeptide or nucleic acid sequence is referred to as having "at least X % sequence identity" to a reference sequence, wherein "X" is a real number, it is meant that at least X percent of the amino acid residues or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., *J. Mol. Biol.* 147:195-7, 1981) and BLAST (Basic Local Alignment Search Tool; Altschul et al., *J. Mol. Biol.* 215: 403-10, 1990). These and other alignment algorithms are accessible using publicly available computer software such as "Best Fit" (Smith and Waterman, Advances in Applied Mathematics, 482-489, 1981) as incorporated into GeneMatcher Plus (Schwarz and Dayhoff, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, Megalign (DNASTAR), or other software/hardware for alignment. In addition, those skilled in the art can determine appropriate parameters for measuring alignment, including any algorithms needed to achieve optimal alignment over the length of the sequences being compared.

By "nucleic acid molecule" is meant a molecule, e.g., RNA or DNA, having a sequence of two or more covalently bonded, naturally occurring or modified nucleotides. The nucleic acid molecule may be, e.g., single or double stranded, and may include modified or unmodified nucleotides, or mixtures or combinations thereof. Various salts, mixed salts, and free acid forms are also included.

The terms "peptide," "polypeptide," and "protein" are used interchangeably and refer to any chain of two or more natural or unnatural amino acid residues, regardless of post-translational modification (e.g., glycosylation or phosphorylation), constituting all or part of a naturally-occurring or non-naturally occurring polypeptide or peptide, as is described herein.

By "pharmaceutically acceptable carrier" or "pharmaceutically acceptable excipient" is meant at least one carrier or excipient, respectively, which is physiologically acceptable to the treated patient while retaining the therapeutic properties of the compound with which it is administered. One exemplary pharmaceutically acceptable carrier substance is physiological saline. Other physiologically acceptable carriers and their formulations are known to those skilled in the art and described, for example, in Remington's Pharmaceutical Sciences (20th edition), A. Gennaro, Ed., 2000, Lippincott, Williams & Wilkins, Philadelphia, Pa.

By "pharmaceutical composition" is meant a composition containing a polypeptide or nucleic acid molecule as described herein formulated with at least one pharmaceutically acceptable excipient, diluent, or carrier. The pharmaceutical composition may be manufactured or sold with the approval of a governmental regulatory agency as part of a therapeutic regimen for the treatment or prevention of a disease or event in a patient. Pharmaceutical compositions can be formulated, for example, for subcutaneous administration, intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form.

The terms "subject" and "patient" are used interchangeably and mean a mammal, including, but not limited to, a human or a non-human mammal, such as a bovine, equine, canine, ovine, or feline.

By "therapeutically effective amount" is meant an amount of a polypeptide or nucleic acid molecule described herein that is sufficient to substantially improve, treat, prevent, delay, suppress, or arrest at least one symptom of craniosynostosis, or that is sufficient to treat a HPP patient exhibiting increased ICP or likely to have or to develop increased ICP. A therapeutically effective amount of a composition described herein may depend on the severity of the disorder being treated and the condition, weight, and general state of the patient and can be determined by an ordinarily-skilled artisan with consideration of such factors. A therapeutically effective amount of a composition described herein can be administered to a patient in a single dose or in multiple doses administered over a period of time.

By "treating," "treat," or "treatment" is meant the medical management of a patient with the intent to cure, ameliorate, stabilize, reduce the likelihood of, or prevent craniosynostosis and/or management of a patient exhibiting or likely to have increased ICP, e.g., by administering a pharmaceutical composition. This term includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief or improvement of at least one symptom rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a patient who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

As used herein, "about" refers to an amount that is ±10% of the recited value.

As used herein, "a" or "an" means "at least one" or "one or more" unless otherwise indicated. In addition, the singular forms "a", "an", and "the" include plural referents unless the context clearly dictates otherwise.

Other features and advantages of the present disclosure will be apparent from the following Detailed Description, the drawings, and the claims.

BRIEF DESCRIPTION OF THE SEVERAL VIEWS OF THE DRAWINGS

FIG. 1A is a top view of the 3D head CT scan revealing left coronal and sagittal craniosynostosis with widening of the right coronal suture and persistent anterior fontanelle. FIG. 1B is an anterior view of the 3D head CT scan revealing left coronal craniosynostosis with facial scoliosis.

FIG. 2A is a preoperative sagittal CT scan showing loss of sulci and gyri, scalloping of the inner table, absence of extraaxial spaces, and crowding at the foramen magnum suggestive of Chiari Type I malformation. FIG. 2B is a postoperative sagittal CT performed one year after surgery now exhibiting definition of sulci and gyri, increased space in the basal cisterns and extraaxial spaces, and less crowding at the craniovertebral junction.

FIG. 3A is a preoperative lateral view of a 3D head CT scan with an obliterated left coronal suture. FIG. 3B is a preoperative top view of a 3D head CT scan with an obliterated sagittal suture and bony prominence over the bregma with persistent anterior fontanelle. FIG. 3C is a seven-month postoperative lateral view of a 3D head CT scan demonstrating improved bone growth in the calvaria.

FIG. 4A is a preoperative axial CT scan demonstrating absence of extraaxial spaces, small ventricular spaces, and tight basilar cisterns. FIG. 4B is a postoperative axial CT scan performed 3 months after surgery revealing cranial expansion, open basal cisterns, reconstitution of the third ventricle, and presence of extraaxial spaces.

DETAILED DESCRIPTION

Figure 1A:
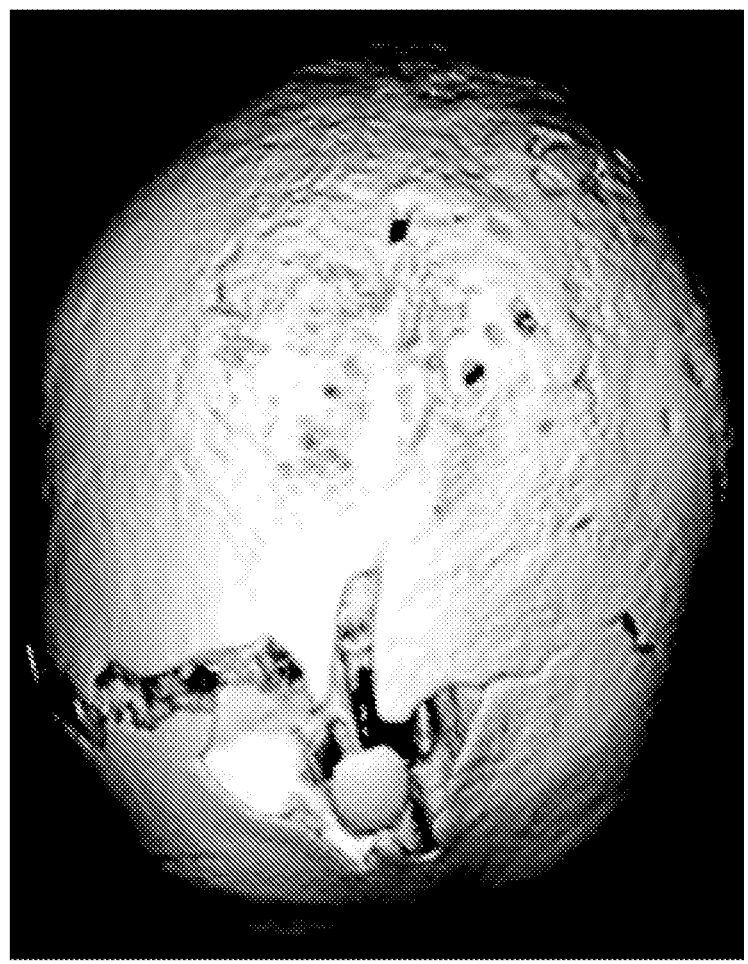
FIGS. 1A-1B are images showing a three-dimensional (3D) computed tomography (CT) scan of the head of a patient with craniosynostosis.

We have discovered that a sALP (such as TNALP, for example SEQ ID NO: 19, such as STRENSIQ™) may be used effectively in combination with surgery, e.g., a cranial vault remodeling procedure, to treat craniosynostosis (e.g., the premature fusion of cranial bones) in a patient (e.g., a human, particularly an infant or a child) with hypophosphatasia (HPP). In particular, sALP may be administered to treat HPP patients exhibiting or likely to have increased intracranial pressure (ICP). The sALP may be a sALP polypeptide (e.g., a secreted soluble, extracellular domain of an ALP) or a sALP fusion polypeptide (e.g., a sALP fused to a fragment crystallizable (Fc) region and/or a bone-targeting moiety). Methods for administering a sALP in combination with a cranial surgery, e.g., a cranial vault remodeling procedure (e.g., in which the sALP is administered prior to, or after, a cranial vault remodeling procedure) to treat craniosynostosis, e.g., in HPP patients exhibiting or likely to have increased ICP, are described.

Methods of Treatment

Provided herein are methods for treating craniosynostosis in a patient, such as a patient having hypophosphatasia (HPP) (e.g., a human). In particular, the patient may exhibit or may be likely to have increased intracranial pressure (ICP). The method involves administering a soluble alkaline phosphatase (sALP; such as TNALP, for example SEQ ID NO: 19, such as STRENSIQ™) to the patient, e.g., in combination with a cranial surgery, e.g., a cranial vault remodeling procedure. In particular, a sALP can be administered to the patient prior to the cranial vault remodeling procedure to, e.g., allow for proper fusion of the cranial sutures or prevent immature fusion of the cranial sutures. Alternatively, if the patient exhibits symptoms of craniosynostosis (e.g., increased ICP) that require a cranial vault remodeling procedure prior to administration of a sALP (such as TNALP, for example SEQ ID NO: 19, such as STRENSIQ™), the sALP can be administered after the cranial vault remodeling procedure to allow for, e.g., relief of increased ICP, proper fusion of the cranial sutures, and/or proper growth of the skull.

Patients may be diagnosed with craniosynostosis prior to administration of a sALP and/or cranial vault remodeling procedure, such as by clinical examination, radiography (e.g., computed tomography (CT)), and/or ultrasonography. Symptoms of craniosynostosis can be monitored following treatment (e.g., following sALP (such as TNALP, for example SEQ ID NO: 19, such as STRENSIQ™) administration in combination with a cranial vault remodeling procedure) to determine the effectiveness of the treatment and/or the timing of sALP administration relative to, e.g., the cranial vault remodeling procedure (e.g., administration of sALP prior to or after the cranial vault remodeling procedure).

Treatment with a sALP (such as TNALP, for example SEQ ID NO: 19, such as STRENSIQ™) combined with a cranial vault remodeling procedure, can result in an improvement in a symptom of craniosynostosis, such as a decrease in ICP. The methods of the present invention can be used to treat neurological symptoms associated with craniosynostosis, such that there is reversal of craniosynostosis or a reduction in the severity of symptoms of craniosynostosis, such as a decrease in ICP. In particular, the methods may result in an improvement in symptoms including, but not limited to, headaches, irritability, nausea and emesis (vomiting), pulsatile tinnitus, hearing loss, abnormal skull and facial shapes, airway impairments, obstructive sleep apnea, pulsatile tinnitus, Chiari Type I malformation, brain abnormalities, blindness, vision impairment, double vision, decreased visual acuity, deafness, seizures, impairments in mental development, herniation of cerebellar tonsils, syringomyelia, bilateral papilledema, nystagmus, microcephaly, brachycephaly, dolichocephaly, ventilator dependence, and/or chronic optic nerve edema.

The methods described herein may result in an improvement in any of the aforementioned symptoms. For example, treatment with a sALP (such as TNALP, for example SEQ ID NO: 19, such as STRENSIQ™) combined with a cranial vault remodeling procedure can result in a decrease the occurrence of headaches and irritability. Treatment can result in fewer incidents of nausea and emesis over, e.g., a 30 day period after receiving treatment with sALP combined with a cranial vault remodeling procedure (e.g., a 2 day period, a 4 day period, a 6 day period, a 8 day period, a 10 day period, a 15 day period, a 20 day period, a 25 day period, a 30 day period, a 40 day period, a 60 day period, a 60 day period after receiving treatment). Patients may experience an improvement in vision, such as the reversal of a vision impairment or increased visual acuity, following treatment with a sALP combined with a cranial vault remodeling procedure. The patient may exhibit improved neurological symptoms, such as a lack of or decrease in brain abnormalities, relative to the patient's condition prior to treatment. For example, following the methods of treatment, the head circumference of the patient may increase and approach the average head circumference according to the patient's age.

Hypophosphatasia

HPP is a matrix mineralization disorder that may be treated with a sALP, e.g., in combination with a cranial surgery, such as a cranial vault remodeling procedure. A sALP (such as TNALP, for example SEQ ID NO: 19, STRENSIQ™) can be administered, as described herein, to treat, e.g., perinatal HPP, infantile HPP, childhood HPP, adult HPP, and odontohypophosphatasia. In particular, patients having infantile HPP, childhood HPP, and perinatal HPP (e.g., perinatal benign or perinatal lethal HPP) can be treated with a sALP (such as TNALP, for example SEQ ID NO: 19, such as STRENSIQ™), e.g., combined with a cranial vault remodeling procedure.

A phenotype associated with HPP, e.g., perinatal HPP, infantile HPP, childhood HPP, adult HPP, and odontohypophosphatasia, can be treated with a sALP, e.g., combined with a cranial vault remodeling procedure. For instance, the methods can be used to treat a perinatal HPP patient, such as a patient with increased respiratory compromise due to hypoplastic and rachitic disease of the chest; diminished ossification of the skull; diminished ossification and height of vertebral bodies; and/or absent ossification of the humeral, radial, and ulnar metaphyses with marked metaphyseal irregularity; fragmentation and fraying. The methods can also be used to treat patients exhibiting symptoms of infantile HPP, including, but not limited to, inadequate weight gain, the appearance of rickets, impaired skeletal mineralization, progressive skeletal demineralization, rib fractures, and chest deformity. A patient with childhood HPP may be treated with the methods, such as patients that exhibit symptoms including premature loss of deciduous teeth (e.g., as a result of aplasia, hypoplasia, or dysplasia of dental cementum) and rickets, which causes short stature and skeletal deformities, such as bowed legs and enlarged wrists, knees, and ankles as a result of flared metaphysis. Accordingly, the methods may be used to alleviate any of the symptoms of HPP described herein. Non-limiting examples of HPP symptoms that may be treated, e.g., with a sALP, include elevated blood and/or urine levels of inorganic pyrophosphate ($PP_i$), elevated blood and/or urine levels of phosphoethanolamine (PEA), elevated blood and/or urine levels of pyridoxal 5'-phosphate (PLP), hypomineralization, rachitic ribs, hypercalciuria, bone pain, bone fracture, HPP-related seizure, inadequate weight gain, and/or calcium pyrophosphate dihydrate crystal deposition.

A patient with a mutation in TNALP can also be treated with a sALP (such as TNALP, for example SEQ ID NO: 19, such as STRENSIQ™) combined with a cranial surgery, such a cranial vault remodeling procedure, e.g., to alleviate increased ICP or symptoms associated with craniosynostosis. Missense mutations at a variety of positions in TNALP, including the enzyme's active site vicinity, homodimer interface, crown domain, amino-terminal arm, and calcium-binding site, have all been found to affect its catalytic activity. In addition, missense, nonsense, frame-shift, and splice site mutations have also been shown to lead to aberrant mutant proteins or intracellular trafficking defects that lead to subnormal activity on the cell surface. Accordingly, the methods may be used to treat patients with different mutation in TNALP (e.g., missense mutations, frame-shift, nonsense, and splicing mutations). For instance, the presence of a mutation in TNALP may be detected in a sample from the patient prior to or after treatment (e.g., sALP administration in combination with cranial vault remodeling). Additionally, a parent of the patient and/or a fetal sample (e.g., fetal nucleic acid obtained from maternal blood, placental, and/or fetal samples) may be tested by methods known in the art for a mutation in TNALP. Traditional management of HPP has also included symptomatic treatment of the phenotypic manifestations of the disease, e.g., treating hypercalcemia with dietary restriction or calciuretics and orthopedic stabilization of fractures. Accordingly, these treatments (e.g., dietary restriction, calciuretics, and orthopedic stabilization of fractures) may be used with the administration of a sALP combined with a cranial surgery, such a cranial vault remodeling procedure, e.g., to alleviate increased ICP or symptoms associated with craniosynostosis.

Craniosynostosis

Certain patients with HPP and craniosynostosis may be treated with a sALP (such as TNALP, for example SEQ ID NO: 19, such as STRENSIQ™) combined with a cranial surgery, such as cranial vault remodeling procedure. In particular, patients treated using the methods described herein may include, e.g., infants, children, and perinatal patients with craniosynostosis (e.g., the premature fusion of cranial sutures), such as a patient exhibiting or likely to develop increased ICP. Treatment with a sALP, e.g., combined with a cranial vault remodeling procedure, may also be initiated in the neonatal period (e.g., within 1 hour, 8 hours, 12 hours, 1 day, 2 days, 3 days, 4 days, 5 days, 6 days, 1 week, 2 weeks, 3 weeks, or one month) of birth, or prior to birth. Such treatment may also be initiated in utero. These methods can also be used to treat craniosynostosis characterized by the suture or sutures that fuse. Fusion typically involves one or more of the sagittal, metopic, coronal, lambdoidal, and squamosal sutures. Accordingly, a patient exhibiting fusion of one or more cranial sutures (e.g., sagittal, metopic, coronal, lambdoidal, and squamosal) resulting in craniosynostosis may be treated with a sALP (such as TNALP, for example SEQ ID NO: 19, such as STRENSIQ™) in combination with surgery.

Patients with different forms of craniosynostosis can also be treated with a sALP (such as TNALP, for example SEQ ID NO: 19, such as STRENSIQ™) combined with a cranial vault remodeling procedure. In particular, known mutations associated with craniosynostosis occur in the fibroblast growth factor receptors (FGFRs) and are associated with over 20 different genetic disorders, including Pfeiffer, Saethre-Chotzen, Apert, Crouzon, Beare-Stevenson, Jackson-Weiss, Antley-Bixler, and Muenke syndromes. Thus, a patient treated with the methods disclosed herein may have, e.g., a mutation in a FGFR (e.g., FGFR1, FGFR2, or FGFR3) gene. Additionally, a mutation in a FGFR gene can be detected in a sample from the patient prior to or after treatment (e.g., a sALP combined with cranial vault remodeling). Additionally, the parents of the patient and/or fetal samples (e.g., fetal nucleic acid obtained from maternal blood, placental, or fetal samples) may be tested by methods known in the art for the mutation. Craniosynostosis may also develop in relation to an underlying disorder, which may include, but are not limited to HPP, hyperthyroidism, hypercalcemia, vitamin D deficiency, renal osteodystrophy, Hurler's Syndrome, sickle cell disease, and thalassemia. For instance, the methods described herein may resolve and/or prevent symptoms associated with craniosynostosis in a patient with any of the aforementioned disorders.

The methods may further include the diagnosis of patients (e.g., HPP patients) with craniosynostosis. Patients may be diagnosed with craniosynostosis prior to or after administration of a sALP (such as TNALP, for example SEQ ID NO: 19, such as STRENSIQ™) and/or cranial vault remodeling procedure. Craniosynostosis may be diagnosed, for example, by clinical examination, e.g., a physician may examine the head and suture lines of the patient. The presence of a ridge where the suture lines are located may be diagnostic of craniosynostosis, as this is not present with normal sutures. The symmetry in head shape, head size (e.g., microcephalic), location and symmetry of ears and eyes, shape and slope of the forehead, and size and shape of the sutures are also examined during diagnosis of craniosynostosis. Any of these clinical features can be used to diagnose craniosynostosis according to the methods described herein. Diagnostic methods of the present invention may further include radiography (e.g., an X-ray or computed tomography (CT)) and/or ultrasound. In particular, three-dimensional (3D) CT allows for determination of the severity and location of the fused sutures in addition to characterization of skull features and presence of deformities. Sonogram can also be used for diagnosis of craniosynostosis in a prenatal patient.

Symptoms of craniosynostosis in patients (e.g., HPP patients) may also be monitored prior to or after a patient is treated with a sALP (such as TNALP, for example SEQ ID NO: 19, such as STRENSIQ™) combined with a cranial vault remodeling procedure. For instance, symptoms of craniosynostosis may be monitored prior to treatment to assess the severity of craniosynostosis and condition of the patient prior to performing the methods. The methods of the present invention may include monitoring of ICP (e.g., direct ICP monitoring using a probe passed through the skull to allow continuous recording of ICP or indirect ICP monitoring via a lumbar cerebrospinal fluid (CSF) catheter) and symptoms associated with increased ICP. Symptoms associated with increased ICP may include, but are not limited to, headaches, irritability, nausea and emesis (vomiting), pulsatile tinnitus, hearing loss, abnormal skull and facial shapes, airway impairments, obstructive sleep apnea, Chiari Type I malformation, brain abnormalities, blindness, vision impairment, double vision, decreased visual acuity, deafness, seizures, impairments in mental development, herniation of cerebellar tonsils, syringomyelia, bilateral papilledema, nystagmus, microcephaly, brachycephaly, dolichocephaly, ventilator dependence, and/or chronic optic nerve edema. Monitoring may also include radiography, ultrasonography, clinical examination, and/or determination of sALP activity. In particular, sALP activity may be determined by measuring phosphoethanolamine (PEA), inorganic pyrophosphate (PPi), and/or pyridoxal 5′-phosphate (PLP) in a serum and/or blood sample from the patient.

Alkaline Phosphatase

The present disclosure is not limited to a particular alkaline phosphatase (ALP) or nucleic acid sequence encoding an ALP. Alkaline phosphatases encompass a group of enzymes that catalyze the cleavage of a phosphate moiety (e.g., hydrolysis of pyrophosphate, $PP_i$,). There are four known mammalian alkaline phosphatase (ALP) isozymes: tissue nonspecific alkaline phosphatase (TNALP; described further below), placental alkaline phosphatase (PLALP) (e.g., Accession Nos. P05187, NP_112603, and NP_001623), germ cell alkaline phosphatase (GALP) (e.g., Accession No. P10696), and intestinal alkaline phosphatase (IALP) (e.g., Accession Nos. P09923 and NP_001622). In addition to the exemplary ALPs discussed above, this disclosure also provides any polypeptide comprising the identical or similar catalytic site structure and/or enzymatic activity of ALP for treating craniosynostosis in HPP patients. Bone delivery conjugates including sALP are further described in PCT publication Nos: WO 2005/103263 and WO 2008/138131, which are incorporated herein by reference in their entirety.

TNALPs that may be used according to the methods described herein include, e.g., human TNALP (Accession Nos. NP_000469, AAI10910, AAH90861, AAH66116, AAH21289, and AAI26166); rhesus TNALP (Accession No. XP_01109717); rat TNALP (Accession No. NP_037191); dog TNALP (Accession No. AAF64516); pig TNALP (Accession No. AAN64273), mouse (Accession No. NP_031457), cow TNALP (Accession Nos. NP_789828, NP_776412, AAM 8209, and AAC33858), and cat TNALP (Accession No. NP_001036028). In particular, TNALP may be a recombinant human TNALP (e.g., SEQ ID NO: 19, STRENSIQ™; see U.S. Pat. Nos. 7,763,712 and 7,960,529, incorporated herein by reference in their entirety) used for the treatment of craniosynostosis, such as in HPP patients.

Soluble Alkaline Phosphatase

The ALPs of the present invention include soluble (e.g., extracellular or non-membrane-bound) forms of any of the alkaline phosphatases described herein. The sALP of the invention can be, for example, a soluble form of human tissue non-specific alkaline phosphatase (hTNALP). The present disclosure is not limited to a particular sALP and may include any sALP polypeptide that is physiologically active toward, e.g., phosphoethanolamine (PEA), inorganic pyrophosphate (PPi), and pyridoxal 5′-phosphate (PLP). In particular, a sALP of the present invention is catalytically competent to improve skeletal mineralization in bone. The present invention further includes nucleic acids encoding the sALPs described herein that may be used to treat the conditions described herein, e.g., craniosynostosis in HPP patients.

TNALP is a membrane-bound protein anchored by a glycolipid moiety at the C-terminal (Swiss-Prot, P05186). This glycolipid anchor (GPI) is added post-translationally after the removal of a hydrophobic C-terminal end, which serves both as a temporary membrane anchor and as a signal for the addition of the GPI. While the GPI anchor is located in the cell membrane, the remaining portions of TNALP are extracellular. In particular, TNALP (e.g., human TNALP (hTNALP)) may be engineered to replace the first amino acid of the hydrophobic C-terminal sequence (an alanine) with a stop codon, thereby producing an engineered hTNALP that contains all amino acid residues of the native anchored form of TNALP and lacks the GPI membrane anchor. One skilled in the art will appreciate that the position of the GPI membrane anchor will vary in different ALPs and may include, e.g., the last 10, 12, 14, 16, 18, 20, 21, 22, 23, 24, 25, 26, 27, 28, 29, 30, 32, 34, 36, 38, 40, 45, 50, or more amino acid residues on the C-terminus of the polypeptide. Recombinant sTNALP may include, e.g., amino acids 1 to 502 (18 to 502 when secreted), amino acids 1 to 501 (18 to 501 when secreted), amino acids 1 to 504 (18 to 504 when secreted), amino acids 1 to 505 (18-505 when secreted), or amino acids 1 to 502. Thus, the C-terminal end of the native ALP may be truncated by certain amino acids without affecting ALP activity.

In addition to the C-terminal GPI anchor, TNALP also has an N-terminal signal peptide sequence. The N-terminal signal peptide is present on the synthesized protein when it is synthesized, but cleaved from TNALP after translocation into the ER. The sALPs of the invention include both secreted (i.e., lacking the N-terminal signal) and non-secreted (i.e., having the N-terminal signal) forms thereof. One skilled in the art will appreciate that the position of the N-terminal signal peptide will vary in different alkaline phosphatases and may include, for example, the first 5, 8, 10, 11, 12, 13, 14, 15, 16, 17, 18, 19, 20, 21, 22, 23, 24, 25, 27, 30, or more amino acid residues on the N-terminus of the polypeptide. One of skill in the art can predict the position of a signal sequence cleavage site, e.g., by an appropriate computer algorithm such as that described in Bendtsen et al. (*J. Mol. Biol.* 340(4):783-795, 2004) and available on the Web at www.cbs.dtu.dk/services/SignalP/.

The present invention also includes sALP consensus sequences derived from the extracellular domain of ALP isozymes (e.g., TNALP, PALP, GCALP, IALP, etc.). Thus, similar to sTNALP discussed above, the present disclosure also provides other soluble human ALP isozymes, i.e., without the peptide signal, preferably comprising the extracellular domain of the ALPs. The sALPs of the invention also include polypeptide sequences satisfying a consensus sequence derived from the ALP extracellular domain of human ALP isozymes and of mammalian TNALP orthologs (human, mouse, rat, cow, cat, and dog) or a consensus derived from the ALP extracellular domain of just mammalian TNALP orthologs (human, mouse, rat, cow, cat, and dog). The sALPs of the invention also include those which satisfy similar consensus sequences derived from various combinations of these TNALP orthologs or human ALP isozymes. Such consensus sequences are given, for example, in WO 2008/138131.

sALPs of the present invention may include not only the wild-type sequence of the sALPs described above, but any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to these alkaline phosphatases (e.g., SEQ ID NOs: 1-24). Examples of mutations that may be introduced into an ALP sequence are described in US Publication No. 2013/0323244, hereby incorporated by reference in its entirety. A sALP may optionally be glycosylated at any appropriate one or more amino acid residues. In addition, an sALP may have at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to any of the sALPs described herein. A sALP may have 1, 2, 3, 4, 5, 6, 7, 8, 9, 10, or more additions, deletions, or substitutions relative to any of the sALPs described herein.

sALP Fusion Polypeptides

Any of the sALPs and linkers described herein may be combined in a sALP polypeptide, e.g., a sALP polypeptide of A-sALP-B, wherein each of A and B is absent or is an amino acid sequence of at least one amino acid. When present, A and/or B can be any linker described herein. In some sALP polypeptides, A is absent, B is absent, or A and B are both absent. The sALP polypeptides of the invention can optionally include an Fc region to provide an sALP fusion polypeptide, as described herein. The sALP polypeptide can optionally include a bone-targeting moiety, as described herein. In some sALP polypeptides, a linker, e.g., a flexible linker, may be included between the bone-targeting moiety and the sALP, such as a dipeptide sequence (e.g., leucine-lysine or aspartic acid-isoleucine). Further exemplary Fc regions, linkers, and bone-targeting moieties are described below.

Any of the sALPs, linkers, and Fc regions described herein may be combined in a fusion polypeptide, e.g., a recombinant fusion polypeptide, which includes the structure Z-sALP-Y-spacer-X-$W_n$-V, Z-$W_n$-X-spacer-Y-sALP-V, Z-sALP-Y-$W_n$-X-spacer-V, and Z-$W_n$-X-sALP-Y-spacer-V. In particular, the structure may be Z-sALP-Y-spacer-X-$W_n$-V or Z-$W_n$-X-spacer-Y-sALP-V. The sALP may be the full-length or functional fragments of ALPs, such as the soluble, extracellular domain of the ALP, as is described herein (e.g., TNALP, PALP, GCALP and IALP). Any one of X, Y, Z, and V and/or the spacer may be absent or an amino acid sequence of at least one amino acid. $W_n$ may be a bone-targeting moiety, e.g., having a series of consecutive Asp or Glu residues, in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50. The bone-targeting moiety, if present, may be positioned anywhere in the fusion polypeptide, e.g., at or near the N-terminal or C-terminal end, and/or in the linker region. For instance, the bone-targeting moiety is at the C-terminal end. sALP polypeptides and fusion polypeptides may not include a bone-targeting moiety.

sALP fusion polypeptides of the present invention may be of the structure hTNALP-Fc-$D_{10}$. In particular, sALP fusion polypeptides may include an amino acid sequence of SEQ ID NO: 19.

Useful spacers include, but are not limited to, polypeptides comprising a Fc, and hydrophilic and flexible polypeptides able to alleviate the repulsive forces caused by the presence of the terminal highly negatively charged peptide (e.g., $W_n$). For example, an sALP of the invention can be a fusion polypeptide including an Fc region of an immunoglobulin at the N-terminal or C-terminal domain. An immunoglobulin molecule has a structure that is well known in the art. It includes two light chains (~23 kD each) and two heavy chains (~50-70 kD each) joined by inter-chain disulfide bonds. Immunoglobulins are readily cleaved proteolytically (e.g., by papain cleavage) into Fab (containing the light chain and the VH and CH1 domains of the heavy chain) and Fc (containing the CH2 and CH3 domains of the heavy chain, along with adjoining sequences). Useful Fc fragments as described herein include the Fc fragment of any immunoglobulin molecule, including IgG, IgM, IgA, IgD, or IgE, and their various subclasses (e.g., IgG-1, IgG-2, IgG-3, IgG-4, IgA-1, IgA-2), from any mammal (e.g., human). For instance, the Fc fragment is human IgG-1. The Fc fragments of the invention may include, for example, the CH2 and CH3 domains of the heavy chain and any portion of the hinge region. The Fc region may optionally be glycosylated at any appropriate one or more amino acid residues known to those skilled in the art. In particular, the Fc fragment of the fusion polypeptide has the amino acid sequence of SEQ ID NO: 25, or has at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to SEQ ID NO: 25. Engineered, e.g., non-naturally occurring, Fc regions may be utilized in the methods of the invention, e.g., as described in International Application Pub. No. WO2005/007809, which is hereby incorporated by reference. An Fc fragment as described herein may have 1, 2, 3, 4, 5, 6, 7, 8, 9, 10, 11, 12, 13, 14, 15, 16, 17, 18, 19, 20, 25, 30, 35, 40, 50, or more additions, deletions, or substitutions relative to any of the Fc fragments described herein.

The sALP fusion polypeptides described herein may include a peptide linker region between the Fc fragment. In addition, a peptide linker region may be included between the Fc fragment and the optional bone-targeting moiety. The linker region may be of any sequence and length that allows the sALP to remain biologically active, e.g., not sterically hindered. Exemplary linker lengths are between 1 and 200 amino acid residues, e.g., 1-5, 6-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, or 191-200 amino acid residues. For instance, linkers include or consist of flexible portions, e.g., regions without significant fixed secondary or tertiary structure. Exemplary flexible linkers are glycine-rich linkers, e.g., containing at least 50%, 60%, 65%, 70%, 75%, 80%, 85%, 90%, 95%, or even 100% glycine residues. Linkers may also contain, e.g., serine residues. In some cases, the amino acid sequence of linkers consists only of glycine and serine residues. A linker may optionally be glycosylated at any appropriate one or more amino acid residues. Additionally, a linker as described herein may include any other sequence or moiety, attached covalently or non-covalently. The linker may also be absent, in which the Fc fragment and the sALP are fused together directly, with no intervening residues. Certain Fc-sALP or sALP-Fc fusion polypeptides may be viewed, according to the present disclosure, either as 1) having no linker, or as 2) having a linker which corresponds to a portion of the sALP. For example, Fc fused directly to hsTNALP (1-502) may be viewed, e.g., either as having no linker, in which the hsTNALP is amino acids 1-502, or as having a 17-amino acid linker, in which the hsTNALP (18-502).

Additional amino acid residues can be introduced into the polypeptide according to the cloning strategy used to produce the fusion polypeptides. For instance, the additional amino acid residues do not provide an additional GPI anchoring signal so as to maintain the polypeptide in a soluble form. Furthermore, any such additional amino acid residues, when incorporated into the polypeptide of the invention, do not provide a cleavage site for endoproteases of the host cell. The likelihood that a designed sequence would be cleaved by the endoproteases of the host cell can be predicted as described, e.g., by Ikezawa (*Biol. Pharm. Bull.* 25:409-417, 2002).

The sALPs and sALP fusion polypeptides of the invention may be associated into dimers or tetramers. For example, two sALP-Fc monomers can covalently be linked through two disulfide bonds located in the hinge regions of the Fc fragments. Additionally, the polypeptide or fusion polypeptide of the invention (e.g., a sALP polypeptide or fusion polypeptide) may be glycosylated or PEGylated.

Production of Nucleic Acids and Polypeptides

The nucleic acids encoding sALPs and sALP fusion polypeptides of the invention can be produced by any method known in the art. Typically, a nucleic acid encoding the desired fusion polypeptide is generated using molecular cloning methods, and is generally placed within a vector, such as a plasmid or virus. The vector is used to transform the nucleic acid into a host cell appropriate for the expression of the fusion polypeptide. Representative methods are disclosed, for example, in Maniatis et al. (Cold Springs Harbor Laboratory, 1989). Many cell types can be used as appropriate host cells, although mammalian cells are preferable because they are able to confer appropriate post-translational modifications. Host cells of the present invention may include, e.g., Chinese Hamster Ovary (CHO) cell, L cell, C127 cell, 3T3 cell, BHK cell, COS-7 cell or any other suitable host cell known in the art. For example, the host cell is a Chinese Hamster Ovary (CHO) cell (e.g., a CHO-DG44 cell).

The sALPs and sALP fusion polypeptides can be produced under any conditions suitable to effect expression of the sALP polypeptide in the host cell. Such conditions include appropriate selection of a media prepared with components such as a buffer, bicarbonate and/or HEPES, ions like chloride, phosphate, calcium, sodium, potassium, magnesium, iron, carbon sources like simple sugars, amino acids, potentially lipids, nucleotides, vitamins and growth factors like insulin; regular commercially available media like alpha-MEM, DMEM, Ham's-F12, and IMDM supplemented with 2-4 mM L-glutamine and 5% Fetal bovine serum; regular commercially available animal protein free media like Hyclone™ SFM4CHO, Sigma CHO DHFR⁻, Cambrex POWER™ CHO CD supplemented with 2-4 mM L-glutamine. These media are desirably prepared without thymidine, hypoxanthine and L-glycine to maintain selective pressure, allowing stable protein-product expression.

Pharmaceutical Compositions and Formulations

A composition of the present invention (e.g., including a sALP or sALP fusion polypeptide, such as TNALP or TNALP fusion polypeptides, for example SEQ ID NO: 19, such as STRENSIQ™) can be administered by a variety of methods known in the art. As will be appreciated by the skilled artisan, the route and/or mode of administration will vary depending upon the desired results. The route of administration can depend on a variety of factors, such as the environment and therapeutic goals. In particular, the polypeptides and fusion polypeptides described herein can be administration by any route known in the art, e.g., subcutaneous (e.g., by subcutaneous injection), intravenously, orally, nasally, intramuscularly, sublingually, intrathecally, or intradermally. By way of example, pharmaceutical compositions of the invention can be in the form of a liquid, solution, suspension, pill, capsule, tablet, gelcap, powder, gel, ointment, cream, nebulae, mist, atomized vapor, aerosol, or phytosome.

Timing of Treatment

The compositions described herein, including a sALP or sALP fusion polypeptide (such as TNALP, for example SEQ ID NO: 19, such as STRENSIQ™), can be administered prior to a cranial surgery, e.g., a cranial vault remodeling procedure (e.g., four months or more prior, 3 months prior, 2 months prior, 1 month prior, 4 weeks prior, 3 weeks prior, 2 weeks prior, 1 week prior, 6 days prior, 5 days prior, 4 days prior, 3 days prior, 2 days prior, 1 day prior, within less than 24 hours prior to the cranial surgery, e.g., the cranial vault remodeling procedure). Furthermore, the compositions can be administered after a cranial surgery, e.g., a cranial vault remodeling procedure (e.g., four months or more after, 3 months after, 2 months after, 1 month after, 4 weeks after, 3 weeks after, 2 weeks after, 1 week after, 6 days after, 5 days after, 4 days after, 3 days after, 2 days after, 1 day after, within less than 24 hours after the cranial surgery, e.g., the cranial vault remodeling procedure). A sALP composition can be administered prior to a cranial surgery, e.g., a cranial vault remodeling procedure, for instance, if symptoms of craniosynostosis are considered manageable. Administration of a sALP (such as TNALP, for example SEQ ID NO: 19, such as STRENSIQ™) composition prior to a cranial vault remodeling procedure can also be performed, e.g., to allow for proper fusion of the cranial sutures or prevent immature fusion of the cranial sutures. Alternatively, if the patient exhibits symptoms of craniosynostosis (e.g., increased ICP) that require a cranial vault remodeling procedure prior to administration of a sALP, the sALP can be administered after the cranial vault remodeling procedure to allow for, e.g., relief of increased ICP, proper fusion of the cranial sutures, and/or proper growth of the skull.

Dosage

Any amount of a pharmaceutical composition (e.g., including a sALP or sALP fusion polypeptide (such as TNALP or TNALP fusion polypeptides, for example SEQ ID NO: 19, such as STRENSIQ™)) can be administered to a patient, such as patient (e.g., a HPP patient) with craniosynostosis. The dosages will depend on many factors including the mode of administration and the age of the patient. Typically, the amount of the composition (e.g., a sALP or sALP fusion polypeptide) contained within a single dose will be an amount that is effective to treat a condition (e.g., craniosynostosis) as described herein without inducing significant toxicity.

For example, the sALP polypeptides (such as TNALP, for example SEQ ID NO: 19, such as STRENSIQ™) described herein can be administered to patients in individual doses ranging, e.g., from 0.01 mg/kg to 500 mg/kg (e.g., from 0.05 mg/kg to 500 mg/kg, from 0.1 mg/kg to 20 mg/kg, from 5 mg/kg to 500 mg/kg, from 0.1 mg/kg to 100 mg/kg, from 10 mg/kg to 100 mg/kg, from 0.1 mg/kg to 50 mg/kg, 0.5 mg/kg to 25 mg/kg, 1.0 mg/kg to 10 mg/kg, 1.5 mg/kg to 5 mg/kg, or 2.0 mg/kg to 3.0 mg/kg) or from 1 µg/kg to 1,000 µg/kg (e.g., from 5 µg/kg to 1,000 µg/kg, from 1 µg/kg to 750 µg/kg, from 5 µg/kg to 750 µg/kg, from 10 µg/kg to 750 µg/kg, from 1 µg/kg to 500 µg/kg, from 5 µg/kg to 500 µg/kg, from 10 µg/kg to 500 µg/kg, from 1 µg/kg to 100 µg/kg, from 5 µg/kg to 100 µg/kg, from 10 µg/kg to 100 µg/kg, from 1 µg/kg to 50 µg/kg, from 5 µg/kg to 50 µg/kg, or from 10 µg/kg to 50 µg/kg).

Exemplary doses of a sALP include, e.g., 0.01, 0.05, 0.1, 0.5, 1, 2, 2.5, 5, 10, 20, 25, 50, 100, 125, 150, 200, 250, or 500 mg/kg; or 1, 2, 2.5, 5, 10, 20, 25, 50, 100, 125, 150, 200, 250, 500, 750, 900, or 1,000 µg/kg. For all dosages or ranges recited herein, the term "about" may be used to modify these dosages by ±10% of the recited values or range endpoints. In particular, compositions (e.g., including sALP (such as TNALP, for example SEQ ID NO: 19, such as STRENSIQ™)) in accordance with the present disclosure can be administered to patients in doses ranging from about 0.001 mg/kg/day to about 500 mg/kg/day, about 0.01 mg/kg/day to about 100 mg/kg/day, or about 0.01 mg/kg/day to about 20 mg/kg/day. For example, the sALP compositions (such as TNALP, for example SEQ ID NO: 19, such as STRENSIQ™) can be administered to patients in a weekly dosage ranging, e.g., from about 0.5 mg/kg/week to about 140 mg/kg/week, e.g., about 0.8 mg/kg/week to about 50 mg/kg/week, or about 1 mg/kg/week to about 10 mg/kg/week (e.g., 6 mg/kg/week). The dosage will be adapted by the clinician in accordance with conventional factors such as the extent of the disease and different parameters from the patient.

Dosages of compositions including sALPs and sALP fusion polypeptides (such as TNALP or TNALP fusion polypeptides, for example SEQ ID NO: 19, such as STRENSIQ™) may be provided in either a single or multiple dosage regimens. Doses can be administered, e.g., hourly, bihourly, daily, bidaily, twice a week, three times a week, four times a week, five times a week, six times a week, weekly, biweekly, monthly, bimonthly, or yearly. Alternatively, doses can be administered, e.g., twice, three times, four times, five times, six times, seven times, eight times, nine times, 10 times, 11 times, or 12 times per day. In particular, the dosing regimen is once weekly. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), or month(s), or even for the remaining lifespan of the patient. The amount, frequency, and duration of dosage will be adapted by the clinician in accordance with conventional factors such as the extent of the disease and different parameters from the patient.

Nucleic acids encoding sALPs and sALP fusion polypeptides can be administered according the formulations described herein to a patient in dosages suitable for gene therapy. The amount of the nucleic acids administered will depend on a number of factors known to those skilled in the art, including: the length and nature of the nucleic acid, the vector (e.g., viral or non-viral) used, the activity of the polypeptide encoded, the presence of excipients, the route and method of administration, and the general condition and fitness of the patient. Exemplary dosages and routes of administration are described, e.g., in Melman et al. (*Isr. Med. Assoc. J.* 9:143-146, 2007; describing the intrapenile injection of 0.5 mg to 7.5 mg of a human cDNA in a plasmid for treating erectile dysfunction), Powell et al. (*Circulation* 118:58-65, 2008; describing the intramuscular injection of 0.4 mg to 4.0 mg of a hepatocyte growth factor plasmid to treat critical limb ischemia, Waddill et al. (*AJR Am. J. Roentgenol.* 169:63-67, 1997; describing the CT-guided intra-tumoral injection of 0.01 mg to 0.25 mg of plasmid DNA encoding an MHC antigen to treat melanoma), Kastrup et al. (*J. Am. Coll. Cardiol.* 45:982-988, 2005; describing the intramyocardial injection of 0.5 mg of a VEGF plasmid to treat severe angina pectoris), and Romero et al. (*Hum. Gene. Ther.* 15:1065-1076, 2004; describing the intramuscular injection of 0.2 mg to 0.6 mg of a plasmid to treat Duchenne/Becker muscular dystrophy), each of which is hereby incorporated by reference.

Nucleic acids encoding sALPs and sALP fusion polypeptides can be administered to the patient at a dose in the range from, e.g., 0.01 mg to 100 mg (e.g., from 0.05 mg to 50 mg, 0.1 mg to 10 mg, 0.3 mg to 3 mg, or about 1 mg) of nucleic acid. The total volume at which the nucleic acid can be administered will depend on its concentration, and can range from, e.g., 1 µL to 10 mL (e.g. from 10 µL to 1 mL, 50 µL to 500 µL, 70 µL to 200 µL, 90 µL to 150 µL, or 100 µL to 120 µL). The nucleic acids can be administered, e.g., hourly, bihourly, daily, bidaily, twice a week, three times a week, four times a week, five times a week, six times a week, weekly, biweekly, monthly, bimonthly, or yearly. Alternatively, the nucleic acids can be administered, e.g., twice, three times, four times, five times, six times, seven times, eight times, nine times, 10 times, 11 times, or 12 times per day. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day, weeks, or months, or even for the remaining lifespan of the patient.

These are guidelines, since the actual dose should be carefully selected and titrated by an attending physician or nutritionist based upon clinical factors unique to each patient. The optimal periodic dose will be determined by methods known in the art and will be influenced by factors such as the age of the patient, as indicated above, and other clinically relevant factors. In addition, patients may be taking medications for other diseases or conditions. The other medications may be continued during the time that a polypeptide or nucleic acid of the invention is given to the patient, but it is advisable in such cases to begin with low doses to determine if adverse side effects are experienced.

For example, a sALP or sALP fusion polypeptide (such as TNALP or TNALP fusion polypeptides, for example SEQ ID NO: 19, such as STRENSIQ™) may be formulated as a solution for injection, which is a clear, colorless to slightly yellow, aqueous solution, pH 7.4. The sALP or sALP polypeptide may be formulated at a concentration of 12 mg/0.3 mL, 18 mg/0.45 mL, 28 mg/0.7 mL, 40 mg/1 ml, or 80 mg/0.8 mL. In particular, the composition may be formulated as a 40 mg/ml solution for injection, in which each ml of solution contains 40 mg of sALP or sALP polypeptide (e.g., each vial contains 0.3 ml solution and 12 mg of sALP (40 mg/ml), each vial contains 0.45 ml solution and 18 mg of sALP (40 mg/ml), each vial contains 0.7 ml solution and 28 mg of sALP (40 mg/ml), or each vial contains 1.0 ml solution and 40 mg of asfotase alfa (40 mg/ml)). A sALP or sALP polypeptide (such as TNALP or TNALP fusion polypeptides, for example SEQ ID NO: 19, such as STRENSIQ™) may be formulated as a solution for injection at a concentration of 100 mg/ml, in which each 1 ml of solution contains 100 mg of sALP or sALP polypeptide (e.g., each vial contains 0.8 ml solution and 80 mg of asfotase alfa (100 mg/ml)).

For example, the recommended dosage of a sALP or sALP fusion polypeptide (such as TNALP or TNALP fusion polypeptides, for example SEQ ID NO: 19, such as STRENSIQ™) is 2 mg/kg of body weight administered subcutaneously three times per week, or a dosage regimen of 1 mg/kg of body weight administered subcutaneously six times per week. Additional dosage information is provided below (Table 1).

TABLE 1

Dosing chart for a sALP or sALP fusion polypeptide
(SEQ ID NO: 19, such as STRENSIQ ™).

| Body Weight (kg) | If injecting 3x per week | | | If injecting 6x per week | | |
|---|---|---|---|---|---|---|
| | Dose to be injected | Volume to be injected | Vial type used for injection | Dose to be injected | Volume to be injected | Vial type used for injection |
| 3 | 6 mg | 0.15 ml | 0.3 ml | | | |
| 4 | 8 mg | 0.20 ml | 0.3 ml | | | |
| 5 | 10 mg | 0.25 ml | 0.3 ml | | | |
| 6 | 12 mg | 0.30 ml | 0.3 ml | 6 mg | 0.15 ml | 0.3 ml |
| 7 | 14 mg | 0.35 ml | 0.45 ml | 7 mg | 0.18 ml | 0.3 ml |
| 8 | 16 mg | 0.40 ml | 0.45 ml | 8 mg | 0.20 ml | 0.3 ml |
| 9 | 18 mg | 0.45 ml | 0.45 ml | 9 mg | 0.23 ml | 0.3 ml |
| 10 | 20 mg | 0.50 ml | 0.7 ml | 10 mg | 0.25 ml | 0.3 ml |
| 11 | 22 mg | 0.55 ml | 0.7 ml | 11 mg | 0.28 ml | 0.3 ml |
| 12 | 24 mg | 0.60 ml | 0.7 ml | 12 mg | 0.30 ml | 0.3 ml |
| 13 | 26 mg | 0.65 ml | 0.7 ml | 13 mg | 0.33 ml | 0.45 ml |
| 14 | 28 mg | 0.70 ml | 0.7 ml | 14 mg | 0.35 ml | 0.45 ml |
| 15 | 30 mg | 0.75 ml | 1 ml | 15 mg | 0.38 ml | 0.45 ml |
| 16 | 32 mg | 0.80 ml | 1 ml | 16 mg | 0.40 ml | 0.45 ml |
| 17 | 34 mg | 0.85 ml | 1 ml | 17 mg | 0.43 ml | 0.45 ml |
| 18 | 36 mg | 0.90 ml | 1 ml | 18 mg | 0.45 ml | 0.45 ml |
| 19 | 38 mg | 0.95 ml | 1 ml | 19 mg | 0.48 ml | 0.7 ml |
| 20 | 40 mg | 1.00 ml | 1 ml | 20 mg | 0.50 ml | 0.7 ml |
| 25 | 50 mg | 0.50 ml | 0.8 ml | 25 mg | 0.63 ml | 0.7 ml |
| 30 | 60 mg | 0.60 ml | 0.8 ml | 30 mg | 0.75 ml | 1 ml |
| 35 | 70 mg | 0.70 ml | 0.8 ml | 35 mg | 0.88 ml | 1 ml |
| 40 | 80 mg | 0.80 ml | 0.8 ml | 40 mg | 1.00 ml | 1 ml |
| 50 | | | | 50 mg | 0.50 ml | 0.8 ml |
| 60 | | | | 60 mg | 0.60 ml | 0.8 ml |
| 70 | | | | 70 mg | 0.70 ml | 0.8 ml |
| 80 | | | | 80 mg | 0.80 ml | 0.8 ml |
| 90 | | | | 90 mg | 0.90 ml | 0.8 ml (x2) |
| 100 | | | | 100 mg | 1.00 ml | 0.8 ml (x2) |

Formulations

The compositions including sALPs and sALP fusion polypeptides (such as TNALP or TNALP fusion polypeptides, for example SEQ ID NO: 19, such as STRENSIQ™) can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). For instance, a sALP composition (e.g., TNALP, for example SEQ ID NO: 19, such as STRENSIQ™) can be formulated, for example, as a buffered solution at a suitable concentration and suitable for storage at 2-8° C. (e.g., 4° C.). A composition can also be formulated for storage at a temperature below 0° C. (e.g., −20° C. or −80° C.). A composition can further be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, the compositions described herein may be stable in storage for at least 1 year at 2-8° C. (e.g., 4° C.).

The compositions including sALPs and sALP fusion polypeptides (such as TNALP or TNALP fusion polypeptides, for example SEQ ID NO: 19, such as STRENSIQ™) can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application.

For example, compositions intended for systemic or local delivery can be in the form of injectable or infusible solutions. Accordingly, the compositions (e.g., a sALP polypeptide or sALP fusion polypeptide, such as TNALP or TNALP fusion polypeptides, for example SEQ ID NO: 19, such as STRENSIQ™) can be formulated for administration by a parenteral mode (e.g., subcutaneous, intravenous, intraperitoneal, or intramuscular injection). "Parenteral administration," "administered parenterally," and other grammatically equivalent phrases, as used herein, refer to modes of administration other than enteral and topical administration, usually by injection, and include, without limitation, subcutaneous, intradermal, intravenous, intranasal, intraocular, pulmonary, intramuscular, intra-arterial, intrathecal, intracapsular, intraorbital, intracardiac, intradermal, intrapulmonary, intraperitoneal, transtracheal, subcuticular, intraarticular, subcapsular, subarachnoid, intraspinal, epidural, intracerebral, intracranial, intracarotid, and intrasternal injection and infusion.

The compositions including sALPs and sALP fusion polypeptides (such as TNALP or TNALP fusion polypeptides, for example SEQ ID NO: 19, such as STRENSIQ™) can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

Compositions including sALPs and sALP fusion polypeptides (such as TNALP or TNALP fusion polypeptides, for example SEQ ID NO: 19, such as STRENSIQ™) may also be formulated with a carrier that will protect the composition (e.g., a sALP polypeptide or sALP fusion polypeptide) against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

When compositions are to be used in combination with a second active agent, the compositions can be co-formulated with the second agent, or the compositions can be formulated separately from the second agent formulation. For example, the respective pharmaceutical compositions can be mixed, e.g., just prior to administration, and administered together or can be administered separately, e.g., at the same or different times.

Compositions including sALPs and sALP fusion polypeptides (such as TNALP or TNALP fusion polypeptides, for example SEQ ID NO: 19, such as STRENSIQ™) may be formulated for administration to a patient or, if administered to a fetus, to a female carrying such fetus, along with intravenous gamma globulin therapy (IVIG), plasmapheresis, plasma replacement, or plasma exchange.

Carriers/Vehicles

Preparations containing a sALP or sALP fusion polypeptide (such as TNALP or TNALP fusion polypeptides, for example SEQ ID NO: 19, such as STRENSIQ™) may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. For example, the pharmaceutically acceptable carrier may include sodium chloride and/or sodium phosphate, in which the composition includes, e.g., about 150 mM sodium chloride and/or about 25 mM sodium phosphate, pH 7.4.

Intravenous vehicles may include fluid and nutrient replenishers, electrolyte replenishers, such as those based upon Ringer's dextrose, and the like. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable carriers is available in Remington's Pharmaceutical Sciences (Mack Pub. Co., N.J. 1991).

Gene Therapy

The sALP and sALP fusion polypeptides (such as TNALP or TNALP fusion polypeptides, for example SEQ ID NO: 19, such as STRENSIQ™) could also be delivered through gene therapy, where an exogenous nucleic acid encoding the proteins is delivered to tissues of interest and expressed in vivo. Gene therapy methods are discussed, e.g., in Verme et al. (*Nature* 389:239-242, 1997), Yamamoto et al. (*Molecular Therapy* 17:S67-S68, 2009), and Yamamoto et al., (*J. Bone Miner. Res.* 26:135-142, 2011), each of which is hereby incorporated by reference. Both viral and non-viral vector systems can be used. The vectors may be, for example, plasmids, artificial chromosomes (e.g., bacterial, mammalian, or yeast artificial chromosomes), virus or phage vectors provided with an origin of replication, and optionally, a promoter for the expression of the nucleic acid encoding the viral polypeptide and optionally, a regulator of the promoter. The vectors may contain one or more selectable marker genes, for example, an ampicillin or kanamycin resistance gene in the case of a bacterial plasmid or a resistance gene for a fungal vector. Vectors may be used in in vitro, for example, for the production of DNA, RNA, or the viral polypeptide, or may be used to transfect or transform a host cell, for example, a mammalian host cell, e.g., for the production of the viral polypeptide encoded by the vector. The vectors may also be adapted to be used in vivo, for example, in a method of vaccination or gene therapy.

Examples of suitable viral vectors include, retroviral, lentiviral, adenoviral, adeno-associated viral, herpes viral, including herpes simplex viral, alpha-viral, pox viral, such as Canarypox and vaccinia-viral based systems. Gene transfer techniques using these viruses are known in the art. Retrovirus vectors, for example, may be used to stably integrate the nucleic acids of the invention into the host genome. Replication-defective adenovirus vectors by contrast remain episomal and therefore allow transient expression. Vectors capable of driving expression in insect cells (e.g., baculovirus vectors), in human cells, yeast, or in bacteria may be employed in order to produce quantities of the viral polypeptide(s) encoded by the nucleic acids of the invention, for example, for use in subunit vaccines or in immunoassays. Useful gene therapy methods include those described in WO 06/060641, U.S. Pat. No. 7,179,903 and WO 01/36620 (each of which is hereby incorporated by reference), which use an adenovirus vector to target a nucleic acid of interest to hepatocytes as protein producing cells.

In an additional example, a replication-deficient simian adenovirus vector may be used as a live vector. These viruses contain an E1 deletion and can be grown on cell lines that are transformed with an E1 gene. Examples of these replication-deficient simian adenovirus vectors are described in U.S. Pat. No. 6,083,716 and WO 03/046124 (each of which is hereby incorporated by reference). These vectors can be manipulated to insert a nucleic acid of the invention, such that the encoded viral polypeptide(s) may be expressed.

Promoters and other expression regulatory signals may be selected to be compatible with the host cell for which expression is designed. For example, mammalian promoters include the metallothionein promoter, which can be induced in response to heavy metals such as cadmium, and the β-actin promoter. Viral promoters, such as the SV40 large T antigen promoter, human cytomegalovirus (CMV) immediate early (1E) promoter, rous sarcoma virus LTR promoter, adenovirus promoter, or a HPV promoter, particularly the HPV upstream regulatory region (URR) may also be used. All these promoters, as well as additional promoters, are well-described in the art.

The nucleic acid molecules described herein may also be administered using non-viral based systems. For example, these administration systems include microsphere encapsulation, poly(lactide-co-glycolide), nanoparticle, and liposome-based systems. Non-viral based systems also include techniques facilitating the delivery of "naked" polynucleotides (such as electroporation, "gene gun" delivery and various other techniques used for the introduction of polynucleotides).

The introduced polynucleotide can be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome.

The following examples are intended to illustrate, rather than limit, the claimed invention.

EXAMPLES

Example 1. Overview of Case Series

Four pediatric patients with hypophosphatasia (HPP) and craniosynostosis were treated initially. The average age at presentation to our craniofacial team was 38.2 months. Each patient was treated with a soluble alkaline phosphatase (sALP) composition according to an ongoing, approved clinical trial with agent ENB-0040 (STRENSIQ™ (asfotase alfa); SEQ ID NO: 19). One patient received the sALP composition preoperatively, and three patients received the sALP composition postoperatively. All four patients presented symptoms of altered neurological function and underwent neurodiagnostic imaging to confirm the presence of craniosynostosis. Two patients were from the same family, both patients having infantile HPP associated with craniosynostosis and a familial history of HPP, with four male cousins affected by HPP.

Example 2. Craniosynostosis Patient 1

Patient 1 was a 3 year and 9 month old male that was initially presented to an endocrinology medical service at the age of 2 years and 3 months. His medical history included HPP, craniosynostosis, restrictive lung disease, respiratory infections, failure to thrive, and multiple fractures. He was admitted to the hospital for management of acute exacerbation of a chronic respiratory illness. Consultation with our craniofacial team was requested to evaluate the clinical findings of dolichocephaly and ridging over the left coronal suture.

Figure 1B:
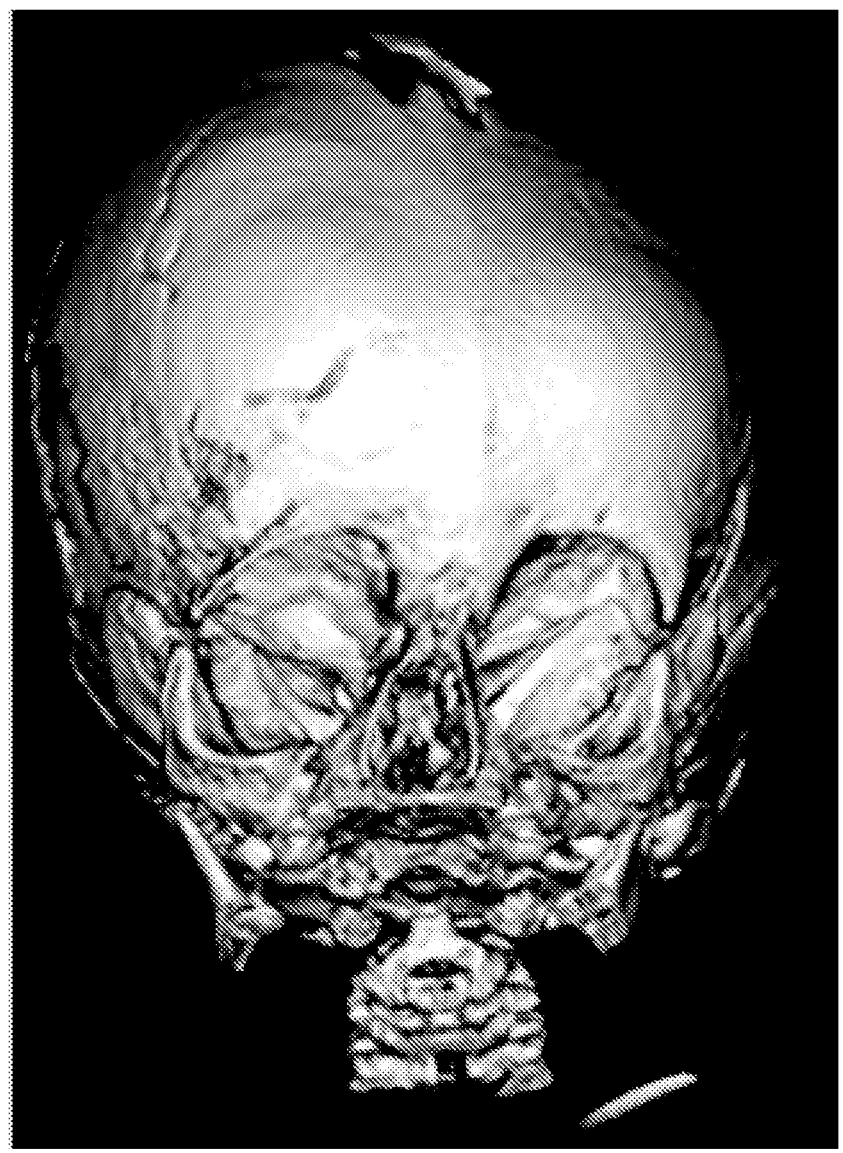

Upon clinical evaluation, the patient also presented symptoms of irritability, intermittent emesis, headaches, an asymmetrical cranial base, facial scoliosis, and bilateral papilledema. As part of a clinical trial, the patient was awaiting treatment with the sALP composition, ENB-0040 (asfotase alfa; SEQ ID NO: 19). Diagnostic radiographic imaging with three dimensional (3D) head computerized tomography (CT) scan revealed left coronal and sagittal craniosynostosis, calvarial thinning, dysplasia of the right frontal lobe, and venous anomalies including congenital absence of the right sigmoid sinus (FIGS. 1A and 1B).

Due to these symptoms, a fronto-orbital advancement with cranial vault reconstruction was performed to reduce suspected intracranial hypertension and to correct the anatomical deformity. Allograft material (Grafton DBM in Flex and Putty forms, BioHorizons IPH, Inc.) was used to augment bone formation. The patient tolerated the procedure well with no complications noted.

Figure 2A:
FIGS. 2A-2B are images showing a CT scan of a patient (i.e., Patient 1) with craniosynostosis prior to and after surgery.

Three weeks after surgery, the patient started treatment with the sALP composition ENB-0040 (asfotase alfa; SEQ ID NO: 19) at a dosage of 1 mg/kg given subcutaneously six times a week. One year after the surgery, the patient was well with resolution of his papilledema and symptoms attributed to increased ICP including headache, irritability, and vomiting. This patient showed improvement in his body bone mineralization, tooth eruption, increased weight gain, and overall health. The cranial vault remodeling procedure resulted in increased space in the basal cisterns and foramen magnum with less crowding at the craniovertebral junction (FIG. 2A, pre-operative sagittal CT scan).

Figure 2B:
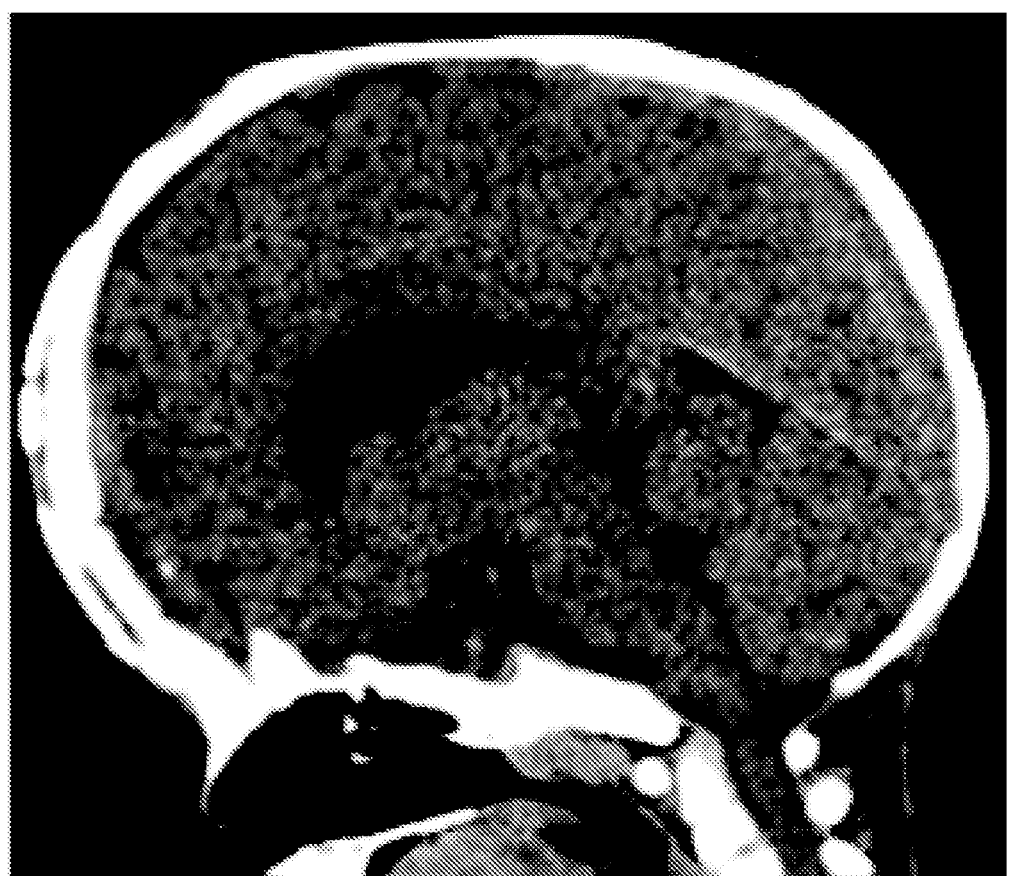

The lambdoid suture tends to close early in HPP, thus preventing normal growth of the posterior fossa and potentially causing herniation of the cerebellar tonsils with a resulting Chiari Type I malformation. As seen in Patient 1, the Chiari Type I malformation can resolve following cranial vault remodeling and expansion, a phenomenon that is described in other forms of craniosynostosis (FIG. 2B, sagittal CT scan, taken one year post-operatively).

Example 3. Craniosynostosis Patient 2

Patient 2 was the 5 year and 6 month old sister of Patient 1. Patient 2 exhibited the symptoms of malformed head shape, headaches, nystagmus, chronic optic nerveedema, and decreased visual acuity. She was previously evaluated in her home country with concerns regarding her genetic predisposition to HPP and the presence of a complex craniosynostosis.

Figure 3A:
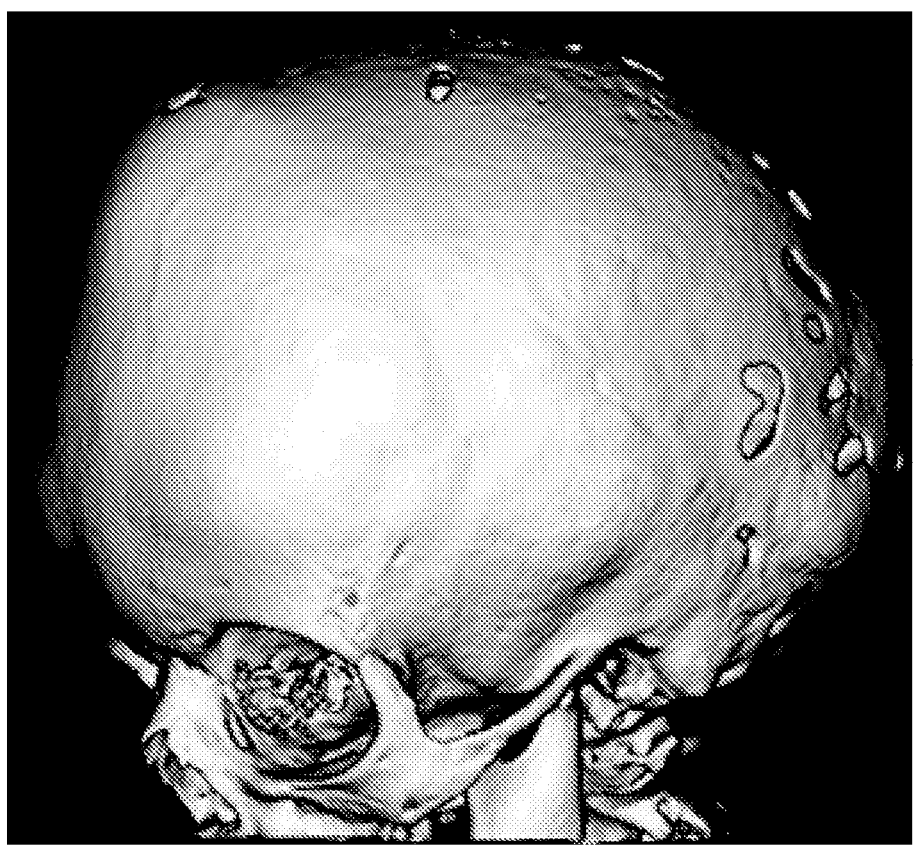
FIGS. 3A-3C are images showing a CT scan of a patient (i.e., Patient 2) with craniosynostosis prior to and after surgery.
Figure 3B:
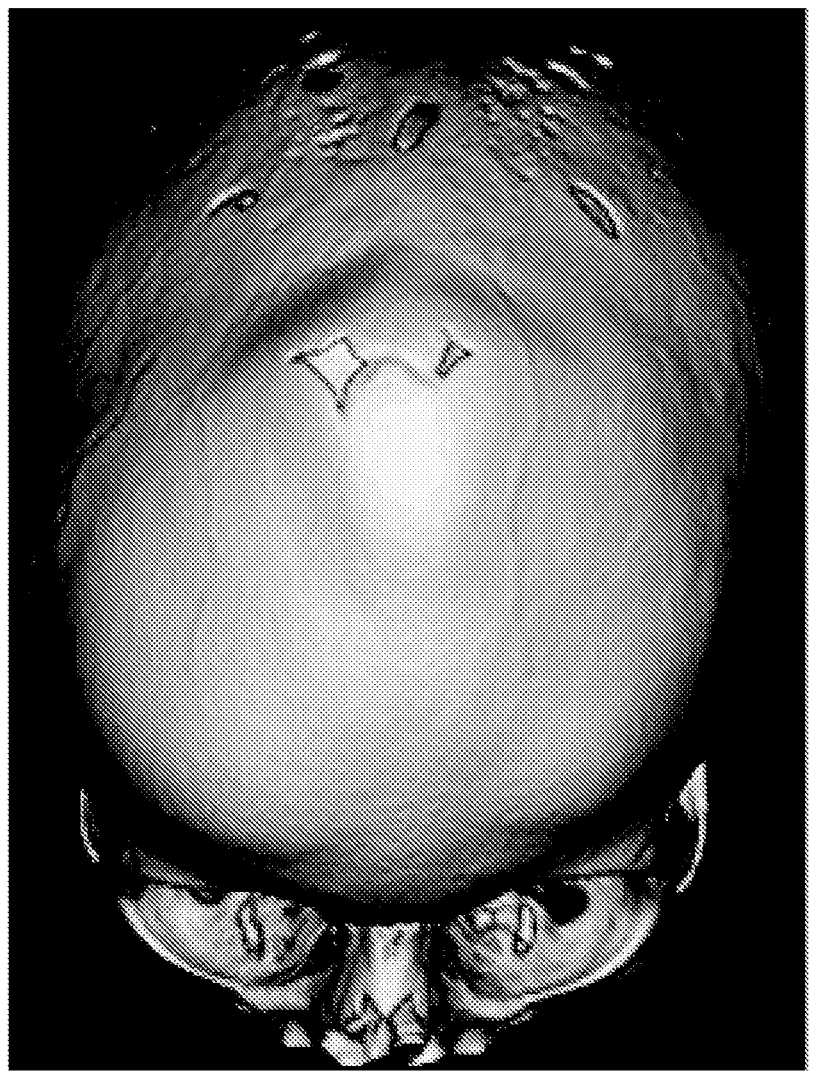

During clinical evaluation, the patient's head circumference was 47 cm (microcephalic for her age), with a significant bony prominence over the bregma with persistence of an open anterior fontanelle that was tense on palpation. Radiography evaluation by 3D CT scanning revealed abnormal calvarial morphology with marked scalloping of the inner table with absence of the extraaxial spaces and complete obliteration of the sagittal and left coronal suture lines. These results were concerning for chronically elevated ICP (FIGS. 3A and 3B). Given the chronic changes secondary to untreated HPP, healing of bone postoperatively was a concern.

Figure 3C:
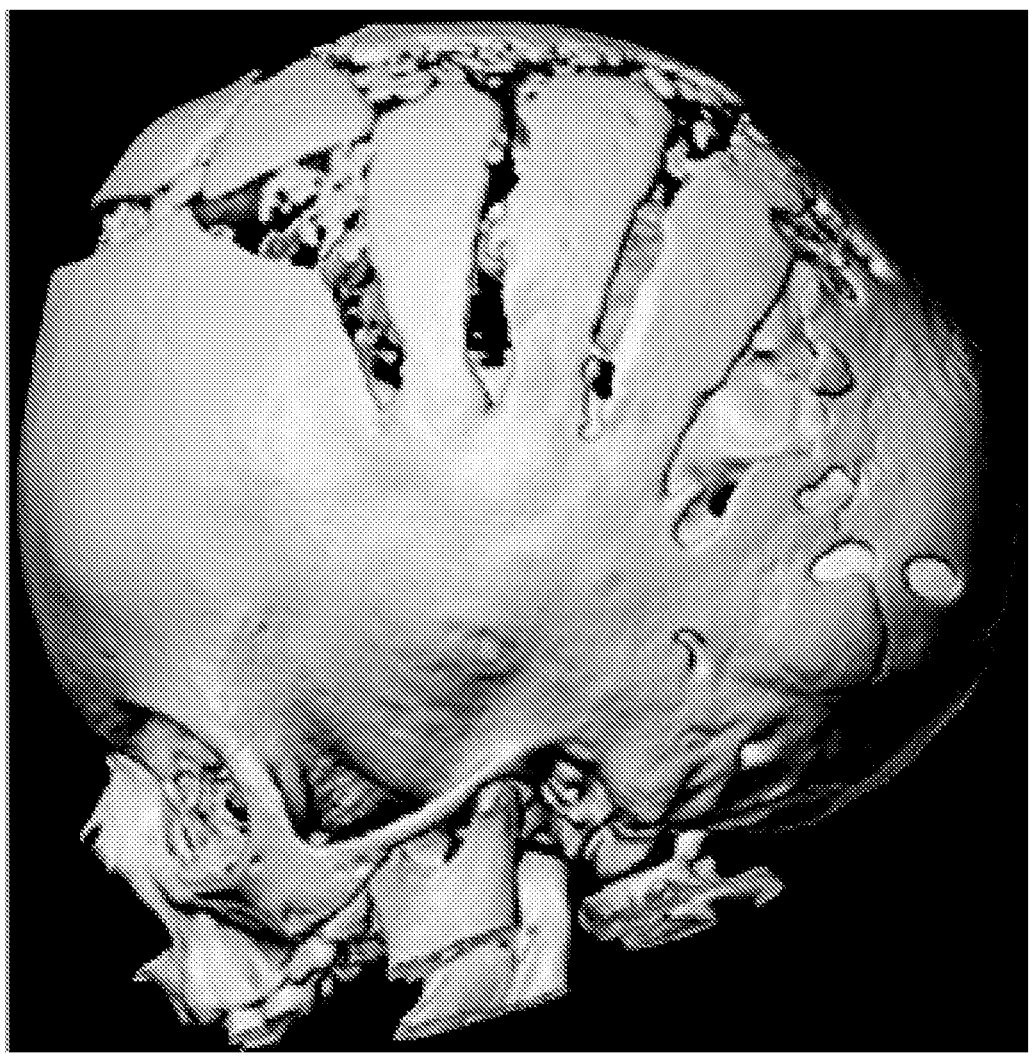

The patient underwent an open cranial vault reconstruction with identification of multiple areas of calcified dura. In particular, the patient underwent multiple barrel stave osteotomies for cranial vault expansion without any perioperative complications, such as cerebrospinal fluid (CSF) leaks, associated with the calcified dura. Seven months following surgery, a 3D CT scan of the patient's head demonstrated improved bone growth of the calvaria (FIG. 3C). Although radiographically left coronal craniosynostosis was evident, clinically the patient did not exhibit asymmetrical orbital findings of unilateral coronal craniosynostosis, such as harlequin deformity. Therefore, barrel stave osteotomies were completed rather than modification of the frontoorbital complex. Due to the complexity of the patient and high risk of CSF leak because of the calcified dura, this course of cranial vault remodeling was chosen instead of a frontoorbital cranioplasty with the osteotomies.

Figure 4A:
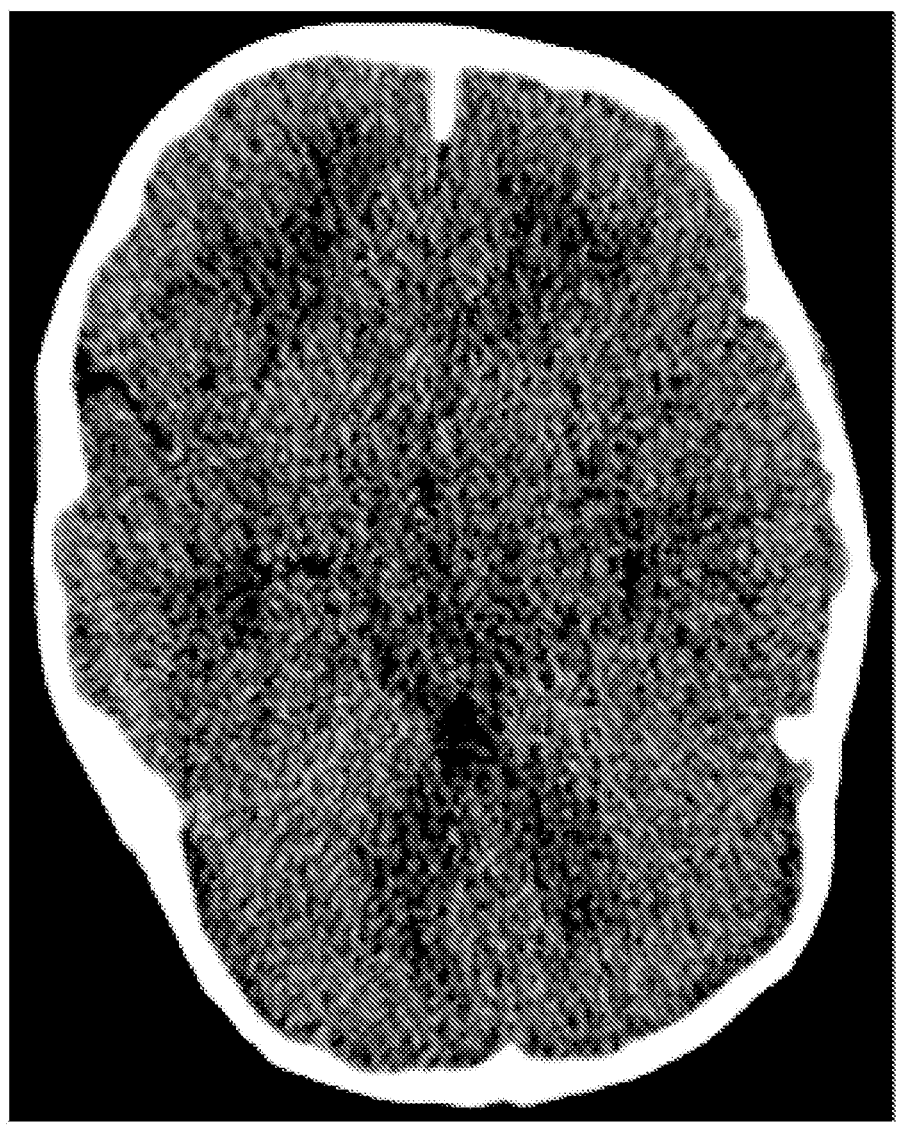
FIGS. 4A-4B are images showing a CT scan of a patient (i.e., Patient 2) with craniosynostosis prior to and after surgery.
Figure 4B:
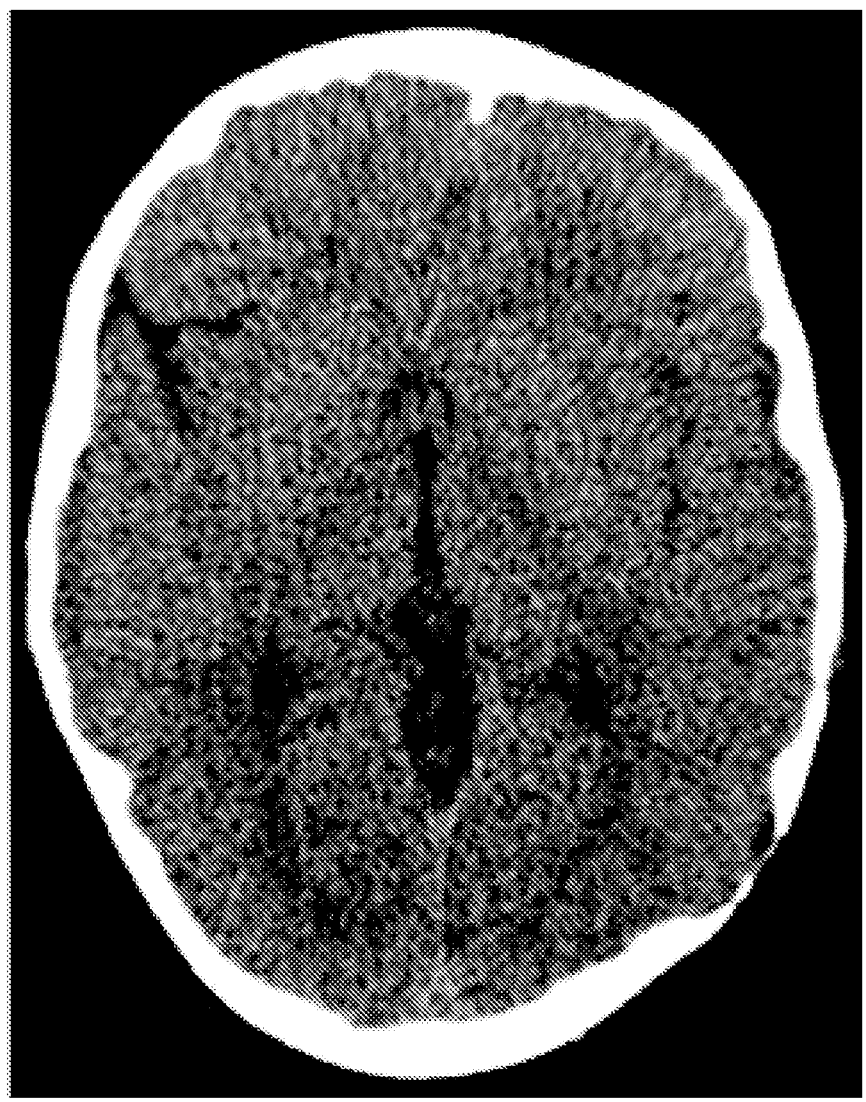

After cranial vault reconstruction, the patient's head circumference increased to 49 cm, approaching the normal curve for the patient's age. Symptoms associated with elevated intracranial pressure resolved, with improvement in her headaches, stabilization of chronic optic nerve edema, and improvement in visual acuity (FIGS. 4A and 4B, taken one year post-operatively).

Example 4. Craniosynostosis Patient 3

Patient 3 was a female infant born with perinatal hypophosphatasia (birth weight was 3060 grams, length was 45 cm, and head circumference was 32 cm). She was prenatally diagnosed by fetal ultrasound with skeletal dysplasia, osteogenesis imperfect (e.g., brittle bone disease), and HPP. After delivery by repeat cesarean section, Patient 3 rapidly developed respiratory distress after delivery requiring positive pressure ventilation for marked subcostal retractions and apnea. The patient was also intubated for oxygen desaturations and remained intubated with assisted ventilation for abnormal chest compliance. The patient was also diagnosed as dysmorphic with a soft cranium and having a large anterior fontanel with widely split sagittal and metopic sutures, short limbs with deformities, talipes equinovarus, brachydactyly, narrow chest, and HPP.

The patient was then evaluated for HPP biomarkers. The initial ALP level was <20 iU/L. Genetic testing revealed two genomic variants of unknown significance (i.e., deletion 1p31.1 and duplication 6q21). ALPL gene testing showed compound heterozygosity with pathogenic variant 876_delAGGGGACinsT and 650T>C of unknown significance. Given the clinical presentation, the genotype was supportive of the diagnosis of HPP. Further testing of ALP activity demonstrated that pyridoxal phosphate was elevated (e.g., >250 mcg/L) and urine phosphoethanolamine was also elevated (e.g., 6025 nmol/mg).

The patient started treatment at 2 months of age with the sALP composition ENB-0040 (asfotase alfa; SEQ ID NO: 19) at a dosage of 1 mg/kg administered subcutaneously six times a week (prior to cranial vault remodeling). CT scan of the cranium at 7 months of age showed poor ossification of the bony structures with diffuse thickening of the calvarium and facial structures. The patient also had brachycephaly with bilateral coronal synostosis. She required open cranial vault remodeling with multiple osteotomies and bilateral parietooccipital remodeling at 8 months of age. Pre-surgical treatment with the sALP composition combined with cranial vault remodeling surgery resulted in an improvement of signs of craniosynostosis, and the patient was transferred to her original managing institution at 16 months, with a body weight of 8.025 kg and body length of 61.5 cm.

Example 5. Craniosynostosis Patient 4

Patient 4 was a female infant born with perinatal hypophosphatasia. Patient 4 presented with bilateral optic nerve edema. CT scan of the cranium showed poor ossification, left coronal craniosynostosis, sagittal craniosynostosis, and metopic synostosis. She required cranial vault remodeling surgery at 22 months of age. Post-operative treatment with the sALP composition combined with cranial vault remodeling surgery resulted in an improvement of signs of craniosynostosis.

Example 6. Craniosynostosis Perinatal Patient 5

A perinatal patient was treated by administration of a sALP combined with a cranial vault remodeling surgery. At birth, the male patient weighed 3460 grams. The patient was intubated and placed on ventilator, then transferred from a community hospital to tertiary care children's hospital. The patient was treated with genetic counseling, and sequencing of the ALPL gene revealed that the patient was a compound heterozygote (c.668 G>A; c.1171 C>T). The patient's Vitamin B6 (pyridoxal phosphate) level was >2000. The patient also exhibited remarkably diminished ossification of the skull, diminished ossification and height of vertebral bodies, absence of humeral ossification, radial and ulnar metaphyses with marked metaphyseal irregularity, fragmentation and fraying, a small chest, and bones abnormal with absent ossification of medial ribs and gracile appearance of the ribs.

Figure 5A:
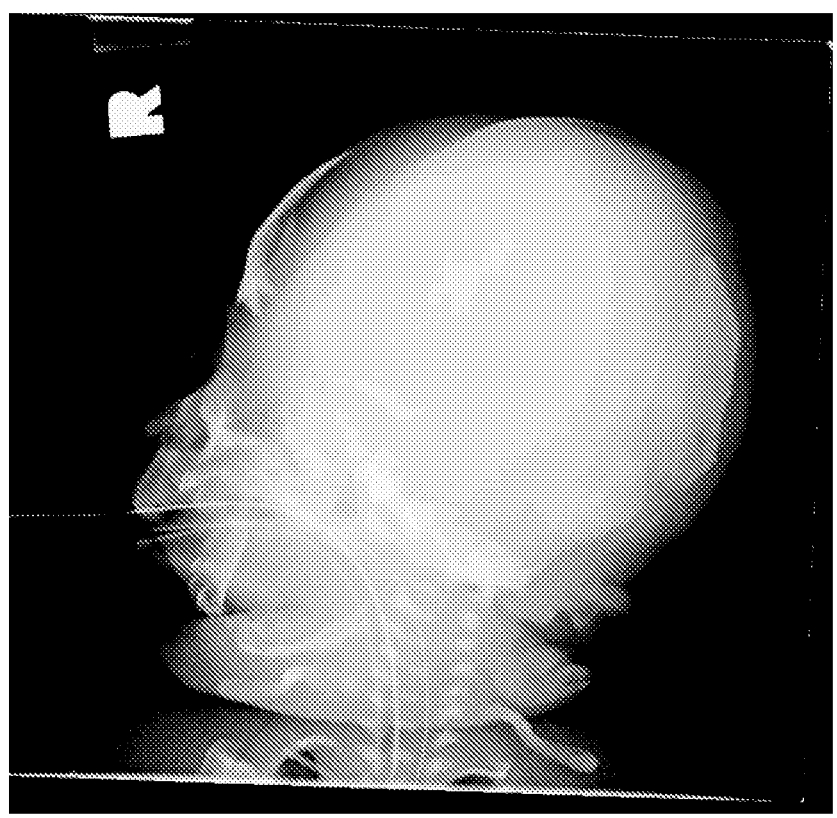
FIGS. 5A-5C are images of a lateral cranial X ray showing is the degree of cranial calcification of Patient 5 performed at ages 1 day (FIG. 5A), 6 months (FIG. 5B), and 18 months (FIG. 5C). There was significant improvement in cranial mineralization after initiation of treatment sALP at age 5 weeks.
Figure 5B:
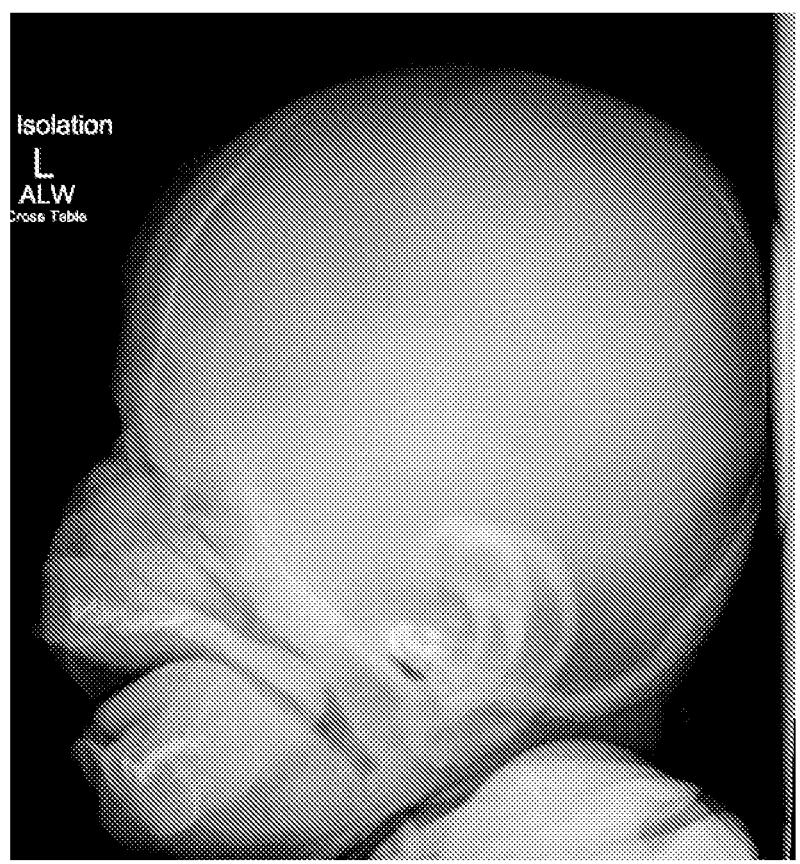
Figure 5C:
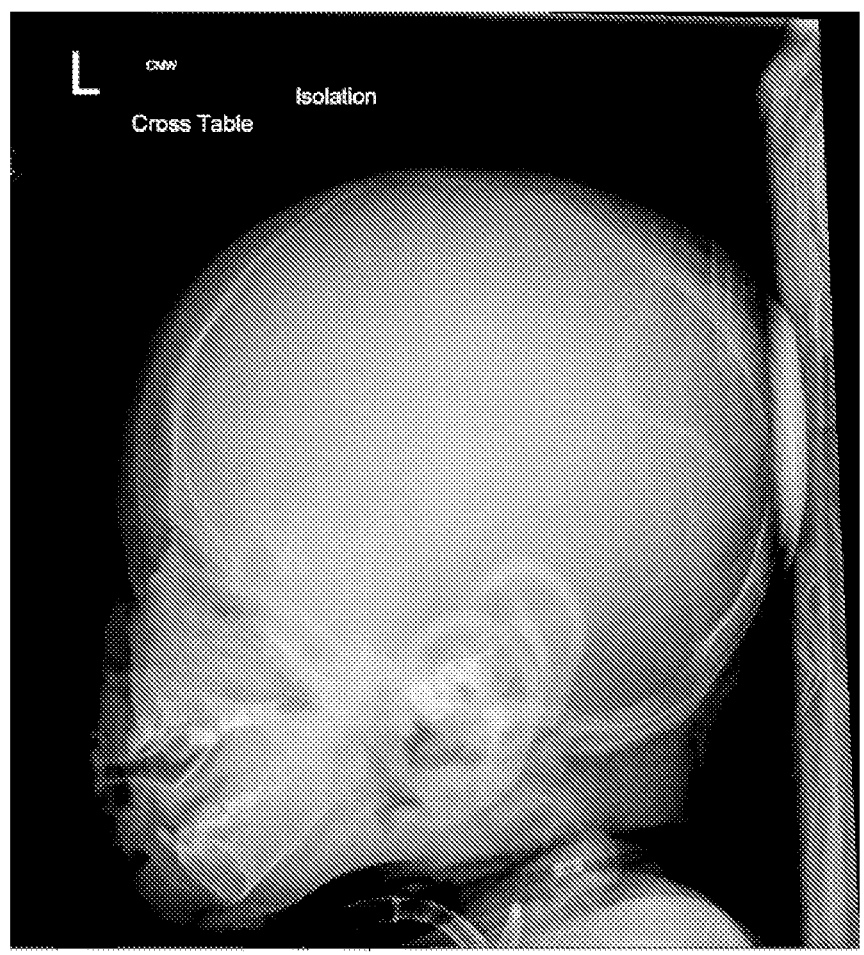
Figure 6A:
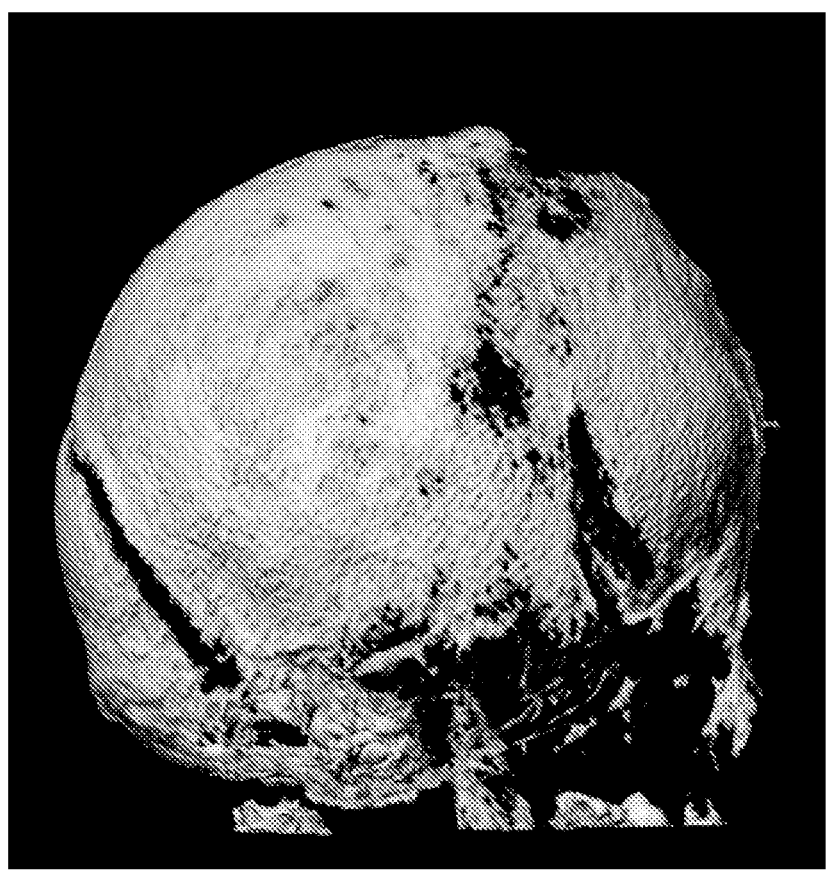
FIGS. 6A-6C are images of a pre-surgical CT scan showing 3D reconstruction of Patient 5 performed at 12 months of age. The CT scan shows decreased mineralization of the cranium with partial synostosis of the right coronal suture (FIG. 6A), left coronal suture (FIG. 6B), and the metopic suture (FIG. 6C).
Figure 6B:
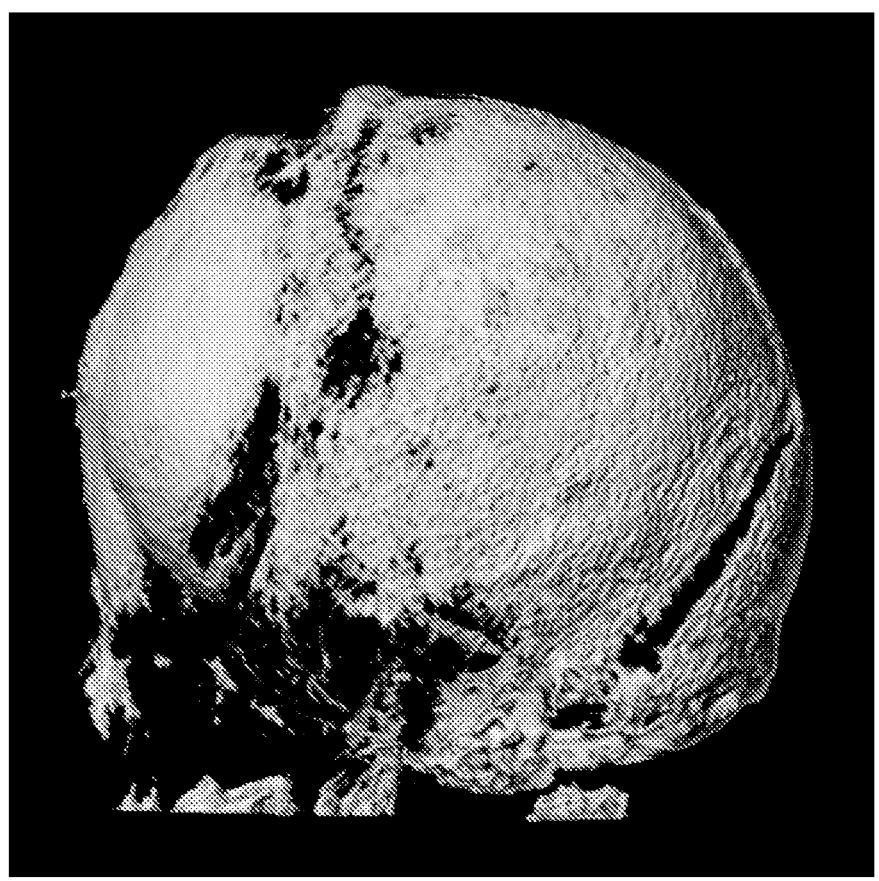
Figure 6C:

The patient began treatment with a sALP composition ENB-0040 (asfotase alfa; SEQ ID NO: 19) at five weeks of age. The patient then exhibited good weight gain (all nutrition by gastrostomy), normal psychosocial development, and increased bone size, while the symptoms of short stature, poor growth of limbs with continued poor mineralization, and gross motor and fine motor delays remained. The growth parameters at 12 months were as follows: weight of 8.585 kg, length of 66 cm, and head circumference of 47.5 cm. While there was almost no cranial calcification at birth, cranial development improved significantly after treatment with the sALP composition (FIGS. 5A-5C). The patient developed coronal synostosis at one year of age requiring posterior cranial vault remodeling and distraction (FIGS. 6A-6C). The patient exhibited significant improvement following treatment with the sALP composition in combination with a cranial vault remodeling procedure.

Example 7. Summary of Case Series

In the setting of craniosynostosis, CSF outflow can be reduced with impaired CSF absorption secondary to venous sinus hypertension. With the skull unable to expand in craniosynostosis, intracranial hypertension occurs. The goal of surgical treatment of HPP-related craniosynostosis is to substantially increase the intracranial volume, thereby decreasing ICP. As seen in our Patient 1 and 2, symptoms associated with suspected elevated ICP (e.g., papilledema, headaches, and emesis) can be reversed with cranial volume augmentation. Treatment with a sALP composition ENB-0040 (asfotase alfa; SEQ ID NO: 19) has improved patient outcomes for those children affected by HPP and has now made it possible to diagnose and surgically treat the secondary effects of the disease, such as craniosynostosis. In our case series, all 4 patients received a sALP composition along with a cranial vault remodeling procedure to treat craniosynostosis (Table 2).

The sALP composition was administered prior to a cranial vault remodeling procedure in one patient, and was administered after a cranial vault remodeling procedure in three patients. The outcomes from the preoperative and postoperative administration of sALP approaches were similar, and the patients did not have surgical complications. Calvarial reconstitution was excellent in the postoperative period for all four patients. These results suggest that surgical correction of HPP-associated craniosynostosis is safe and effective when used in combination with sALP administration.

TABLE 2

Clinical summary of patients.

| Case No. | Age (yrs), Sex | Neurological or skeletal Symptoms | Imaging Modality | Results | sALP | Surgery | Improved Neurological Symptoms |
|---|---|---|---|---|---|---|---|
| 1 | 3 yrs, 9 mos M | Irritability; nausea; vomiting; head-aches; bilateral papilledema | Head CT | Left coronal craniosynostosis; sagittal craniosynostosis; widening of right coronal suture; persistent anterior fontanelle; vol loss of right frontal lobe; prominent scalp veins at vertex, skull base, anterior frontal lobe | After surgery | Yes | Yes |
|   |   |   | Brain MRI | Vol loss of right frontal lobe; congenial absence of right sigmoid sinus; multiple venous anomalies |   |   |   |
| 2 | 5 yrs, 6 mos F | Headaches; nystagmus; decreased visual acuity; microcephaly | Head CT | Scalloping of inner table of skull; absence of extraaxial spaces; left coronal craniosynostosis; sagittal craniosynostosis | After surgery | Yes | Yes |
|   |   |   | Brain MRI | Dysmorphic calvaria |   |   |   |
| 3 | 8 mos F | Brachy-cephaly; ventilator dependence hypotonia | Head CT | Bilateral coronal craniosynostosis | Prior to surgery | Yes | No papilledema |
| 4 | 22 mos F | Bilateral papilledema, hypotonia | Head CT | Left coronal craniosynostosis; sagittal craniosynostosis; metopic synostosis | After surgery | Yes | Yes |
| 5 | M | Brachy-cephaly; ventilator dependence; hypotonia | Head CT | Bilateral coronal craniosynostosis, metopic craniosynostosis | Prior to surgery | Yes | No papilledema |

Other Embodiments

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the claimed invention. Although the disclosure has been described in connection with specific embodiments, it will be understood that it is capable of further modifications and that the invention as claimed should not be unduly limited to such specific embodiments. Indeed, various modifications of the described modes for carrying out the methods according to the disclosure that are obvious to those skilled in the art are intended to be within the scope of the claimed invention. This application is intended to cover any variations, uses, or adaptations of the present disclosure following, in general, the principles of the disclosure and including such departures from the present disclosure come within known customary practice within the art to which the disclosure pertains and may be applied to the essential features herein before set forth.

The invention claimed is:

1. A method of treating craniosynostosis in a human subject with hypophosphatasia (HPP) and exhibiting or likely to have increased intracranial pressure (ICP), comprising administering a soluble alkaline phosphatase (sALP) to the subject in combination with at least one cranial vault remodeling procedure, wherein the HPP is infantile HPP, childhood HPP, perinatal benign HPP, or perinatal lethal HPP, wherein the sALP is administered to the subject from about two months to about 1 day prior to, and no sooner than at least about two weeks after, the at least one cranial vault remodeling procedure, and wherein the subject is not in utero and is not a neonate.

2. The method of claim 1, wherein the sALP is administered to the subject from about two weeks to about two months after, the cranial vault remodeling procedure.

3. The method of claim 1, wherein:
a) the subject is diagnosed with craniosynostosis prior to administration of the sALP;
b) the subject exhibits one or more additional symptoms of craniosynostosis;
c) the method further comprises monitoring ICP in the subject; and/or
d) the subject exhibits an improvement in one or more symptoms of craniosynostosis.

4. The method of claim 3, wherein the monitoring comprises at least one of radiography, ultrasonography, clinical examination, and/or determination of sALP activity.

5. The method of claim 4, wherein the determination of sALP activity comprises measuring at least one of phosphoethanolamine (PEA), inorganic pyrophosphate (PPi), and/or pyridoxal 5'-phosphate (PLP) in a serum and/or blood sample from the subject.

6. The method of claim 1, wherein the sALP is administered in an amount that is therapeutically effective to treat increased ICP, one or more additional symptoms of craniosynostosis, and/or at least one symptom of HPP.

7. The method of claim 6, wherein the one or more additional symptoms of craniosynostosis comprises headaches, irritability, nausea and emesis (vomiting), pulsatile tinnitus, hearing loss, abnormal skull and facial shapes, airway impairments, obstructive sleep apnea, Chiari Type I malformation, brain abnormalities, blindness, vision impairment, double vision, decreased visual acuity, deafness, seizures, impairments in mental development, herniation of cerebellar tonsils, syringomyelia, bilateral papilledema, nystagmus, microcephaly, brachycephaly, dolichocephaly, ventilator dependence, and/or chronic optic nerve edema; and/or wherein the symptom of HPP comprises premature loss of deciduous teeth, incomplete bone mineralization, elevated blood and/or urine levels of inorganic pyrophosphate PPi, elevated blood and/or urine levels of phosphoethanolamine (PEA), elevated blood and/or urine levels of pyridoxal 5'-phosphate (PLP), hypomineralization, rachitic ribs, hypercalciuria, short stature, skeletal deformity, waddling gait, bone pain, bone fracture, HPP-related seizure, inadequate weight gain, rickets, and/or calcium pyrophosphate dihydrate crystal deposition.

8. The method of claim 1, wherein the sALP is formulated in a pharmaceutical composition with a pharmaceutically acceptable carrier, wherein, optionally, the pharmaceutically acceptable carrier is saline.

9. The method of claim 8, wherein the pharmaceutical composition is formulated for intramuscular, subcutaneous, intravenous, oral, nasal, sublingual, intrathecal, or intradermal administration and is formulated for daily or weekly administration.

10. The method of claim 1, wherein:
   a) the sALP is administered to the subject at a dosage of about 0.1 mg/kg to about 20 mg/kg, or at a weekly dosage of about 0.5 mg/kg to about 140 mg/kg;
   b) the sALP is physiologically active toward phosphoethanolamine (PEA), inorganic pyrophosphate (PPi), and pyridoxal 5'-phosphate (PLP);
   c) the sALP is catalytically competent to improve skeletal mineralization in bone; and/or
   d) the sALP is the soluble extracellular domain of an alkaline phosphatase selected from the group consisting of tissue non-specific alkaline phosphatase (TNALP), placental alkaline phosphatase (PALP), germ cell alkaline phosphatase (GCALP), and intestinal alkaline phosphatase (IALP).

11. The method of claim 10, wherein the sALP is TNALP.

12. The method of claim 11, wherein:
   a) the TNALP comprises an amino acid sequence as set forth in SEQ ID NOs: 1, 2, 3, 4, or 5;
   b) the TNALP comprises an amino acid sequence as set forth in SEQ ID NO: 6;
   c) the TNALP comprises an amino acid sequence as set forth in SEQ ID NO: 7;
   d) the TNALP comprises an amino acid sequence as set forth in SEQ ID NO: 8;
   e) the TNALP comprises an amino acid sequence as set forth in SEQ ID NO: 9;
   f) the TNALP comprises an amino acid sequence as set forth in SEQ ID NO: 10;
   g) the TNALP comprises an amino acid sequence as set forth in SEQ ID NO: 11, 12, or 13; or
   h) the TNALP comprises an amino acid sequence as set forth in SEQ ID NO: 14.

13. The method of claim 10, wherein
   a) the PALP comprises an amino acid sequence as set forth in SEQ ID NOs: 15 or 16;
   b) the GCALP comprises an amino acid sequence as set forth in SEQ ID NO: 17; or
   c) the IALP comprises an amino acid sequence as set forth in SEQ ID NO: 18.

14. The method of claim 1, wherein the sALP comprises a polypeptide having the structure selected from the group consisting of Z-sALP-Y-spacer-X-$W_n$-V and Z-$W_n$-X-sALP-Y-spacer-V, wherein:
   V is absent or is an amino acid sequence of at least one amino acid;
   X is absent or is an amino acid sequence of at least one amino acid;
   Y is absent or is an amino acid sequence of at least one amino acid;
   Z is absent or is an amino acid sequence of at least one amino acid; and
   $W_n$ is a bone-targeting moiety.

15. The method of claim 14, wherein the structure is Z-sALP-Y-spacer-X-$W_n$-V, and/or wherein the bone-targeting moiety is a polyaspartic or polyglutamic region.

16. The method of claim 15, wherein n=1-50.

17. The method of claim 14, wherein the spacer comprises a fragment crystallizable (Fc) region, wherein, optionally, the Fc region comprises a CH2 domain, a CH3 domain, and a hinge region and/or the Fc is a constant domain of an immunoglobulin selected from the group consisting of IgG-1, IgG-2, IgG-3, and IgG-4.

18. The method of claim 14, wherein at least one of V, Z, and the spacer is absent, and wherein Y and X are independently two amino acid residues.

19. The method of claim 18, wherein Y is leucine-lysine and/or X is aspartate-isoleucine.

20. The method of claim 1, wherein the sALP comprises an amino acid sequence as set forth in SEQ ID NO: 19.

21. The method of claim 2, wherein the sALP is administered to the subject about six weeks, one month, three weeks, two weeks, one week, 6 days, 5 days, four days, or two days prior to or about six weeks, one month, or three weeks after the cranial vault remodeling procedure.

22. The method of claim 16, wherein n=3-30.

23. The method of claim 22, wherein n=5-15.

24. The method of claim 23, wherein n=10.

25. The method of claim 3, wherein the one or more symptoms of craniosynostosis comprises neurological symptoms, headaches, irritability, nausea and emesis (vomiting), pulsatile tinnitus, hearing loss, abnormal skull and facial shapes, airway impairments, obstructive sleep apnea, Chiari Type I malformation, brain abnormalities, blindness, vision impairment, double vision, decreased visual acuity, deafness, seizures, impairments in mental development, herniation of cerebellar tonsils, syringomyelia, bilateral papilledema, nystagmus, microcephaly, brachycephaly, dolichocephaly, ventilator dependence, and/or chronic optic nerve edema.

26. The method of claim 4, wherein, the radiography comprises a computed tomography (CT) scan.

27. The method of claim 1, further comprising detecting a mutation in a fibroblast growth factor receptor (FGFR) in a sample from the subject prior to the administration of the sALP and prior to the at least one cranial vault remodeling procedure.

28. The method of claim 27, further comprising testing a parent of the subject for the FGFR mutation.

29. The method of claim 1 further comprising monitoring the ICP either directly and continuously using a probe passed through a skull of the subject or indirectly via a lumbar cerebrospinal fluid catheter.

* * * * *